(12) United States Patent
Shelton, IV et al.

(10) Patent No.: US 10,441,279 B2
(45) Date of Patent: Oct. 15, 2019

(54) MULTIPLE LEVEL THRESHOLDS TO MODIFY OPERATION OF POWERED SURGICAL INSTRUMENTS

(71) Applicant: Ethicon Endo-Surgery, LLC, Guaynabo, PR (US)

(72) Inventors: Frederick E. Shelton, IV, Hillsboro, OH (US); David C. Yates, West Chester, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 480 days.

(21) Appl. No.: 14/640,795

(22) Filed: Mar. 6, 2015

(65) Prior Publication Data

US 2016/0256185 A1 Sep. 8, 2016

(51) Int. Cl.
 *A61B 17/068* (2006.01)
 *A61B 17/072* (2006.01)
 (Continued)

(52) U.S. Cl.
 CPC ...... *A61B 17/068* (2013.01); *A61B 17/07207* (2013.01); *A61B 2017/00017* (2013.01);
 (Continued)

(58) Field of Classification Search
 CPC ...... H02P 29/032; H02P 29/40; A61B 17/068; A61B 17/072; A61B 17/07207;
 (Continued)

(56) References Cited

U.S. PATENT DOCUMENTS

| 719,487 | A | 2/1903 | Minor |
|---|---|---|---|
| 804,229 | A | 11/1905 | Hutchinson |

(Continued)

FOREIGN PATENT DOCUMENTS

| CA | 1125615 A | 6/1982 |
|---|---|---|
| CA | 2664874 A1 | 11/2009 |

(Continued)

OTHER PUBLICATIONS

Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.

(Continued)

*Primary Examiner* — Stephen F. Gerrity
*Assistant Examiner* — Joshua G Kotis

(57) ABSTRACT

Thresholds can be assigned for one or more parameters in connection with the operation of a surgical device. An ultimate threshold can trigger a desired action, including cessation of operations or modification of operations, if the ultimate threshold is reached, or predicted to be reached. In addition, a marginal threshold can trigger a desired action, including improving operations such as slowing operations where the value of a parameter is measured to be between the values defined by a marginal threshold and an ultimate threshold. Multiple thresholds, based on multiple parameters, can be defined, further enabling calibrated usage, such as slowing operations based on exceeding both a marginal threshold based on number of sterilization cycles and exceeding a marginal threshold based on extent to which current draw exceeds a certain value.

14 Claims, 44 Drawing Sheets

(51) Int. Cl.
  *A61B 18/00* (2006.01)
  *A61B 17/00* (2006.01)
  *A61B 90/00* (2016.01)
  *A61B 90/70* (2016.01)

(52) U.S. Cl.
  CPC .............. *A61B 2017/00022* (2013.01); *A61B 2017/00123* (2013.01); *A61B 2017/00132* (2013.01); *A61B 2017/00398* (2013.01); *A61B 2018/00648* (2013.01); *A61B 2018/00666* (2013.01); *A61B 2090/064* (2016.02); *A61B 2090/0803* (2016.02); *A61B 2090/0807* (2016.02); *A61B 2090/702* (2016.02)

(58) Field of Classification Search
  CPC ............................... A61B 2018/00648; A61B 2018/00666–00678; A61B 2018/00827; A61B 2018/00833; A61B 2018/00892; A61B 2018/00791
  USPC ............................................. 227/175.1–182.1
  See application file for complete search history.

(56) References Cited

U.S. PATENT DOCUMENTS

| | | |
|---|---|---|
| 1,849,427 A | 3/1932 | Hook |
| 1,944,116 A | 1/1934 | Stratman |
| 1,954,048 A | 4/1934 | Jeffrey et al. |
| 2,224,882 A | 12/1940 | Peck |
| 2,377,581 A | 6/1945 | Shaffrey |
| 2,638,901 A | 5/1953 | Sugarbaker |
| 2,742,955 A | 4/1956 | Dominguez |
| 2,957,353 A | 10/1960 | Lewis |
| 3,060,972 A | 10/1962 | Sheldon |
| 3,080,564 A | 3/1963 | Strekopitov et al. |
| 3,180,236 A | 4/1965 | Beckett |
| 3,269,631 A | 8/1966 | Takaro |
| 3,359,978 A | 12/1967 | Smith, Jr. |
| 3,480,193 A | 11/1969 | Ralston |
| 3,509,629 A | 5/1970 | Kidokoro |
| 3,589,589 A | 6/1971 | Akopov |
| 3,618,842 A | 11/1971 | Bryan |
| 3,638,652 A | 2/1972 | Kelley |
| 3,650,453 A | 3/1972 | Smith, Jr. |
| 3,688,966 A | 9/1972 | Perkins et al. |
| 3,727,904 A | 4/1973 | Gabbey |
| 3,747,603 A | 7/1973 | Adler |
| 3,752,161 A | 8/1973 | Bent |
| 3,808,452 A | 4/1974 | Hutchinson |
| 3,815,476 A | 6/1974 | Green et al. |
| 3,836,171 A | 9/1974 | Hayashi et al. |
| 3,837,555 A | 9/1974 | Green |
| 3,863,639 A | 2/1975 | Kleaveland |
| 3,883,624 A | 5/1975 | McKenzie et al. |
| 3,902,247 A | 9/1975 | Fleer et al. |
| 3,944,163 A | 3/1976 | Hayashi et al. |
| 3,952,747 A | 4/1976 | Kimmell, Jr. |
| 3,959,879 A | 6/1976 | Sellers |
| 3,972,734 A | 8/1976 | King |
| 4,025,216 A | 5/1977 | Hives |
| 4,027,746 A | 6/1977 | Kine |
| 4,034,143 A | 7/1977 | Sweet |
| 4,066,133 A | 1/1978 | Voss |
| 4,100,820 A | 7/1978 | Evett |
| 4,108,211 A | 8/1978 | Tanaka |
| 4,127,227 A | 11/1978 | Green |
| 4,132,146 A | 1/1979 | Uhlig |
| 4,135,517 A | 1/1979 | Reale |
| 4,154,122 A | 5/1979 | Severin |
| 4,185,701 A | 1/1980 | Boys |
| 4,190,042 A | 2/1980 | Sinnreich |
| 4,239,431 A | 12/1980 | Davini |
| 4,241,861 A | 12/1980 | Fleischer |
| 4,274,398 A | 6/1981 | Scott, Jr. |
| 4,278,091 A | 7/1981 | Borzone |
| 4,289,131 A | 9/1981 | Mueller |
| 4,290,542 A | 9/1981 | Fedotov et al. |
| D261,356 S | 10/1981 | Robinson |
| 4,296,881 A | 10/1981 | Lee |
| 4,312,363 A | 1/1982 | Rothfuss et al. |
| 4,319,576 A | 3/1982 | Rothfuss |
| 4,321,746 A | 3/1982 | Grinage |
| 4,350,151 A | 9/1982 | Scott |
| 4,357,940 A | 11/1982 | Muller |
| 4,361,057 A | 11/1982 | Kochera |
| 4,366,544 A | 12/1982 | Shima et al. |
| 4,376,380 A | 3/1983 | Burgess |
| 4,406,621 A | 9/1983 | Bailey |
| 4,417,890 A | 11/1983 | Dennehey et al. |
| 4,430,997 A | 2/1984 | DiGiovanni et al. |
| 4,452,376 A | 6/1984 | Klieman et al. |
| 4,461,305 A | 7/1984 | Cibley |
| 4,469,481 A | 9/1984 | Kobayashi |
| 4,471,780 A | 9/1984 | Menges et al. |
| 4,471,781 A | 9/1984 | Di Giovanni et al. |
| 4,478,220 A | 10/1984 | Di Giovanni et al. |
| 4,480,641 A | 11/1984 | Failla et al. |
| 4,493,983 A | 1/1985 | Taggert |
| D278,081 S | 3/1985 | Green |
| 4,503,842 A | 3/1985 | Takayama |
| 4,530,357 A | 7/1985 | Pawloski et al. |
| 4,540,202 A | 9/1985 | Amphoux et al. |
| 4,556,058 A | 12/1985 | Green |
| 4,560,915 A | 12/1985 | Soultanian |
| 4,569,346 A | 2/1986 | Poirier |
| 4,576,165 A | 3/1986 | Green et al. |
| 4,586,501 A | 5/1986 | Claracq |
| 4,586,502 A | 5/1986 | Bedi et al. |
| 4,589,870 A | 5/1986 | Citrin et al. |
| RE32,214 E | 7/1986 | Schramm |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |
| D287,278 S | 12/1986 | Spreckelmeier |
| 4,633,861 A | 1/1987 | Chow et al. |
| 4,635,638 A | 1/1987 | Weintraub et al. |
| 4,642,618 A | 2/1987 | Johnson et al. |
| 4,643,173 A | 2/1987 | Bell et al. |
| 4,646,745 A | 3/1987 | Noiles |
| 4,652,820 A | 3/1987 | Maresca |
| 4,654,028 A | 3/1987 | Suma |
| 4,671,278 A | 6/1987 | Chin |
| 4,671,280 A | 6/1987 | Dorband et al. |
| 4,672,964 A | 6/1987 | Dee et al. |
| 4,675,944 A | 6/1987 | Wells |
| 4,679,460 A | 7/1987 | Yoshigai |
| 4,679,719 A | 7/1987 | Kramer |
| 4,688,555 A | 8/1987 | Wardle |
| 4,698,579 A | 10/1987 | Richter et al. |
| 4,705,038 A | 11/1987 | Sjostrom et al. |
| 4,721,099 A | 1/1988 | Chikama |
| 4,724,840 A | 2/1988 | McVay et al. |
| 4,744,363 A | 5/1988 | Hasson |
| 4,761,326 A | 8/1988 | Barnes et al. |
| 4,763,669 A | 8/1988 | Jaeger |
| D297,764 S | 9/1988 | Hunt et al. |
| 4,781,186 A | 11/1988 | Simpson et al. |
| 4,784,137 A | 11/1988 | Kulik et al. |
| D298,967 S | 12/1988 | Hunt |
| 4,790,314 A | 12/1988 | Weaver |
| 4,807,628 A | 2/1989 | Peters et al. |
| 4,817,643 A | 4/1989 | Olson |
| 4,828,542 A | 5/1989 | Hermann |
| 4,828,944 A | 5/1989 | Yabe et al. |
| 4,833,937 A | 5/1989 | Nagano |
| 4,838,859 A | 6/1989 | Strassmann |
| 4,860,644 A | 8/1989 | Kohl et al. |
| 4,862,891 A | 9/1989 | Smith |
| 4,863,423 A | 9/1989 | Wallace |
| 4,894,051 A | 1/1990 | Shiber |
| 4,896,584 A | 1/1990 | Stoll et al. |
| 4,909,789 A | 3/1990 | Taguchi et al. |

(56) References Cited

U.S. PATENT DOCUMENTS

| | | | |
|---|---|---|---|
| 4,919,679 A | 4/1990 | Averill et al. | |
| 4,921,479 A | 5/1990 | Grayzel | |
| 4,925,082 A | 5/1990 | Kim | |
| 4,928,699 A | 5/1990 | Sasai | |
| 4,931,737 A | 6/1990 | Hishiki | |
| 4,933,800 A | 6/1990 | Yang | |
| D309,350 S | 7/1990 | Sutherland et al. | |
| 4,946,067 A | 8/1990 | Kelsall | |
| 4,948,327 A | 8/1990 | Crupi, Jr. | |
| 4,949,707 A | 8/1990 | LeVahn et al. | |
| 4,951,861 A | 8/1990 | Schulze et al. | |
| 4,957,212 A | 9/1990 | Duck et al. | |
| 4,962,877 A | 10/1990 | Hervas | |
| 4,964,559 A | 10/1990 | Deniega et al. | |
| 4,964,863 A | 10/1990 | Kanshin et al. | |
| 4,973,302 A | 11/1990 | Armour et al. | |
| 4,979,952 A | 12/1990 | Kubota et al. | |
| 4,984,564 A | 1/1991 | Yuen | |
| 4,987,049 A | 1/1991 | Komamura et al. | |
| 4,995,877 A | 2/1991 | Ams et al. | |
| 4,995,959 A | 2/1991 | Metzner | |
| 4,996,975 A | 3/1991 | Nakamura | |
| 5,012,411 A | 4/1991 | Policastro et al. | |
| 5,014,898 A | 5/1991 | Heidrich | |
| 5,024,652 A | 6/1991 | Dumenek et al. | |
| 5,025,559 A | 6/1991 | McCullough | |
| 5,030,226 A | 7/1991 | Green et al. | |
| 5,038,247 A | 8/1991 | Kelley et al. | |
| 5,062,491 A * | 11/1991 | Takeshima | B25B 21/008 173/1 |
| 5,077,506 A | 12/1991 | Krause | |
| 5,089,606 A | 2/1992 | Cole et al. | |
| 5,098,004 A | 3/1992 | Kerrigan | |
| 5,098,360 A | 3/1992 | Hirota | |
| 5,100,042 A | 3/1992 | Gravener et al. | |
| 5,104,400 A | 4/1992 | Berguer et al. | |
| 5,109,722 A | 5/1992 | Hufnagle et al. | |
| D327,323 S | 6/1992 | Hunt | |
| 5,119,009 A | 6/1992 | McCaleb et al. | |
| 5,168,605 A | 12/1992 | Bartlett | |
| 5,170,925 A | 12/1992 | Madden et al. | |
| 5,173,133 A | 12/1992 | Morin et al. | |
| 5,176,677 A | 1/1993 | Wuchinich | |
| 5,176,688 A | 1/1993 | Narayan et al. | |
| 5,187,422 A | 2/1993 | Izenbaard et al. | |
| 5,188,102 A | 2/1993 | Idemoto et al. | |
| 5,195,505 A | 3/1993 | Josefsen | |
| 5,197,970 A | 3/1993 | Green et al. | |
| 5,201,750 A | 4/1993 | Hocherl et al. | |
| 5,209,747 A | 5/1993 | Knoepfler | |
| 5,209,756 A | 5/1993 | Seedhom et al. | |
| 5,220,269 A | 6/1993 | Chen et al. | |
| 5,222,945 A | 6/1993 | Basnight | |
| D338,729 S | 8/1993 | Sprecklemeier et al. | |
| 5,236,424 A | 8/1993 | Imran | |
| 5,258,007 A | 11/1993 | Spetzler et al. | |
| 5,258,008 A | 11/1993 | Wilk | |
| 5,258,010 A | 11/1993 | Green et al. | |
| 5,261,877 A | 11/1993 | Fine et al. | |
| 5,261,922 A | 11/1993 | Hood | |
| 5,263,937 A | 11/1993 | Shipp | |
| 5,275,322 A | 1/1994 | Brinkerhoff et al. | |
| 5,286,253 A | 2/1994 | Fucci | |
| 5,290,310 A | 3/1994 | Makower et al. | |
| 5,293,024 A | 3/1994 | Sugahara et al. | |
| D347,474 S | 5/1994 | Olson | |
| 5,308,576 A | 5/1994 | Green et al. | |
| 5,313,935 A | 5/1994 | Kortenbach et al. | |
| 5,313,967 A | 5/1994 | Lieber et al. | |
| 5,320,627 A | 6/1994 | Sorensen et al. | |
| D348,930 S | 7/1994 | Olson | |
| 5,326,013 A | 7/1994 | Green et al. | |
| 5,329,923 A | 7/1994 | Lundquist | |
| 5,331,971 A | 7/1994 | Bales et al. | |
| 5,336,130 A | 8/1994 | Ray | |
| 5,336,229 A | 8/1994 | Noda | |
| 5,341,807 A | 8/1994 | Nardella | |
| 5,342,380 A | 8/1994 | Hood | |
| 5,342,385 A | 8/1994 | Norelli et al. | |
| 5,343,382 A | 8/1994 | Hale et al. | |
| 5,344,059 A | 9/1994 | Green et al. | |
| 5,350,355 A | 9/1994 | Sklar | |
| 5,354,250 A | 10/1994 | Christensen | |
| 5,356,064 A | 10/1994 | Green et al. | |
| 5,359,993 A | 11/1994 | Slater et al. | |
| 5,364,002 A | 11/1994 | Green et al. | |
| 5,369,565 A | 11/1994 | Chen et al. | |
| 5,375,588 A | 12/1994 | Yoon | |
| 5,381,943 A | 1/1995 | Allen et al. | |
| 5,383,882 A | 1/1995 | Buess et al. | |
| 5,388,568 A | 2/1995 | van der Heide | |
| 5,389,102 A | 2/1995 | Green et al. | |
| 5,400,267 A | 3/1995 | Denen et al. | |
| 5,403,276 A | 4/1995 | Schechter et al. | |
| 5,404,106 A | 4/1995 | Matsuda | |
| 5,404,870 A | 4/1995 | Brinkerhoff et al. | |
| 5,404,960 A | 4/1995 | Wada et al. | |
| 5,409,703 A | 4/1995 | McAnalley et al. | |
| D357,981 S | 5/1995 | Green et al. | |
| 5,419,766 A | 5/1995 | Chang et al. | |
| 5,423,835 A | 6/1995 | Green et al. | |
| 5,427,298 A | 6/1995 | Tegtmeier | |
| 5,431,323 A | 7/1995 | Smith et al. | |
| 5,443,197 A | 8/1995 | Malis et al. | |
| 5,443,463 A | 8/1995 | Stern et al. | |
| 5,445,604 A | 8/1995 | Lang | |
| 5,454,822 A | 10/1995 | Schob et al. | |
| 5,456,917 A | 10/1995 | Wise et al. | |
| 5,458,279 A | 10/1995 | Plyley | |
| 5,465,819 A | 11/1995 | Weilant et al. | |
| 5,470,008 A | 11/1995 | Rodak | |
| 5,471,129 A | 11/1995 | Mann | |
| 5,476,481 A | 12/1995 | Schondorf | |
| 5,483,952 A | 1/1996 | Aranyi | |
| 5,489,290 A | 2/1996 | Furnish | |
| 5,490,819 A | 2/1996 | Nicholas et al. | |
| 5,492,671 A | 2/1996 | Krafft | |
| 5,514,149 A | 5/1996 | Green et al. | |
| 5,520,609 A | 5/1996 | Moll et al. | |
| 5,520,634 A | 5/1996 | Fox et al. | |
| 5,527,264 A | 6/1996 | Moll et al. | |
| 5,531,856 A | 7/1996 | Moll et al. | |
| 5,540,705 A | 7/1996 | Meade et al. | |
| 5,541,489 A | 7/1996 | Dunstan | |
| 5,543,695 A | 8/1996 | Culp et al. | |
| 5,544,802 A | 8/1996 | Crainich | |
| 5,553,624 A | 9/1996 | Francese et al. | |
| 5,556,020 A | 9/1996 | Hou | |
| 5,558,533 A | 9/1996 | Hashizawa et al. | |
| 5,573,169 A | 11/1996 | Green et al. | |
| 5,578,052 A | 11/1996 | Koros et al. | |
| 5,582,907 A | 12/1996 | Pall | |
| 5,583,114 A | 12/1996 | Barrows et al. | |
| 5,599,350 A | 2/1997 | Schulze et al. | |
| 5,601,604 A | 2/1997 | Vincent | |
| 5,602,449 A | 2/1997 | Krause et al. | |
| 5,607,474 A | 3/1997 | Athanasiou et al. | |
| 5,613,499 A | 3/1997 | Palmer et al. | |
| 5,613,937 A | 3/1997 | Garrison et al. | |
| 5,614,887 A | 3/1997 | Buchbinder | |
| 5,620,326 A | 4/1997 | Younker | |
| 5,633,374 A | 5/1997 | Humphrey et al. | |
| D381,077 S | 7/1997 | Hunt | |
| 5,643,294 A | 7/1997 | Tovey et al. | |
| 5,643,319 A | 7/1997 | Green et al. | |
| 5,651,762 A | 7/1997 | Bridges | |
| 5,651,821 A | 7/1997 | Uchida | |
| 5,657,417 A | 8/1997 | Di Troia | |
| 5,658,298 A | 8/1997 | Vincent et al. | |
| 5,681,341 A | 10/1997 | Lunsford et al. | |
| 5,700,276 A | 12/1997 | Benecke | |
| 5,709,335 A | 1/1998 | Heck | |
| 5,715,604 A | 2/1998 | Lanzoni | |
| 5,724,025 A | 3/1998 | Tavori | |

(56) References Cited

U.S. PATENT DOCUMENTS

| | | |
|---|---|---|
| 5,728,113 A | 3/1998 | Sherts |
| 5,738,629 A | 4/1998 | Moll et al. |
| 5,741,271 A | 4/1998 | Nakao et al. |
| 5,749,968 A | 5/1998 | Melanson et al. |
| 5,752,970 A | 5/1998 | Yoon |
| 5,769,303 A | 6/1998 | Knodel et al. |
| 5,769,791 A | 6/1998 | Benaron et al. |
| 5,782,748 A | 7/1998 | Palmer et al. |
| 5,791,231 A | 8/1998 | Cohn et al. |
| 5,792,162 A | 8/1998 | Jolly et al. |
| 5,792,573 A | 8/1998 | Pitzen et al. |
| 5,797,637 A | 8/1998 | Ervin |
| 5,797,927 A | 8/1998 | Yoon |
| 5,797,941 A | 8/1998 | Schulze et al. |
| 5,804,726 A | 9/1998 | Geib et al. |
| 5,804,936 A | 9/1998 | Brodsky et al. |
| 5,830,598 A | 11/1998 | Patterson |
| 5,839,369 A | 11/1998 | Chatterjee et al. |
| 5,847,566 A | 12/1998 | Marritt et al. |
| 5,849,020 A | 12/1998 | Long et al. |
| 5,851,179 A | 12/1998 | Ritson et al. |
| 5,853,366 A | 12/1998 | Dowlatshahi |
| 5,865,638 A | 2/1999 | Trafton |
| 5,868,361 A | 2/1999 | Rinderer |
| 5,868,790 A | 2/1999 | Vincent et al. |
| 5,881,777 A | 3/1999 | Bassi et al. |
| 5,891,094 A | 4/1999 | Masterson et al. |
| 5,891,558 A | 4/1999 | Bell et al. |
| 5,899,824 A | 5/1999 | Kurtz et al. |
| 5,906,577 A | 5/1999 | Beane et al. |
| 5,907,211 A | 5/1999 | Hall et al. |
| 5,909,062 A | 6/1999 | Krietzman |
| 5,924,864 A | 7/1999 | Loge et al. |
| 5,928,137 A | 7/1999 | Green |
| 5,946,978 A | 9/1999 | Yamashita |
| 5,947,996 A | 9/1999 | Logeman |
| 5,948,429 A | 9/1999 | Bell et al. |
| 5,951,301 A | 9/1999 | Younker |
| D416,089 S | 11/1999 | Barton et al. |
| 5,976,122 A | 11/1999 | Madhani et al. |
| 5,980,248 A | 11/1999 | Kusakabe et al. |
| 5,990,379 A | 11/1999 | Gregory |
| 5,993,466 A | 11/1999 | Yoon |
| 6,007,521 A | 12/1999 | Bidwell et al. |
| 6,010,520 A | 1/2000 | Pattison |
| 6,019,745 A | 2/2000 | Gray |
| 6,024,708 A | 2/2000 | Bales et al. |
| 6,024,750 A | 2/2000 | Mastri et al. |
| 6,030,384 A | 2/2000 | Nezhat |
| 6,033,105 A | 3/2000 | Barker et al. |
| 6,036,667 A | 3/2000 | Manna et al. |
| 6,042,607 A | 3/2000 | Williamson, IV et al. |
| 6,043,626 A | 3/2000 | Snyder et al. |
| 6,050,172 A | 4/2000 | Corves et al. |
| 6,050,989 A | 4/2000 | Fox et al. |
| 6,053,899 A | 4/2000 | Slanda et al. |
| 6,054,142 A | 4/2000 | Li et al. |
| 6,059,806 A | 5/2000 | Hoegerle |
| 6,063,025 A | 5/2000 | Bridges et al. |
| 6,063,050 A | 5/2000 | Manna et al. |
| 6,066,151 A | 5/2000 | Miyawaki et al. |
| 6,077,280 A | 6/2000 | Fossum |
| 6,077,290 A | 6/2000 | Marini |
| 6,083,223 A | 7/2000 | Baker |
| 6,104,162 A | 8/2000 | Sainsbury et al. |
| 6,110,187 A | 8/2000 | Donlon |
| 6,113,618 A | 9/2000 | Nic |
| 6,123,701 A | 9/2000 | Nezhat |
| 6,142,149 A | 11/2000 | Steen |
| 6,142,933 A | 11/2000 | Longo et al. |
| 6,147,135 A | 11/2000 | Yuan et al. |
| 6,151,323 A | 11/2000 | O'Connell et al. |
| 6,157,169 A | 12/2000 | Lee |
| 6,162,220 A | 12/2000 | Nezhat |
| 6,167,185 A | 12/2000 | Smiley et al. |
| 6,173,074 B1 | 1/2001 | Russo |
| 6,174,318 B1 | 1/2001 | Bates et al. |
| 6,185,356 B1 | 2/2001 | Parker et al. |
| 6,186,142 B1 | 2/2001 | Schmidt et al. |
| 6,206,894 B1 | 3/2001 | Thompson et al. |
| 6,209,414 B1 | 4/2001 | Uneme |
| 6,221,007 B1 | 4/2001 | Green |
| 6,221,023 B1 | 4/2001 | Matsuba et al. |
| 6,228,080 B1 | 5/2001 | Gines |
| 6,228,089 B1 | 5/2001 | Wahrburg |
| 6,228,098 B1 | 5/2001 | Kayan et al. |
| 6,237,604 B1 | 5/2001 | Burnside et al. |
| 6,238,384 B1 | 5/2001 | Peer |
| 6,251,485 B1 | 6/2001 | Harris et al. |
| 6,254,534 B1 | 7/2001 | Butler et al. |
| 6,254,619 B1 | 7/2001 | Garabet et al. |
| 6,254,642 B1 | 7/2001 | Taylor |
| 6,261,679 B1 | 7/2001 | Chen et al. |
| 6,264,617 B1 | 7/2001 | Bales et al. |
| 6,270,916 B1 | 8/2001 | Sink et al. |
| 6,280,407 B1 | 8/2001 | Manna et al. |
| 6,293,927 B1 | 9/2001 | McGuckin, Jr. |
| 6,302,743 B1 | 10/2001 | Chiu et al. |
| 6,306,424 B1 | 10/2001 | Vyakarnam et al. |
| 6,309,397 B1 | 10/2001 | Julian et al. |
| 6,312,435 B1 | 11/2001 | Wallace et al. |
| 6,319,510 B1 | 11/2001 | Yates |
| 6,325,805 B1 | 12/2001 | Ogilvie et al. |
| 6,328,498 B1 | 12/2001 | Mersch |
| 6,348,061 B1 | 2/2002 | Whitman |
| D454,951 S | 3/2002 | Bon |
| 6,358,263 B2 | 3/2002 | Mark et al. |
| 6,358,459 B1 | 3/2002 | Ziegler et al. |
| 6,371,114 B1 | 4/2002 | Schmidt et al. |
| 6,377,011 B1 | 4/2002 | Ben-Ur |
| 6,387,092 B1 | 5/2002 | Burnside et al. |
| 6,394,998 B1 | 5/2002 | Wallace et al. |
| 6,398,779 B1 | 6/2002 | Buysse et al. |
| 6,412,639 B1 | 7/2002 | Hickey |
| 6,428,487 B1 | 8/2002 | Burdorff et al. |
| D462,758 S | 9/2002 | Epstein et al. |
| 6,445,530 B1 | 9/2002 | Baker |
| 6,447,523 B1 | 9/2002 | Middleman et al. |
| 6,447,799 B1 | 9/2002 | Ullman |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,286 B2 | 10/2002 | Mastri et al. |
| 6,482,217 B1 | 11/2002 | Pintor et al. |
| 6,485,503 B2 | 11/2002 | Jacobs et al. |
| 6,486,286 B1 | 11/2002 | McGall et al. |
| 6,488,659 B1 | 12/2002 | Rosenman |
| 6,494,885 B1 | 12/2002 | Dhindsa |
| 6,503,139 B2 | 1/2003 | Coral |
| 6,506,197 B1 | 1/2003 | Rollero et al. |
| 6,514,252 B2 | 2/2003 | Nezhat et al. |
| 6,516,073 B1 | 2/2003 | Schulz et al. |
| 6,520,971 B1 | 2/2003 | Perry et al. |
| 6,520,972 B2 | 2/2003 | Peters |
| 6,524,180 B1 | 2/2003 | Simms et al. |
| 6,532,958 B1 | 3/2003 | Buan et al. |
| 6,533,723 B1 | 3/2003 | Lockery et al. |
| 6,539,816 B2 | 4/2003 | Kogiso et al. |
| 6,558,429 B2 | 5/2003 | Taylor |
| 6,561,187 B2 | 5/2003 | Schmidt et al. |
| 6,582,364 B2 | 6/2003 | Butler et al. |
| 6,585,664 B2 | 7/2003 | Burdorff et al. |
| 6,589,118 B1 | 7/2003 | Soma et al. |
| 6,594,552 B1 | 7/2003 | Nowlin et al. |
| 6,599,323 B2 | 7/2003 | Melican et al. |
| 6,603,050 B2 | 8/2003 | Heaton |
| 6,605,911 B2 | 8/2003 | Klesing |
| 6,620,111 B2 | 9/2003 | Stephens et al. |
| 6,625,517 B1 | 9/2003 | Bogdanov et al. |
| 6,648,901 B2 | 11/2003 | Fleischman et al. |
| 6,659,940 B2 | 12/2003 | Adler |
| 6,670,806 B2 | 12/2003 | Wendt et al. |
| 6,677,687 B2 | 1/2004 | Ho et al. |
| 6,682,544 B2 | 1/2004 | Mastri et al. |

(56) References Cited

U.S. PATENT DOCUMENTS

| | | |
|---|---|---|
| 6,685,698 B2 | 2/2004 | Morley et al. |
| 6,696,814 B2 | 2/2004 | Henderson et al. |
| 6,699,177 B1 | 3/2004 | Wang et al. |
| 6,699,214 B2 | 3/2004 | Gellman |
| 6,720,734 B2 | 4/2004 | Norris |
| 6,722,550 B1 | 4/2004 | Ricordi et al. |
| 6,723,109 B2 | 4/2004 | Solingen |
| 6,743,230 B2 | 6/2004 | Lutze et al. |
| 6,744,385 B2 | 6/2004 | Kazuya et al. |
| 6,747,300 B2 | 6/2004 | Nadd et al. |
| 6,749,600 B1 | 6/2004 | Levy |
| 6,754,959 B1 | 6/2004 | Guiette, III et al. |
| 6,755,843 B2 | 6/2004 | Chung et al. |
| 6,756,705 B2 | 6/2004 | Pulford, Jr. |
| 6,766,957 B2 | 7/2004 | Matsuura et al. |
| 6,793,669 B2 | 9/2004 | Nakamura et al. |
| 6,796,921 B1 | 9/2004 | Buck et al. |
| 6,802,822 B1 | 10/2004 | Dodge |
| 6,802,844 B2 | 10/2004 | Ferree |
| 6,810,359 B2 | 10/2004 | Sakaguchi |
| 6,836,611 B2 | 12/2004 | Popovic et al. |
| 6,841,967 B2 | 1/2005 | Kim et al. |
| 6,847,190 B2 | 1/2005 | Schaefer et al. |
| 6,852,122 B2 | 2/2005 | Rush |
| 6,852,330 B2 | 2/2005 | Bowman et al. |
| 6,859,882 B2 | 2/2005 | Fung |
| D502,994 S | 3/2005 | Blake, III |
| 6,861,954 B2 | 3/2005 | Levin |
| 6,863,668 B2 | 3/2005 | Gillespie et al. |
| 6,884,392 B2 | 4/2005 | Malkin et al. |
| 6,884,428 B2 | 4/2005 | Binette et al. |
| 6,887,710 B2 | 5/2005 | Call et al. |
| 6,894,140 B2 | 5/2005 | Roby |
| 6,899,593 B1 | 5/2005 | Moeller et al. |
| 6,923,819 B2 | 8/2005 | Meade et al. |
| 6,928,902 B1 | 8/2005 | Eyssallenne |
| D509,297 S | 9/2005 | Wells |
| D509,589 S | 9/2005 | Wells |
| 6,942,674 B2 | 9/2005 | Belef et al. |
| 6,951,562 B2 | 10/2005 | Zwirnmann |
| 6,953,461 B2 | 10/2005 | McClurken et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,974,435 B2 | 12/2005 | Daw et al. |
| 6,989,034 B2 | 1/2006 | Hammer et al. |
| 6,990,731 B2 | 1/2006 | Haytayan |
| 6,993,200 B2 | 1/2006 | Tastl et al. |
| 6,996,433 B2 | 2/2006 | Burbank et al. |
| 6,997,935 B2 | 2/2006 | Anderson et al. |
| 7,000,911 B2 | 2/2006 | McCormick et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,014,640 B2 | 3/2006 | Kemppainen et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,775 B2 | 4/2006 | Gadberry et al. |
| 7,028,570 B2 | 4/2006 | Ohta et al. |
| 7,030,904 B2 | 4/2006 | Adair et al. |
| 7,035,716 B2 | 4/2006 | Harris et al. |
| 7,035,762 B2 | 4/2006 | Menard et al. |
| 7,037,314 B2 | 5/2006 | Armstrong |
| 7,041,088 B2 | 5/2006 | Nawrocki et al. |
| 7,046,082 B2 | 5/2006 | Komiya et al. |
| 7,052,454 B2 | 5/2006 | Taylor |
| 7,064,509 B1 | 6/2006 | Fu et al. |
| 7,083,626 B2 | 8/2006 | Hart et al. |
| 7,087,049 B2 | 8/2006 | Nowlin et al. |
| 7,091,412 B2 | 8/2006 | Wang et al. |
| 7,094,916 B2 | 8/2006 | DeLuca et al. |
| 7,096,972 B2 | 8/2006 | Orozco, Jr. |
| 7,101,187 B1 | 9/2006 | Deconinck et al. |
| 7,111,768 B2 | 9/2006 | Cummins et al. |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,119,534 B2 | 10/2006 | Butzmann |
| 7,121,773 B2 | 10/2006 | Mikiya et al. |
| 7,125,403 B2 | 10/2006 | Julian et al. |
| 7,135,027 B2 | 11/2006 | Delmotte |
| 7,141,055 B2 | 11/2006 | Abrams et al. |
| 7,146,191 B2 | 12/2006 | Kerner et al. |
| 7,147,648 B2 | 12/2006 | Lin |
| 7,161,580 B2 | 1/2007 | Bailey et al. |
| 7,163,563 B2 | 1/2007 | Schwartz et al. |
| 7,170,910 B2 | 1/2007 | Chen et al. |
| 7,172,615 B2 | 2/2007 | Morriss et al. |
| 7,174,636 B2 | 2/2007 | Lowe |
| 7,187,960 B2 | 3/2007 | Abreu |
| 7,190,147 B2 | 3/2007 | Gileff et al. |
| 7,196,911 B2 | 3/2007 | Takano et al. |
| D541,418 S | 4/2007 | Schechter et al. |
| 7,202,576 B1 | 4/2007 | Dechene et al. |
| 7,204,404 B2 | 4/2007 | Nguyen et al. |
| 7,225,959 B2 | 6/2007 | Patton et al. |
| 7,226,450 B2 | 6/2007 | Athanasiou et al. |
| 7,229,408 B2 | 6/2007 | Douglas et al. |
| 7,235,072 B2 | 6/2007 | Sartor et al. |
| 7,239,657 B1 | 7/2007 | Gunnarsson |
| 7,241,289 B2 | 7/2007 | Braun |
| 7,252,641 B2 | 8/2007 | Thompson et al. |
| 7,255,012 B2 | 8/2007 | Hedtke |
| 7,267,677 B2 | 9/2007 | Johnson et al. |
| 7,272,002 B2 | 9/2007 | Drapeau |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,289,139 B2 | 10/2007 | Amling et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,336,045 B2 | 2/2008 | Clermonts |
| 7,337,774 B2 | 3/2008 | Webb |
| 7,338,505 B2 | 3/2008 | Belson |
| 7,346,406 B2 | 3/2008 | Brotto et al. |
| 7,348,875 B2 | 3/2008 | Hughes et al. |
| 7,361,168 B2 | 4/2008 | Makower et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,384,403 B2 | 6/2008 | Sherman |
| 7,394,190 B2 | 7/2008 | Huang |
| 7,398,707 B2 | 7/2008 | Morley et al. |
| 7,400,107 B2 | 7/2008 | Schneider et al. |
| 7,401,000 B2 | 7/2008 | Nakamura |
| 7,404,449 B2 | 7/2008 | Bermingham et al. |
| 7,408,310 B2 | 8/2008 | Hong et al. |
| 7,410,085 B2 | 8/2008 | Wolf et al. |
| 7,410,483 B2 | 8/2008 | Danitz et al. |
| 7,419,321 B2 | 9/2008 | Tereschouk |
| D578,644 S | 10/2008 | Shumer et al. |
| 7,435,249 B2 | 10/2008 | Buysse et al. |
| 7,464,845 B2 | 12/2008 | Chou |
| 7,473,221 B2 | 1/2009 | Ewers et al. |
| 7,485,124 B2 | 2/2009 | Kuhns et al. |
| 7,489,055 B2 | 2/2009 | Jeong et al. |
| 7,491,232 B2 | 2/2009 | Bolduc et al. |
| 7,510,534 B2 | 3/2009 | Burdorff et al. |
| 7,513,407 B1 | 4/2009 | Chang |
| 7,527,632 B2 | 5/2009 | Houghton et al. |
| 7,553,275 B2 | 6/2009 | Padget et al. |
| 7,554,343 B2 | 6/2009 | Bromfield |
| 7,561,637 B2 | 7/2009 | Jonsson et al. |
| 7,563,269 B2 | 7/2009 | Hashiguchi |
| 7,578,825 B2 | 8/2009 | Huebner |
| 7,586,289 B2 | 9/2009 | Andruk et al. |
| 7,593,766 B2 | 9/2009 | Faber et al. |

(56) References Cited

U.S. PATENT DOCUMENTS

| | | |
|---|---|---|
| 7,597,699 B2 | 10/2009 | Rogers |
| 7,598,972 B2 | 10/2009 | Tomita |
| 7,604,668 B2 | 10/2009 | Farnsworth et al. |
| 7,630,841 B2 | 12/2009 | Comisky et al. |
| 7,635,922 B2 | 12/2009 | Becker |
| 7,641,671 B2 | 1/2010 | Crainich |
| 7,648,457 B2 | 1/2010 | Stefanchik et al. |
| 7,655,004 B2 | 2/2010 | Long |
| 7,655,584 B2 | 2/2010 | Biran et al. |
| 7,658,705 B2 | 2/2010 | Melvin et al. |
| 7,682,686 B2 | 3/2010 | Curro et al. |
| 7,694,864 B2 | 4/2010 | Okada et al. |
| 7,705,559 B2 | 4/2010 | Powell et al. |
| 7,708,182 B2 | 5/2010 | Viola |
| 7,713,190 B2 | 5/2010 | Brock et al. |
| 7,714,334 B2 | 5/2010 | Lin |
| 7,717,873 B2 | 5/2010 | Swick |
| 7,717,915 B2 | 5/2010 | Miyazawa |
| 7,725,214 B2 | 5/2010 | Diolaiti |
| 7,726,171 B2 | 6/2010 | Langlotz et al. |
| 7,728,553 B2 | 6/2010 | Carrier et al. |
| 7,736,254 B2 | 6/2010 | Schena |
| 7,736,306 B2 | 6/2010 | Brustad et al. |
| 7,747,146 B2 | 6/2010 | Milano et al. |
| 7,748,632 B2 | 7/2010 | Coleman et al. |
| 7,757,924 B2 | 7/2010 | Gerbi et al. |
| 7,762,462 B2 | 7/2010 | Gelbman |
| 7,762,998 B2 | 7/2010 | Birk et al. |
| 7,770,658 B2 | 8/2010 | Ito et al. |
| 7,772,725 B2 | 8/2010 | Siman-Tov |
| 7,775,972 B2 | 8/2010 | Brock et al. |
| 7,779,737 B2 | 8/2010 | Newman, Jr. et al. |
| 7,780,309 B2 | 8/2010 | McMillan et al. |
| 7,806,871 B2 | 10/2010 | Li et al. |
| 7,811,275 B2 | 10/2010 | Birk et al. |
| 7,814,816 B2 | 10/2010 | Alberti et al. |
| 7,815,662 B2 | 10/2010 | Spivey et al. |
| 7,819,799 B2 | 10/2010 | Merril et al. |
| 7,824,422 B2 | 11/2010 | Benchetrit |
| 7,837,425 B2 | 11/2010 | Saeki et al. |
| 7,837,685 B2 | 11/2010 | Weinberg et al. |
| 7,839,109 B2 | 11/2010 | Carmen, Jr. et al. |
| 7,843,158 B2 | 11/2010 | Prisco |
| 7,846,085 B2 | 12/2010 | Silverman et al. |
| 7,850,623 B2 | 12/2010 | Griffin et al. |
| 7,854,735 B2 | 12/2010 | Houser et al. |
| 7,857,184 B2 | 12/2010 | Viola |
| 7,862,502 B2 | 1/2011 | Pool et al. |
| 7,862,546 B2 | 1/2011 | Conlon et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,883,461 B2 | 2/2011 | Albrecht et al. |
| 7,887,536 B2 | 2/2011 | Johnson et al. |
| 7,887,563 B2 | 2/2011 | Cummins |
| 7,892,200 B2 | 2/2011 | Birk et al. |
| 7,896,869 B2 | 3/2011 | DiSilvestro et al. |
| 7,896,897 B2 | 3/2011 | Gresham et al. |
| 7,898,198 B2 | 3/2011 | Murphree |
| 7,900,806 B2 | 3/2011 | Chen et al. |
| 7,901,381 B2 | 3/2011 | Birk et al. |
| 7,905,881 B2 | 3/2011 | Masuda et al. |
| 7,909,039 B2 | 3/2011 | Hur |
| 7,909,224 B2 | 3/2011 | Prommersberger |
| 7,918,845 B2 | 4/2011 | Saadat et al. |
| 7,918,861 B2 | 4/2011 | Brock et al. |
| 7,930,040 B1 | 4/2011 | Kelsch et al. |
| 7,931,877 B2 | 4/2011 | Steffens et al. |
| 7,934,896 B2 | 5/2011 | Schnier |
| 7,936,142 B2 | 5/2011 | Otsuka et al. |
| 7,945,798 B2 | 5/2011 | Carlson et al. |
| 7,946,453 B2 | 5/2011 | Voegele et al. |
| 7,947,011 B2 | 5/2011 | Birk et al. |
| 7,954,685 B2 | 6/2011 | Viola |
| 7,955,253 B2 | 6/2011 | Ewers et al. |
| 7,955,327 B2 | 6/2011 | Sartor et al. |
| 7,963,913 B2 | 6/2011 | Devengenzo et al. |
| 7,966,236 B2 | 6/2011 | Noriega et al. |
| 7,967,791 B2 | 6/2011 | Franer et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,981,132 B2 | 7/2011 | Dubrul et al. |
| 7,988,015 B2 | 8/2011 | Mason, II et al. |
| 7,988,779 B2 | 8/2011 | Disalvo et al. |
| 7,997,054 B2 | 8/2011 | Bertsch et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,513 B2 | 8/2011 | Nalagatla et al. |
| 8,016,849 B2 | 9/2011 | Wenchell |
| 8,025,896 B2 | 9/2011 | Malaviya et al. |
| 8,028,882 B2 | 10/2011 | Viola |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,337 B2 | 10/2011 | Simard |
| 8,035,487 B2 | 10/2011 | Malackowski |
| 8,044,604 B2 | 10/2011 | Hagino et al. |
| 8,052,636 B2 | 11/2011 | Moll et al. |
| 8,061,014 B2 | 11/2011 | Smith et al. |
| 8,062,236 B2 | 11/2011 | Soltz |
| 8,066,158 B2 | 11/2011 | Vogel et al. |
| 8,066,166 B2 | 11/2011 | Demmy et al. |
| 8,066,720 B2 | 11/2011 | Knodel et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,079,989 B2 | 12/2011 | Birk et al. |
| 8,084,969 B2 | 12/2011 | David et al. |
| 8,091,753 B2 | 1/2012 | Viola |
| 8,093,572 B2 | 1/2012 | Kuduvalli |
| 8,100,824 B2 | 1/2012 | Hegeman et al. |
| 8,108,033 B2 | 1/2012 | Drew et al. |
| 8,113,408 B2 | 2/2012 | Wenchell et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,123,523 B2 | 2/2012 | Carron et al. |
| 8,128,662 B2 | 3/2012 | Altarac et al. |
| 8,132,705 B2 | 3/2012 | Viola et al. |
| 8,136,711 B2 | 3/2012 | Beardsley et al. |
| 8,142,200 B2 | 3/2012 | Crunkilton et al. |
| 8,142,461 B2 | 3/2012 | Houser et al. |
| 8,142,515 B2 | 3/2012 | Therin et al. |
| 8,143,520 B2 | 3/2012 | Cutler |
| 8,147,421 B2 | 4/2012 | Farquhar et al. |
| 8,147,456 B2 | 4/2012 | Fisher et al. |
| 8,152,756 B2 | 4/2012 | Webster et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,622 B2 | 5/2012 | Zhou |
| 8,177,776 B2 | 5/2012 | Humayun et al. |
| 8,181,839 B2 | 5/2012 | Beetel |
| 8,182,422 B2 | 5/2012 | Bayer et al. |
| 8,183,807 B2 | 5/2012 | Tsai et al. |
| 8,186,556 B2 | 5/2012 | Viola |
| 8,186,558 B2 | 5/2012 | Sapienza |
| 8,192,651 B2 | 6/2012 | Young et al. |
| 8,197,837 B2 | 6/2012 | Jamiolkowski et al. |
| 8,202,549 B2 | 6/2012 | Stucky et al. |
| 8,210,721 B2 | 7/2012 | Chen et al. |
| 8,215,532 B2 | 7/2012 | Marczyk |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,229,549 B2 | 7/2012 | Whitman et al. |
| 8,235,272 B2 | 8/2012 | Nicholas et al. |
| 8,236,020 B2 | 8/2012 | Smith et al. |

(56) References Cited

U.S. PATENT DOCUMENTS

| | | |
|---|---|---|
| 8,237,388 B2 | 8/2012 | Jinno et al. |
| 8,240,537 B2 | 8/2012 | Marczyk |
| 8,241,284 B2 | 8/2012 | Dycus et al. |
| 8,246,608 B2 | 8/2012 | Omori et al. |
| 8,257,386 B2 | 9/2012 | Lee et al. |
| 8,257,634 B2 | 9/2012 | Scirica |
| 8,272,918 B2 | 9/2012 | Lam |
| 8,281,446 B2 | 10/2012 | Moskovich |
| 8,285,367 B2 | 10/2012 | Hyde et al. |
| 8,286,846 B2 | 10/2012 | Smith et al. |
| 8,287,487 B2 | 10/2012 | Estes |
| 8,287,522 B2 | 10/2012 | Moses et al. |
| 8,298,189 B2 | 10/2012 | Fisher et al. |
| 8,298,233 B2 | 10/2012 | Mueller |
| 8,308,043 B2 | 11/2012 | Bindra et al. |
| 8,308,725 B2 | 11/2012 | Bell et al. |
| 8,310,188 B2 | 11/2012 | Nakai |
| 8,317,437 B2 | 11/2012 | Merkley et al. |
| 8,317,744 B2 | 11/2012 | Kirschenman |
| 8,322,901 B2 | 12/2012 | Michelotti |
| 8,333,691 B2 | 12/2012 | Schaaf |
| 8,333,779 B2 | 12/2012 | Smith et al. |
| 8,334,468 B2 | 12/2012 | Palmer et al. |
| 8,343,150 B2 | 1/2013 | Artale |
| 8,347,978 B2 | 1/2013 | Forster et al. |
| 8,348,124 B2 | 1/2013 | Scirica |
| 8,348,837 B2 | 1/2013 | Wenchell |
| 8,348,959 B2 | 1/2013 | Wolford et al. |
| 8,349,987 B2 | 1/2013 | Kapiamba et al. |
| 8,352,004 B2 | 1/2013 | Mannheimer et al. |
| 8,357,161 B2 | 1/2013 | Mueller |
| 8,366,787 B2 | 2/2013 | Brown et al. |
| 8,371,393 B2 | 2/2013 | Higuchi et al. |
| 8,371,494 B2 | 2/2013 | Racenet et al. |
| 8,377,029 B2 | 2/2013 | Nagao et al. |
| 8,382,773 B2 | 2/2013 | Whitfield et al. |
| 8,382,790 B2 | 2/2013 | Uenohara et al. |
| 8,387,848 B2 | 3/2013 | Johnson et al. |
| 8,398,669 B2 | 3/2013 | Kim |
| 8,400,851 B2 | 3/2013 | Byun |
| 8,403,946 B2 | 3/2013 | Whitfield et al. |
| 8,403,950 B2 | 3/2013 | Palmer et al. |
| 8,409,175 B2 | 4/2013 | Lee et al. |
| 8,411,500 B2 | 4/2013 | Gapihan et al. |
| 8,413,661 B2 | 4/2013 | Rousseau et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,427,430 B2 | 4/2013 | Lee et al. |
| 8,444,037 B2 | 5/2013 | Nicholas et al. |
| 8,454,495 B2 | 6/2013 | Kawano et al. |
| 8,454,640 B2 | 6/2013 | Johnston et al. |
| 8,459,521 B2 | 6/2013 | Zemlok et al. |
| 8,459,524 B2 | 6/2013 | Pribanic et al. |
| 8,465,475 B2 | 6/2013 | Isbell, Jr. |
| 8,465,515 B2 | 6/2013 | Drew et al. |
| 8,469,946 B2 | 6/2013 | Sugita |
| 8,470,355 B2 | 6/2013 | Skalla et al. |
| 8,475,454 B1 | 7/2013 | Alshemari |
| 8,479,968 B2 | 7/2013 | Hodgkinson et al. |
| 8,485,970 B2 | 7/2013 | Widenhouse et al. |
| 8,487,199 B2 | 7/2013 | Palmer et al. |
| 8,491,603 B2 | 7/2013 | Yeung et al. |
| 8,496,154 B2 | 7/2013 | Marczyk et al. |
| 8,500,721 B2 | 8/2013 | Jinno |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,512,402 B2 | 8/2013 | Marczyk et al. |
| 8,518,024 B2 | 8/2013 | Williams et al. |
| 8,532,747 B2 | 9/2013 | Nock et al. |
| 8,535,340 B2 | 9/2013 | Allen |
| 8,550,984 B2 | 10/2013 | Takemoto |
| 8,555,660 B2 | 10/2013 | Takenaka et al. |
| 8,560,147 B2 | 10/2013 | Taylor et al. |
| 8,561,617 B2 | 10/2013 | Lindh et al. |
| 8,561,871 B2 | 10/2013 | Rajappa et al. |
| 8,562,598 B2 | 10/2013 | Falkenstein et al. |
| 8,568,416 B2 | 10/2013 | Schmitz et al. |
| 8,568,425 B2 | 10/2013 | Ross et al. |
| 8,573,459 B2 | 11/2013 | Smith et al. |
| 8,573,462 B2 | 11/2013 | Smith et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,590,760 B2 | 11/2013 | Cummins et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,608,043 B2 | 12/2013 | Scirica |
| 8,616,427 B2 | 12/2013 | Viola |
| 8,627,993 B2 | 1/2014 | Smith et al. |
| 8,627,995 B2 | 1/2014 | Smith et al. |
| 8,631,993 B2 | 1/2014 | Kostrzewski |
| 8,636,191 B2 | 1/2014 | Meagher |
| 8,636,193 B2 | 1/2014 | Whitman et al. |
| 8,639,936 B2 | 1/2014 | Hu et al. |
| 8,646,674 B2 | 2/2014 | Schulte et al. |
| 8,657,175 B2 | 2/2014 | Sonnenschein et al. |
| 8,657,814 B2 | 2/2014 | Werneth et al. |
| 8,657,821 B2 | 2/2014 | Palermo |
| 8,663,106 B2 | 3/2014 | Stivoric et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,672,922 B2 | 3/2014 | Loh et al. |
| 8,672,935 B2 | 3/2014 | Okada et al. |
| 8,672,951 B2 | 3/2014 | Smith et al. |
| 8,675,820 B2 | 3/2014 | Baic et al. |
| 8,679,154 B2 | 3/2014 | Smith et al. |
| 8,679,156 B2 | 3/2014 | Smith et al. |
| 8,684,248 B2 | 4/2014 | Milliman |
| 8,684,249 B2 | 4/2014 | Racenet et al. |
| 8,684,962 B2 | 4/2014 | Kirschenman et al. |
| 8,685,004 B2 | 4/2014 | Zemlock et al. |
| 8,708,210 B2 | 4/2014 | Zemlok et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,302 B2 | 5/2014 | Ibrahim et al. |
| 8,727,199 B2 | 5/2014 | Wenchell |
| 8,727,961 B2 | 5/2014 | Ziv |
| 8,728,099 B2 | 5/2014 | Cohn et al. |
| 8,733,470 B2 | 5/2014 | Matthias et al. |
| 8,733,612 B2 | 5/2014 | Ma |
| 8,734,336 B2 | 5/2014 | Bonadio et al. |
| 8,734,359 B2 | 5/2014 | Ibanez et al. |
| 8,747,441 B2 | 6/2014 | Konieczynski et al. |
| 8,752,748 B2 | 6/2014 | Whitman et al. |
| 8,757,287 B2 | 6/2014 | Mak et al. |
| 8,758,366 B2 | 6/2014 | McLean et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,777,082 B2 | 7/2014 | Scirica |
| 8,777,083 B2 | 7/2014 | Racenet et al. |
| 8,777,898 B2 | 7/2014 | Suon et al. |
| 8,784,304 B2 | 7/2014 | Mikkaichi et al. |
| 8,790,658 B2 | 7/2014 | Cigarini et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |

(56) References Cited

U.S. PATENT DOCUMENTS

| | | |
|---|---|---|
| 8,800,840 B2 | 8/2014 | Jankowski |
| 8,801,801 B2 | 8/2014 | Datta et al. |
| 8,808,161 B2 | 8/2014 | Gregg et al. |
| 8,808,274 B2 | 8/2014 | Hartwell |
| 8,808,325 B2 | 8/2014 | Hess et al. |
| 8,811,017 B2 | 8/2014 | Fujii et al. |
| 8,825,164 B2 | 9/2014 | Tweden et al. |
| 8,827,134 B2 | 9/2014 | Viola et al. |
| 8,833,219 B2 | 9/2014 | Pierce |
| 8,833,630 B2 | 9/2014 | Milliman |
| 8,834,498 B2 | 9/2014 | Byrum et al. |
| 8,840,609 B2 | 9/2014 | Stuebe |
| 8,851,215 B2 | 10/2014 | Goto |
| 8,852,185 B2 | 10/2014 | Twomey |
| 8,858,538 B2 | 10/2014 | Belson et al. |
| 8,864,010 B2 | 10/2014 | Williams |
| 8,870,912 B2 | 10/2014 | Brisson et al. |
| 8,876,858 B2 | 11/2014 | Braun |
| 8,887,979 B2 | 11/2014 | Mastri et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,905,287 B2 | 12/2014 | Racenet et al. |
| 8,910,846 B2 | 12/2014 | Viola |
| 8,911,448 B2 | 12/2014 | Stein |
| 8,911,460 B2 | 12/2014 | Neurohr et al. |
| 8,920,433 B2 | 12/2014 | Barrier et al. |
| 8,920,435 B2 | 12/2014 | Smith et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,926,506 B2 | 1/2015 | Widenhouse et al. |
| 8,931,679 B2 | 1/2015 | Kostrzewski |
| 8,931,680 B2 | 1/2015 | Milliman |
| 8,945,163 B2 | 2/2015 | Voegele et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,963,714 B2 | 2/2015 | Medhal et al. |
| 8,967,444 B2 | 3/2015 | Beetel |
| 8,967,448 B2 | 3/2015 | Carter et al. |
| 8,968,355 B2 | 3/2015 | Malkowski et al. |
| 8,968,358 B2 | 3/2015 | Reschke |
| 8,973,805 B2 | 3/2015 | Scirica et al. |
| 8,974,440 B2 | 3/2015 | Farritor et al. |
| 8,974,932 B2 | 3/2015 | McGahan et al. |
| 8,979,843 B2 | 3/2015 | Timm et al. |
| 8,991,678 B2 | 3/2015 | Wellman et al. |
| 8,992,042 B2 | 3/2015 | Eichenholz |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,002,518 B2 | 4/2015 | Manzo et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,016,541 B2 | 4/2015 | Viola et al. |
| 9,016,545 B2 | 4/2015 | Aranyi et al. |
| 9,017,355 B2 | 4/2015 | Smith et al. |
| 9,017,369 B2 | 4/2015 | Renger et al. |
| 9,021,684 B2 | 5/2015 | Lenker et al. |
| 9,023,071 B2 | 5/2015 | Miller et al. |
| 9,030,169 B2 | 5/2015 | Christensen et al. |
| 9,034,505 B2 | 5/2015 | Detry et al. |
| 9,039,694 B2 | 5/2015 | Ross et al. |
| 9,044,229 B2 | 6/2015 | Scheib et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,055,942 B2 | 6/2015 | Balbierz et al. |
| 9,055,943 B2 | 6/2015 | Zemlok et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,523 B2 | 7/2015 | Houser et al. |
| 9,089,326 B2 | 7/2015 | Krumanaker et al. |
| 9,089,352 B2 | 7/2015 | Jeong |
| 9,091,588 B2 | 7/2015 | Lefler |
| 9,095,346 B2 | 8/2015 | Houser et al. |
| 9,101,475 B2 | 8/2015 | Wei et al. |
| 9,107,690 B2 | 8/2015 | Bales, Jr. et al. |
| 9,110,587 B2 | 8/2015 | Kim et al. |
| 9,113,876 B2 | 8/2015 | Zemlok et al. |
| 9,113,881 B2 | 8/2015 | Scirica |
| 9,113,887 B2 | 8/2015 | Behnke, II et al. |
| 9,119,898 B2 | 9/2015 | Bayon et al. |
| 9,119,957 B2 | 9/2015 | Gantz et al. |
| 9,131,835 B2 | 9/2015 | Widenhouse et al. |
| 9,131,950 B2 | 9/2015 | Matthew |
| 9,138,226 B2 | 9/2015 | Racenet et al. |
| 9,144,455 B2 | 9/2015 | Kennedy et al. |
| 9,153,994 B2 | 10/2015 | Wood et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,221 B2 | 11/2015 | Burbank |
| 9,192,430 B2 | 11/2015 | Rachlin et al. |
| 9,192,434 B2 | 11/2015 | Twomey et al. |
| 9,198,642 B2 | 12/2015 | Storz |
| 9,198,644 B2 | 12/2015 | Balek et al. |
| 9,204,830 B2 | 12/2015 | Zand et al. |
| 9,204,923 B2 | 12/2015 | Manzo et al. |
| 9,204,924 B2 | 12/2015 | Marczyk et al. |
| 9,216,013 B2 | 12/2015 | Scirica et al. |
| 9,216,030 B2 | 12/2015 | Fan et al. |
| 9,216,062 B2 | 12/2015 | Duque et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| 9,233,610 B2 | 1/2016 | Kim et al. |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,241,712 B2 | 1/2016 | Zemlok et al. |
| 9,241,716 B2 | 1/2016 | Whitman |
| 9,241,731 B2 | 1/2016 | Boudreaux et al. |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,282,963 B2 | 3/2016 | Bryant |
| 9,283,028 B2 | 3/2016 | Johnson |
| 9,289,211 B2 | 3/2016 | Williams et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,307,987 B2 | 4/2016 | Swensgard et al. |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,646 B2 | 4/2016 | Lim et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,326,788 B2 | 5/2016 | Batross et al. |
| 9,326,812 B2 | 5/2016 | Waaler et al. |
| 9,333,040 B2 | 5/2016 | Shellenberger et al. |
| 9,333,082 B2 | 5/2016 | Wei et al. |

(56) References Cited

U.S. PATENT DOCUMENTS

| | | |
|---|---|---|
| 9,339,226 B2 | 5/2016 | van der Walt et al. |
| 9,345,480 B2 | 5/2016 | Hessler et al. |
| 9,351,728 B2 | 5/2016 | Sniffin et al. |
| 9,351,731 B2 | 5/2016 | Carter et al. |
| 9,351,732 B2 | 5/2016 | Hodgkinson |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,226 B2 | 6/2016 | Zemlok et al. |
| 9,364,229 B2 | 6/2016 | D'Agostino et al. |
| 9,364,231 B2 | 6/2016 | Wenchell |
| 9,368,991 B2 | 6/2016 | Qahouq |
| 9,370,341 B2 | 6/2016 | Ceniccola et al. |
| 9,375,255 B2 | 6/2016 | Houser et al. |
| 9,381,058 B2 | 7/2016 | Houser et al. |
| 9,386,985 B2 | 7/2016 | Koch, Jr. et al. |
| 9,387,003 B2 | 7/2016 | Kaercher et al. |
| 9,393,018 B2 | 7/2016 | Wang et al. |
| 9,402,604 B2 | 8/2016 | Williams et al. |
| 9,402,627 B2 | 8/2016 | Stevenson et al. |
| 9,408,622 B2 | 8/2016 | Stulen et al. |
| 9,411,370 B2 | 8/2016 | Benni et al. |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,427,223 B2 | 8/2016 | Park et al. |
| 9,427,231 B2 | 8/2016 | Racenet et al. |
| 9,433,411 B2 | 9/2016 | Racenet et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,461,340 B2 | 10/2016 | Li et al. |
| 9,463,040 B2 | 10/2016 | Jeong et al. |
| 9,463,260 B2 | 10/2016 | Stopek |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,480,492 B2 | 11/2016 | Aranyi et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,521 B2 | 11/2016 | Deutmeyer et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,532,783 B2 | 1/2017 | Swayze et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,626 B2 | 4/2017 | Soltz et al. |
| 9,629,652 B2 | 4/2017 | Mumaw et al. |
| 9,629,814 B2 | 4/2017 | Widenhouse et al. |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |

(56) References Cited

U.S. PATENT DOCUMENTS

| | | |
|---|---|---|
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,724,091 B2 | 8/2017 | Shelton, IV et al. |
| 9,724,092 B2 | 8/2017 | Baxter, III et al. |
| 9,724,096 B2 | 8/2017 | Thompson et al. |
| 9,724,098 B2 | 8/2017 | Baxter, III et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,639 B2 | 9/2017 | Barnes et al. |
| 9,757,126 B2 | 9/2017 | Cappola |
| 9,757,129 B2 | 9/2017 | Williams |
| 9,757,130 B2 | 9/2017 | Shelton, IV |
| 9,763,662 B2 | 9/2017 | Shelton, IV et al. |
| D800,904 S | 10/2017 | Leimbach et al. |
| 9,775,609 B2 | 10/2017 | Shelton, IV et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,782,170 B2 | 10/2017 | Zemlok et al. |
| 9,782,180 B2 | 10/2017 | Smith et al. |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,847 B2 | 10/2017 | Jinno |
| 9,788,851 B2 | 10/2017 | Dannaher et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |

(56) References Cited

U.S. PATENT DOCUMENTS

| | | |
|---|---|---|
| 9,974,539 B2 | 5/2018 | Yates et al. |
| 9,980,713 B2 | 5/2018 | Aronhalt et al. |
| 9,980,729 B2 | 5/2018 | Moore et al. |
| 9,987,003 B2 | 6/2018 | Timm et al. |
| 9,987,099 B2 | 6/2018 | Chen et al. |
| 10,004,500 B2 | 6/2018 | Shelton, IV et al. |
| 10,004,506 B2 | 6/2018 | Shelton, IV et al. |
| 10,022,125 B2 | 7/2018 | (Prommersberger) Stopek et al. |
| 10,024,407 B2 | 7/2018 | Aranyi et al. |
| 10,029,125 B2 | 7/2018 | Shapiro et al. |
| 10,034,668 B2 | 7/2018 | Ebner |
| 10,039,440 B2 | 8/2018 | Fenech et al. |
| 10,039,545 B2 | 8/2018 | Sadowski et al. |
| 10,041,822 B2 | 8/2018 | Zemlok |
| 10,045,778 B2 | 8/2018 | Yates et al. |
| 10,052,164 B2 | 8/2018 | Overmyer |
| 10,058,317 B2 | 8/2018 | Fan et al. |
| 10,064,620 B2 | 9/2018 | Gettinger et al. |
| 10,064,639 B2 | 9/2018 | Ishida et al. |
| 10,064,649 B2 | 9/2018 | Golebieski et al. |
| D831,209 S | 10/2018 | Huitema et al. |
| 10,085,624 B2 | 10/2018 | Isoda et al. |
| 10,085,806 B2 | 10/2018 | Hagn et al. |
| 10,092,292 B2 | 10/2018 | Boudreaux et al. |
| 10,099,303 B2 | 10/2018 | Yoshida et al. |
| 10,105,128 B2 | 10/2018 | Cooper et al. |
| 10,105,136 B2 | 10/2018 | Yates et al. |
| 10,117,653 B2 | 11/2018 | Leimbach et al. |
| 10,117,654 B2 | 11/2018 | Ingmanson et al. |
| 2001/0000531 A1 | 4/2001 | Casscells et al. |
| 2002/0022810 A1 | 2/2002 | Urich |
| 2002/0022861 A1 | 2/2002 | Jacobs et al. |
| 2002/0042620 A1 | 4/2002 | Julian et al. |
| 2002/0091374 A1 | 7/2002 | Cooper |
| 2002/0128633 A1 | 9/2002 | Brock et al. |
| 2002/0158593 A1 | 10/2002 | Henderson et al. |
| 2002/0185514 A1 | 12/2002 | Adams et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0083648 A1 | 5/2003 | Wang et al. |
| 2003/0094356 A1 | 5/2003 | Waldron |
| 2003/0190584 A1 | 10/2003 | Heasley |
| 2003/0212005 A1 | 11/2003 | Petito et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0049121 A1 | 3/2004 | Yaron |
| 2004/0049172 A1 | 3/2004 | Root et al. |
| 2004/0119185 A1 | 6/2004 | Chen |
| 2004/0122423 A1 | 6/2004 | Dycus et al. |
| 2004/0153100 A1 | 8/2004 | Ahlberg et al. |
| 2004/0158261 A1 | 8/2004 | Vu |
| 2004/0166169 A1 | 8/2004 | Malaviya et al. |
| 2004/0197367 A1 | 10/2004 | Rezania et al. |
| 2004/0204735 A1 | 10/2004 | Shiroff et al. |
| 2004/0249366 A1 | 12/2004 | Kunz |
| 2005/0021078 A1 | 1/2005 | Vleugels et al. |
| 2005/0051163 A1 | 3/2005 | Deem et al. |
| 2005/0057225 A1 | 3/2005 | Marquet |
| 2005/0080342 A1 | 4/2005 | Gilreath et al. |
| 2005/0130682 A1 | 6/2005 | Takara et al. |
| 2005/0139636 A1 | 6/2005 | Schwemberger et al. |
| 2005/0145671 A1 | 7/2005 | Viola |
| 2005/0159778 A1 | 7/2005 | Heinrich et al. |
| 2005/0177249 A1 | 8/2005 | Kladakis et al. |
| 2005/0184121 A1 | 8/2005 | Heinrich |
| 2005/0186240 A1 | 8/2005 | Ringeisen et al. |
| 2005/0209614 A1 | 9/2005 | Fenter et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228446 A1 | 10/2005 | Mooradian et al. |
| 2005/0230453 A1 | 10/2005 | Viola |
| 2005/0251063 A1 | 11/2005 | Basude |
| 2005/0274034 A1 | 12/2005 | Hayashida et al. |
| 2006/0052824 A1 | 3/2006 | Ransick et al. |
| 2006/0079879 A1 | 4/2006 | Faller et al. |
| 2006/0111210 A1 | 5/2006 | Hinman |
| 2006/0161050 A1 | 7/2006 | Butler et al. |
| 2006/0176031 A1 | 8/2006 | Forman et al. |
| 2006/0180633 A1 | 8/2006 | Emmons |
| 2006/0199999 A1 | 9/2006 | Ikeda et al. |
| 2006/0261763 A1 | 11/2006 | Iott et al. |
| 2007/0016235 A1 | 1/2007 | Tanaka et al. |
| 2007/0043387 A1 | 2/2007 | Vargas et al. |
| 2007/0055228 A1 | 3/2007 | Berg et al. |
| 2007/0073389 A1 | 3/2007 | Bolduc et al. |
| 2007/0134251 A1 | 6/2007 | Ashkenazi et al. |
| 2007/0175949 A1* | 8/2007 | Shelton, IV ...... A61B 17/07207 227/176.1 |
| 2007/0179477 A1 | 8/2007 | Danger |
| 2007/0197954 A1 | 8/2007 | Keenan |
| 2007/0207010 A1 | 9/2007 | Caspi |
| 2007/0208375 A1 | 9/2007 | Nishizawa et al. |
| 2007/0296286 A1 | 12/2007 | Avenell |
| 2008/0021486 A1 | 1/2008 | Oyola et al. |
| 2008/0042861 A1 | 2/2008 | Dacquay et al. |
| 2008/0064921 A1 | 3/2008 | Larkin et al. |
| 2008/0083807 A1 | 4/2008 | Beardsley et al. |
| 2008/0125749 A1 | 5/2008 | Olson |
| 2008/0135600 A1 | 6/2008 | Hiranuma et al. |
| 2008/0154335 A1 | 6/2008 | Thrope et al. |
| 2008/0196419 A1 | 8/2008 | Dube |
| 2008/0200755 A1 | 8/2008 | Bakos |
| 2008/0200911 A1 | 8/2008 | Long |
| 2008/0200934 A1 | 8/2008 | Fox |
| 2008/0234709 A1 | 9/2008 | Houser |
| 2008/0242939 A1 | 10/2008 | Johnston |
| 2008/0255418 A1* | 10/2008 | Zemlok ................. A61B 17/068 600/118 |
| 2008/0269596 A1 | 10/2008 | Revie et al. |
| 2008/0293910 A1 | 11/2008 | Kapiamba et al. |
| 2008/0312687 A1 | 12/2008 | Blier |
| 2009/0048583 A1 | 2/2009 | Williams et al. |
| 2009/0221993 A1 | 9/2009 | Sohi et al. |
| 2009/0248041 A1 | 10/2009 | Williams et al. |
| 2010/0012703 A1 | 1/2010 | Calabrese et al. |
| 2010/0065604 A1 | 3/2010 | Weng |
| 2010/0094340 A1 | 4/2010 | Stopek et al. |
| 2010/0116519 A1* | 5/2010 | Gareis ................... B25B 23/147 173/176 |
| 2010/0117577 A1* | 5/2010 | Yanagishima ........ H02P 29/032 318/432 |
| 2010/0191262 A1 | 7/2010 | Harris et al. |
| 2010/0256675 A1 | 10/2010 | Romans |
| 2010/0258327 A1 | 10/2010 | Esenwein et al. |
| 2010/0270355 A1* | 10/2010 | Whitman ............. A61B 17/068 227/176.1 |
| 2010/0318085 A1 | 12/2010 | Austin et al. |
| 2011/0030980 A1* | 2/2011 | Ho ........................ B23B 45/008 173/1 |
| 2011/0034910 A1* | 2/2011 | Ross ................ A61B 17/07207 606/1 |
| 2011/0066156 A1 | 3/2011 | McGahan et al. |
| 2011/0087278 A1 | 4/2011 | Viola et al. |
| 2011/0095064 A1 | 4/2011 | Taylor et al. |
| 2011/0101794 A1 | 5/2011 | Schroeder et al. |
| 2011/0112530 A1 | 5/2011 | Keller |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0155781 A1* | 6/2011 | Swensgard ...... A61B 17/07207 227/176.1 |
| 2011/0160725 A1* | 6/2011 | Kabaya ............... A61B 18/1206 606/42 |
| 2011/0167651 A1* | 7/2011 | Tokunaga ............. B23D 47/12 30/388 |
| 2011/0172495 A1 | 7/2011 | Armstrong |
| 2011/0203821 A1* | 8/2011 | Puzio ................... B25B 23/0064 173/1 |

(56) References Cited

U.S. PATENT DOCUMENTS

| | | | |
|---|---|---|---|
| 2011/0204119 A1* | 8/2011 | McCuen | A61B 17/07207 227/175.1 |
| 2011/0218400 A1 | 9/2011 | Ma et al. | |
| 2011/0230713 A1 | 9/2011 | Kleemann et al. | |
| 2011/0238044 A1 | 9/2011 | Main et al. | |
| 2011/0253765 A1* | 10/2011 | Nicholas | A61B 17/07207 227/175.1 |
| 2011/0284256 A1* | 11/2011 | Iwata | B25F 5/00 173/176 |
| 2012/0016467 A1 | 1/2012 | Chen et al. | |
| 2012/0059286 A1 | 3/2012 | Hastings et al. | |
| 2012/0078139 A1 | 3/2012 | Aldridge et al. | |
| 2012/0086276 A1 | 4/2012 | Sawyers | |
| 2012/0095458 A1 | 4/2012 | Cybulski et al. | |
| 2012/0109186 A1 | 5/2012 | Parrott et al. | |
| 2012/0116261 A1 | 5/2012 | Mumaw et al. | |
| 2012/0116266 A1 | 5/2012 | Houser et al. | |
| 2012/0118595 A1 | 5/2012 | Pellenc | |
| 2012/0132286 A1 | 5/2012 | Lim et al. | |
| 2012/0197272 A1 | 8/2012 | Oray et al. | |
| 2012/0211542 A1 | 8/2012 | Racenet | |
| 2012/0223121 A1* | 9/2012 | Viola | A61B 17/072 227/175.1 |
| 2012/0239068 A1 | 9/2012 | Morris et al. | |
| 2012/0248167 A1* | 10/2012 | Flanagan | A61B 17/07207 227/2 |
| 2012/0253328 A1 | 10/2012 | Cunningham et al. | |
| 2012/0303002 A1 | 11/2012 | Chowaniec et al. | |
| 2013/0006227 A1 | 1/2013 | Takashino | |
| 2013/0018400 A1 | 1/2013 | Milton et al. | |
| 2013/0023910 A1 | 1/2013 | Solomon et al. | |
| 2013/0030462 A1 | 1/2013 | Keating et al. | |
| 2013/0096568 A1 | 4/2013 | Justis | |
| 2013/0105552 A1 | 5/2013 | Weir et al. | |
| 2013/0123816 A1 | 5/2013 | Hodgkinson et al. | |
| 2013/0126202 A1 | 5/2013 | Oomori et al. | |
| 2013/0136969 A1 | 5/2013 | Yasui et al. | |
| 2013/0158390 A1 | 6/2013 | Tan et al. | |
| 2013/0172878 A1 | 7/2013 | Smith | |
| 2013/0214025 A1* | 8/2013 | Zemlok | A61B 17/068 227/175.1 |
| 2013/0253480 A1 | 9/2013 | Kimball et al. | |
| 2013/0277410 A1 | 10/2013 | Fernandez et al. | |
| 2013/0317753 A1 | 11/2013 | Kamen et al. | |
| 2013/0327552 A1 | 12/2013 | Lovelass et al. | |
| 2013/0333910 A1 | 12/2013 | Tanimoto et al. | |
| 2013/0334280 A1 | 12/2013 | Krehel et al. | |
| 2014/0012289 A1* | 1/2014 | Snow | A61B 17/07207 606/130 |
| 2014/0012299 A1 | 1/2014 | Stoddard et al. | |
| 2014/0039549 A1 | 2/2014 | Belsky et al. | |
| 2014/0110453 A1* | 4/2014 | Wingardner | A61B 17/07207 227/175.2 |
| 2014/0110456 A1 | 4/2014 | Taylor | |
| 2014/0115229 A1 | 4/2014 | Kothamasu et al. | |
| 2014/0131418 A1 | 5/2014 | Kostrzewski | |
| 2014/0175147 A1 | 6/2014 | Manoux et al. | |
| 2014/0188159 A1 | 7/2014 | Steege | |
| 2014/0207124 A1 | 7/2014 | Aldridge et al. | |
| 2014/0228867 A1 | 8/2014 | Thomas et al. | |
| 2014/0248167 A1 | 9/2014 | Sugimoto et al. | |
| 2014/0249573 A1 | 9/2014 | Arav | |
| 2014/0303660 A1 | 10/2014 | Boyden et al. | |
| 2014/0354199 A1* | 12/2014 | Zeng | H02P 21/0085 318/400.3 |
| 2014/0367445 A1 | 12/2014 | Ingmanson et al. | |
| 2014/0374130 A1 | 12/2014 | Nakamura et al. | |
| 2015/0002089 A1 | 1/2015 | Rejman et al. | |
| 2015/0066000 A1 | 3/2015 | An et al. | |
| 2015/0122870 A1 | 5/2015 | Zemlok et al. | |
| 2015/0148830 A1 | 5/2015 | Stulen et al. | |
| 2015/0150554 A1 | 6/2015 | Soltz | |
| 2015/0222212 A1* | 8/2015 | Iwata | H02P 7/29 318/139 |
| 2015/0223868 A1* | 8/2015 | Brandt | A61B 18/1445 606/40 |
| 2015/0245835 A1 | 9/2015 | Racenet et al. | |
| 2015/0272604 A1 | 10/2015 | Chowaniec et al. | |
| 2015/0297200 A1 | 10/2015 | Fitzsimmons et al. | |
| 2015/0303417 A1 | 10/2015 | Koeder et al. | |
| 2015/0305729 A1 | 10/2015 | Fitzsimmons et al. | |
| 2015/0324317 A1 | 11/2015 | Collins et al. | |
| 2015/0336249 A1 | 11/2015 | Iwata et al. | |
| 2015/0351758 A1 | 12/2015 | Shelton, IV et al. | |
| 2015/0351762 A1 | 12/2015 | Vendely et al. | |
| 2015/0351765 A1 | 12/2015 | Valentine et al. | |
| 2015/0352699 A1* | 12/2015 | Sakai | B25B 21/02 173/181 |
| 2015/0366220 A1 | 12/2015 | Zhang et al. | |
| 2015/0372265 A1 | 12/2015 | Morisaku et al. | |
| 2015/0374360 A1 | 12/2015 | Scheib et al. | |
| 2015/0374361 A1 | 12/2015 | Gettinger et al. | |
| 2015/0374363 A1 | 12/2015 | Laurent, IV et al. | |
| 2015/0374371 A1 | 12/2015 | Richard et al. | |
| 2015/0380187 A1 | 12/2015 | Zergiebel et al. | |
| 2016/0023342 A1 | 1/2016 | Koenig et al. | |
| 2016/0030042 A1 | 2/2016 | Heinrich et al. | |
| 2016/0030103 A1 | 2/2016 | Manwaring et al. | |
| 2016/0073909 A1 | 3/2016 | Zand et al. | |
| 2016/0082161 A1 | 3/2016 | Zilberman et al. | |
| 2016/0089198 A1 | 3/2016 | Arya et al. | |
| 2016/0095585 A1 | 4/2016 | Zergiebel et al. | |
| 2016/0166308 A1 | 6/2016 | Manwaring et al. | |
| 2016/0192977 A1 | 7/2016 | Manwaring et al. | |
| 2016/0235467 A1* | 8/2016 | Godara | A61B 18/1206 |
| 2016/0256159 A1 | 9/2016 | Pinjala et al. | |
| 2016/0278765 A1 | 9/2016 | Shelton, IV et al. | |
| 2016/0278775 A1 | 9/2016 | Shelton, IV et al. | |
| 2016/0310143 A1 | 10/2016 | Bettuchi | |
| 2016/0345976 A1 | 12/2016 | Gonzalez et al. | |
| 2016/0346034 A1 | 12/2016 | Arya et al. | |
| 2016/0354085 A1 | 12/2016 | Shelton, IV et al. | |
| 2016/0367122 A1 | 12/2016 | Ichimura et al. | |
| 2016/0374675 A1 | 12/2016 | Shelton, IV et al. | |
| 2017/0000485 A1 | 1/2017 | Shelton, IV et al. | |
| 2017/0007236 A1 | 1/2017 | Shelton, IV et al. | |
| 2017/0007237 A1 | 1/2017 | Yates et al. | |
| 2017/0007238 A1 | 1/2017 | Yates et al. | |
| 2017/0007239 A1 | 1/2017 | Shelton, IV | |
| 2017/0007241 A1 | 1/2017 | Shelton, IV et al. | |
| 2017/0007242 A1 | 1/2017 | Shelton, IV et al. | |
| 2017/0007243 A1 | 1/2017 | Shelton, IV et al. | |
| 2017/0007244 A1 | 1/2017 | Shelton, IV et al. | |
| 2017/0007245 A1 | 1/2017 | Shelton, IV et al. | |
| 2017/0007246 A1 | 1/2017 | Shelton, IV et al. | |
| 2017/0007247 A1 | 1/2017 | Shelton, IV et al. | |
| 2017/0007248 A1 | 1/2017 | Shelton, IV et al. | |
| 2017/0007249 A1 | 1/2017 | Shelton, IV et al. | |
| 2017/0007250 A1 | 1/2017 | Shelton, IV et al. | |
| 2017/0007251 A1 | 1/2017 | Yates et al. | |
| 2017/0007254 A1 | 1/2017 | Jaworek et al. | |
| 2017/0007255 A1 | 1/2017 | Jaworek et al. | |
| 2017/0007340 A1 | 1/2017 | Swensgard et al. | |
| 2017/0007341 A1 | 1/2017 | Swensgard et al. | |
| 2017/0007347 A1 | 1/2017 | Jaworek et al. | |
| 2017/0014125 A1 | 1/2017 | Shelton, IV et al. | |
| 2017/0049444 A1 | 2/2017 | Schellin et al. | |
| 2017/0049447 A1 | 2/2017 | Barton et al. | |
| 2017/0049448 A1 | 2/2017 | Widenhouse et al. | |
| 2017/0055986 A1 | 3/2017 | Harris et al. | |
| 2017/0055989 A1 | 3/2017 | Shelton, IV et al. | |
| 2017/0086823 A1 | 3/2017 | Leimbach et al. | |
| 2017/0086827 A1 | 3/2017 | Vendely et al. | |
| 2017/0086829 A1 | 3/2017 | Vendely et al. | |
| 2017/0086830 A1 | 3/2017 | Yates et al. | |
| 2017/0086831 A1 | 3/2017 | Shelton, IV et al. | |
| 2017/0086832 A1 | 3/2017 | Harris et al. | |
| 2017/0086835 A1 | 3/2017 | Harris et al. | |
| 2017/0086836 A1 | 3/2017 | Harris et al. | |
| 2017/0086837 A1 | 3/2017 | Vendely et al. | |
| 2017/0086838 A1 | 3/2017 | Harris et al. | |
| 2017/0086839 A1 | 3/2017 | Vendely et al. | |
| 2017/0086840 A1 | 3/2017 | Harris et al. | |

(56) References Cited

U.S. PATENT DOCUMENTS

| | | |
|---|---|---|
| 2017/0086841 A1 | 3/2017 | Vendely et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0086845 A1 | 3/2017 | Vendely et al. |
| 2017/0086936 A1 | 3/2017 | Shelton, IV et al. |
| 2017/0119390 A1 | 5/2017 | Schellin et al. |
| 2017/0119397 A1 | 5/2017 | Harris et al. |
| 2017/0128149 A1 | 5/2017 | Heinrich et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172672 A1 | 6/2017 | Bailey et al. |
| 2017/0182211 A1 | 6/2017 | Raxworthy et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196558 A1 | 7/2017 | Morgan et al. |
| 2017/0196560 A1 | 7/2017 | Leimbach et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0245953 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281167 A1 | 10/2017 | Shelton, IV et al. |
| 2017/0281180 A1 | 10/2017 | Morgan et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296184 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312040 A1 | 11/2017 | Giordano et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0319777 A1 | 11/2017 | Shelton, IV et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348043 A1 | 12/2017 | Wang et al. |
| 2017/0354415 A1 | 12/2017 | Casasanta, Jr. et al. |
| 2017/0360442 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008269 A1 | 1/2018 | Moore et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055510 A1 | 3/2018 | Schmid et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070942 A1 | 3/2018 | Shelton, IV et al. |
| 2018/0070946 A1 | 3/2018 | Shelton, IV et al. |
| 2018/0074535 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0085123 A1 | 3/2018 | Shelton, IV et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |

(56) References Cited

U.S. PATENT DOCUMENTS

| | | |
|---|---|---|
| 2018/0168584 A1 | 6/2018 | Harris et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168649 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0256185 A1 | 9/2018 | Shelton, IV et al. |
| 2018/0271520 A1 | 9/2018 | Shelton, IV et al. |
| 2018/0280020 A1 | 10/2018 | Hess et al. |
| 2018/0280021 A1 | 10/2018 | Timm et al. |
| 2018/0280022 A1 | 10/2018 | Timm et al. |
| 2018/0280023 A1 | 10/2018 | Timm et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303478 A1 | 10/2018 | Yates et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |

FOREIGN PATENT DOCUMENTS

| | | |
|---|---|---|
| CA | 2940510 A1 | 8/2015 |
| CN | 200942099 Y | 9/2007 |
| CN | 101721236 A | 6/2010 |
| CN | 201719298 U | 1/2011 |
| CN | 201879759 U | 6/2011 |
| CN | 202489990 U | 10/2012 |
| CN | 103829983 A | 6/2014 |
| CN | 103981635 A | 8/2014 |
| CN | 102469995 B | 3/2015 |
| EP | 0541950 A1 | 5/1993 |
| EP | 0726632 B1 | 10/2000 |
| EP | 1723914 A1 | 11/2006 |
| EP | 2116196 A2 | 11/2009 |
| EP | 1728475 B1 | 8/2011 |
| EP | 1962711 B1 | 2/2012 |
| EP | 2620117 A1 | 7/2013 |
| EP | 2842500 A1 | 3/2015 |
| EP | 2853220 A1 | 4/2015 |
| EP | 2747235 B1 | 11/2016 |
| EP | 3363378 A1 | 8/2018 |
| GB | 2090534 B | 6/1984 |
| GB | 2426391 A | 11/2006 |
| JP | S63270040 A | 11/1988 |
| JP | H0129503 B2 | 6/1989 |
| JP | H05212039 A | 8/1993 |
| JP | H067357 A | 1/1994 |
| JP | H09-323068 A | 12/1997 |
| JP | H10-200699 A | 7/1998 |
| JP | 2002054903 A | 2/2002 |
| JP | 2009207260 A | 9/2009 |
| JP | 2009226028 A | 10/2009 |
| JP | 2011072574 A | 4/2011 |
| JP | 4722849 B2 | 7/2011 |
| JP | 5154710 B1 | 2/2013 |
| JP | 2014121599 A | 7/2014 |
| JP | 2016-512057 A | 4/2016 |
| RU | 1814161 C | 5/1993 |
| RU | 2161450 C1 | 1/2001 |
| RU | 61122 U1 | 2/2007 |
| SU | 297156 A | 5/1971 |
| SU | 728848 A | 4/1980 |
| WO | WO-2010134913 A1 | 11/2010 |
| WO | WO-2011056458 A1 | 5/2011 |
| WO | WO-2013151888 A1 | 10/2013 |
| WO | WO-2014158882 A2 | 10/2014 |
| WO | WO-2015187107 A1 | 12/2015 |

OTHER PUBLICATIONS

Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].

Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.

* cited by examiner

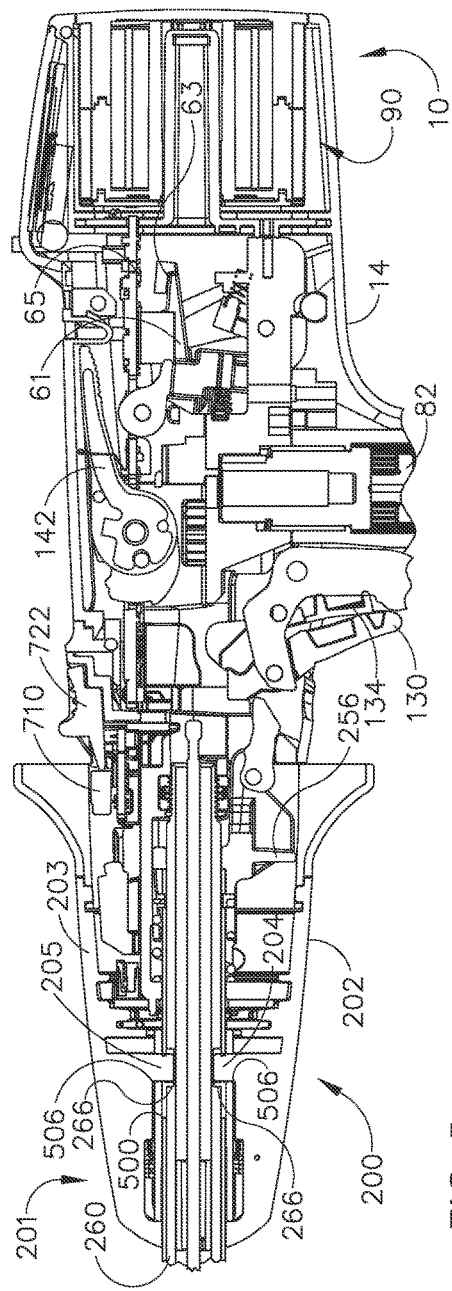
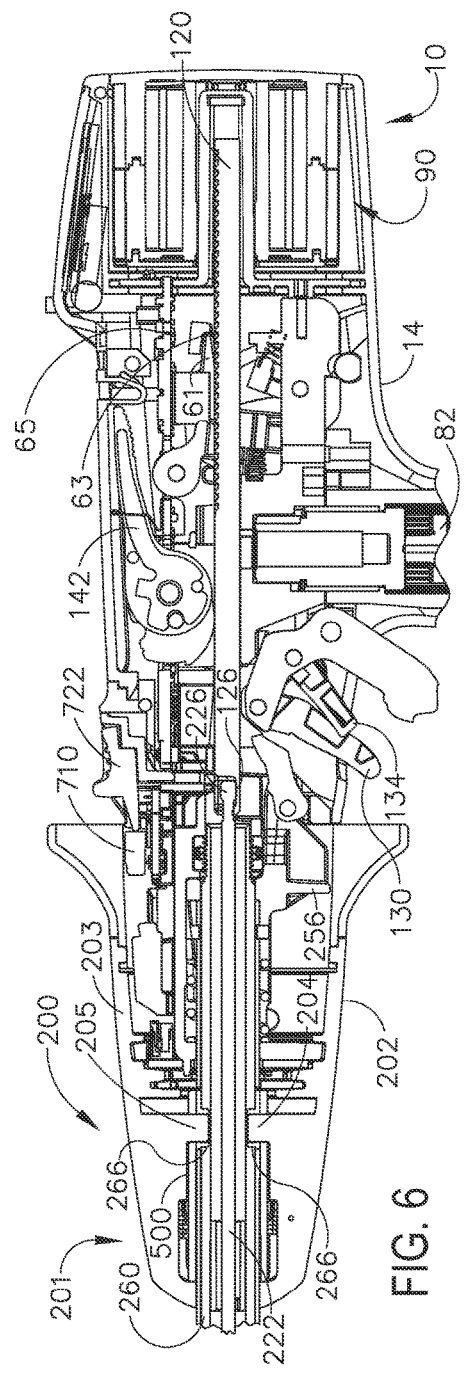
FIG. 5
FIG. 6

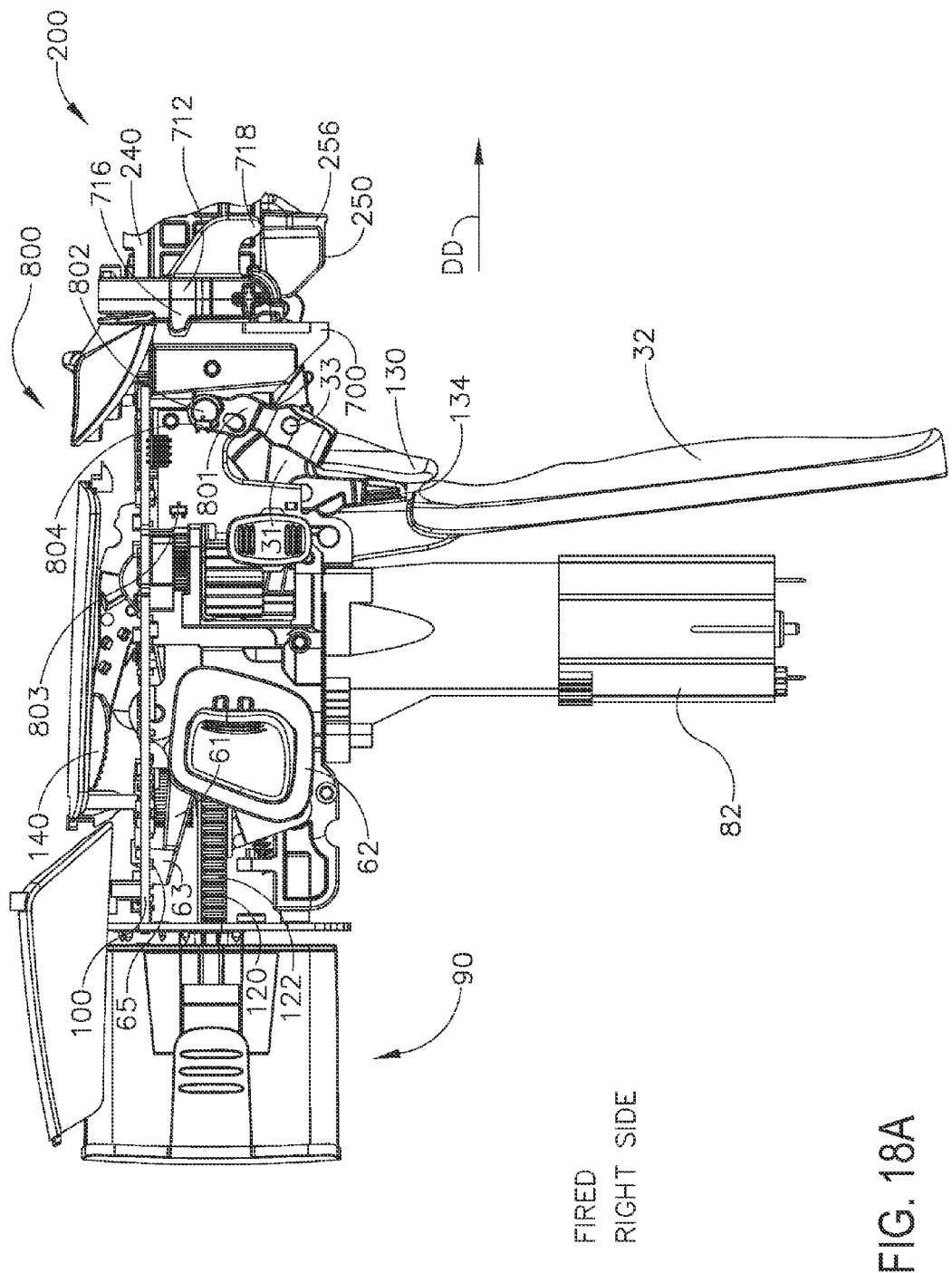

MULTIPLE LEVEL THRESHOLDS TO MODIFY OPERATION OF POWERED SURGICAL INSTRUMENTS

The present disclosure relates to surgical instruments and, in various circumstances, to surgical stapling and cutting instruments and staple cartridges therefor that are designed to staple and cut tissue.

BRIEF DESCRIPTION OF THE DRAWINGS

The features and advantages of the present disclosure, and the manner of attaining them, will become more apparent and the present disclosure will be better understood by reference to the following description of the present disclosure taken in conjunction with the accompanying drawings, wherein:

FIG. 5 is a cross-sectional side view of a portion of the surgical instrument of FIG. 4 with the firing trigger in a fully actuated position;

FIG. 6 is another cross-sectional view of a portion of the surgical instrument of FIG. 5 with the firing trigger in an unactuated position;

FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position;

FIG. 28, which is divided into

DESCRIPTION

Figure 1:
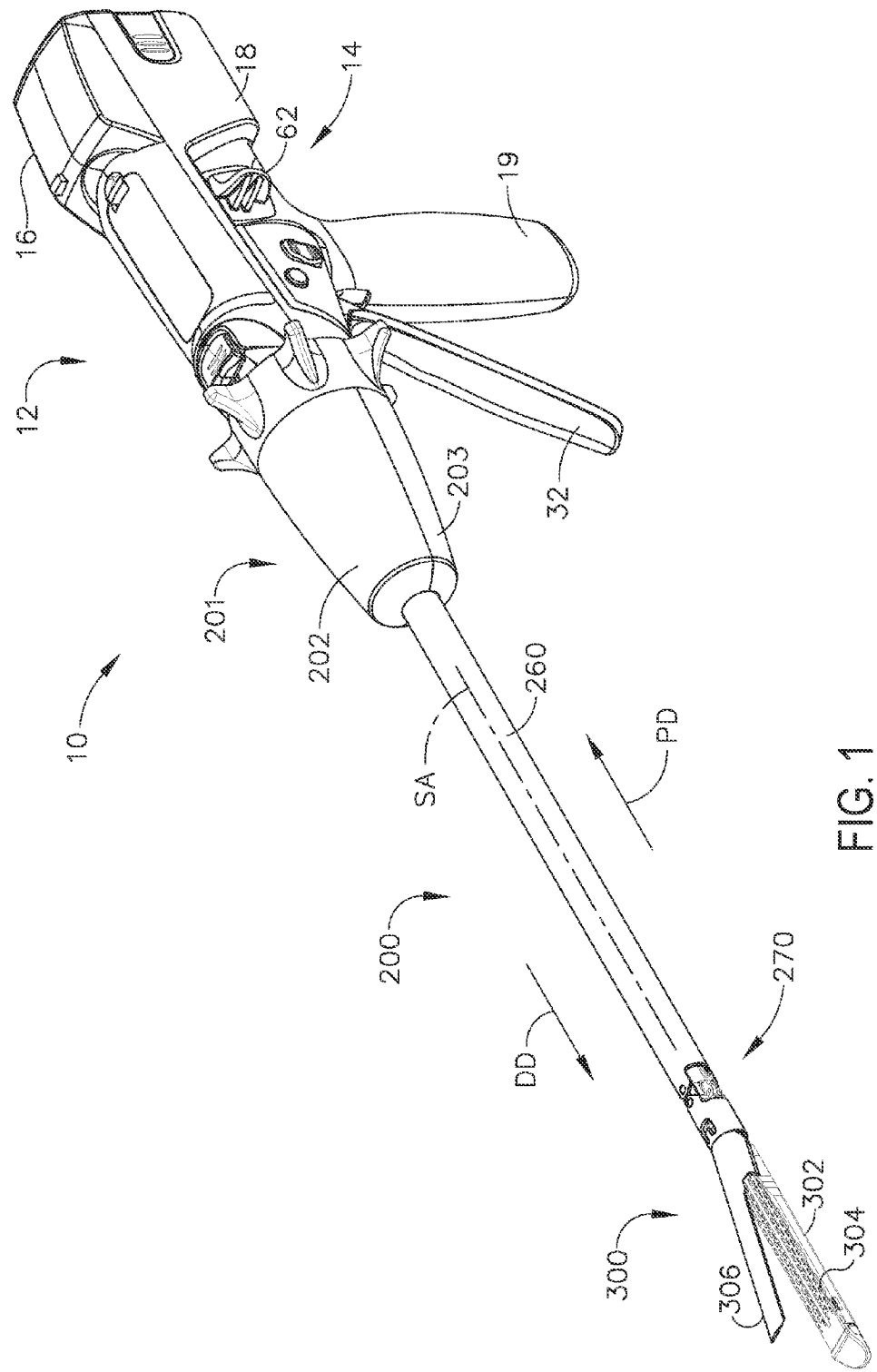
FIG. 1 is a perspective view of a surgical instrument that has an interchangeable shaft assembly operably coupled thereto.

Applicant of the present application owns the following patent applications that were filed on Mar. 6, 2015 and which are each herein incorporated by reference in their respective entireties:

- U.S. patent application Ser. No. 14/640,746, entitled POWERED SURGICAL INSTRUMENT, now U.S. Patent Application Publication No. 2016/0256184;
- U.S. patent application Ser. No. 14/640,832, entitled ADAPTIVE TISSUE COMPRESSION TECHNIQUES TO ADJUST CLOSURE RATES FOR MULTIPLE TISSUE TYPES, 2016/0256154;
- U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;
- U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;
- U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, 2016/0256155;
- U.S. patent application Ser. No. 14/640,837, entitled SMART SENSORS WITH LOCAL SIGNAL PROCESSING, now U.S. Patent Application Publication No. 2016/0256163;
- U.S. patent application Ser. No. 14/640,780, entitled SURGICAL INSTRUMENT COMPRISING A LOCKABLE BATTERY HOUSING, now U.S. Patent Application Publication No. 2016/0256161;
- U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160; and
- U.S. patent application Ser. No. 14/640,799, entitled SIGNAL AND POWER COMMUNICATION SYSTEM POSITIONED ON A ROTATABLE SHAFT, 2016/0256162.

Applicant of the present application owns the following patent applications that were filed on Feb. 27, 2015, and which are each herein incorporated by reference in their respective entireties:

- U.S. patent application Ser. No. 14/633,576, entitled SURGICAL INSTRUMENT SYSTEM COMPRISING AN INSPECTION STATION;
- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;
- U.S. patent application Ser. No. 14/633,560, entitled SURGICAL CHARGING SYSTEM THAT CHARGES AND/OR CONDITIONS ONE OR MORE BATTERIES;
- U.S. patent application Ser. No. 14/633,566, entitled CHARGING SYSTEM THAT ENABLES EMERGENCY RESOLUTIONS FOR CHARGING A BATTERY;
- U.S. patent application Ser. No. 14/633,555, entitled SYSTEM FOR MONITORING WHETHER A SURGICAL INSTRUMENT NEEDS TO BE SERVICED;
- U.S. patent application Ser. No. 14/633,542, entitled REINFORCED BATTERY FOR A SURGICAL INSTRUMENT;
- U.S. patent application Ser. No. 14/633,548, entitled POWER ADAPTER FOR A SURGICAL INSTRUMENT;
- U.S. patent application Ser. No. 14/633,526, entitled ADAPTABLE SURGICAL INSTRUMENT HANDLE;
- U.S. patent application Ser. No. 14/633,541, entitled MODULAR STAPLING ASSEMBLY; and
- U.S. patent application Ser. No. 14/633,562, entitled SURGICAL APPARATUS CONFIGURED TO TRACK AN END-OF-LIFE PARAMETER.

Applicant of the present application owns the following patent applications that were filed on Dec. 18, 2014 and which are each herein incorporated by reference in their respective entireties:

- U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;
- U.S. patent application Ser. No. 14/574,483, entitled SURGICAL INSTRUMENT ASSEMBLY COMPRISING LOCKABLE SYSTEMS;
- U.S. patent application Ser. No. 14/575,139, entitled DRIVE ARRANGEMENTS FOR ARTICULATABLE SURGICAL INSTRUMENTS;
- U.S. patent application Ser. No. 14/575,148, entitled LOCKING ARRANGEMENTS FOR DETACHABLE SHAFT ASSEMBLIES WITH ARTICULATABLE SURGICAL END EFFECTORS;
- U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;
- U.S. patent application Ser. No. 14/575,143, entitled SURGICAL INSTRUMENTS WITH IMPROVED CLOSURE ARRANGEMENTS;
- U.S. patent application Ser. No. 14/575,117, entitled SURGICAL INSTRUMENTS WITH ARTICULAT-

ABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Patent Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Patent Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS;

U.S. patent application Ser. No. 14/226,099, entitled STERILIZATION VERIFICATION CIRCUIT;

U.S. patent application Ser. No. 14/226,094, entitled VERIFICATION OF NUMBER OF BATTERY EXCHANGES/PROCEDURE COUNT;

U.S. patent application Ser. No. 14/226,117, entitled POWER MANAGEMENT THROUGH SLEEP OPTIONS OF SEGMENTED CIRCUIT AND WAKE UP CONTROL;

U.S. patent application Ser. No. 14/226,075, entitled MODULAR POWERED SURGICAL INSTRUMENT WITH DETACHABLE SHAFT ASSEMBLIES;

U.S. patent application Ser. No. 14/226,093, entitled FEEDBACK ALGORITHMS FOR MANUAL BAIL-OUT SYSTEMS FOR SURGICAL INSTRUMENTS;

U.S. patent application Ser. No. 14/226,116, entitled SURGICAL INSTRUMENT UTILIZING SENSOR ADAPTATION;

U.S. patent application Ser. No. 14/226,071, entitled SURGICAL INSTRUMENT CONTROL CIRCUIT HAVING A SAFETY PROCESSOR;

U.S. patent application Ser. No. 14/226,097, entitled SURGICAL INSTRUMENT COMPRISING INTERACTIVE SYSTEMS;

U.S. patent application Ser. No. 14/226,126, entitled INTERFACE SYSTEMS FOR USE WITH SURGICAL INSTRUMENTS;

U.S. patent application Ser. No. 14/226,133, entitled MODULAR SURGICAL INSTRUMENT SYSTEM;

U.S. patent application Ser. No. 14/226,081, entitled SYSTEMS AND METHODS FOR CONTROLLING A SEGMENTED CIRCUIT;

U.S. patent application Ser. No. 14/226,076, entitled POWER MANAGEMENT THROUGH SEGMENTED CIRCUIT AND VARIABLE VOLTAGE PROTECTION;

U.S. patent application Ser. No. 14/226,111, entitled SURGICAL STAPLING INSTRUMENT SYSTEM; and U.S. patent application Ser. No. 14/226,125, entitled SURGICAL INSTRUMENT COMPRISING A ROTATABLE SHAFT.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE;

U.S. patent application Ser. No. 14/479,119, entitled ADJUNCT WITH INTEGRATED SENSORS TO QUANTIFY TISSUE COMPRESSION;

U.S. patent application Ser. No. 14/478,908, entitled MONITORING DEVICE DEGRADATION BASED ON COMPONENT EVALUATION;

U.S. patent application Ser. No. 14/478,895, entitled MULTIPLE SENSORS WITH ONE SENSOR AFFECTING A SECOND SENSOR'S OUTPUT OR INTERPRETATION;

U.S. patent application Ser. No. 14/479,110, entitled USE OF POLARITY OF HALL MAGNET DETECTION TO DETECT MISLOADED CARTRIDGE;

U.S. patent application Ser. No. 14/479,098, entitled SMART CARTRIDGE WAKE UP OPERATION AND DATA RETENTION;

U.S. patent application Ser. No. 14/479,115, entitled MULTIPLE MOTOR CONTROL FOR POWERED MEDICAL DEVICE; and U.S. patent application Ser. No. 14/479,108, entitled LOCAL DISPLAY OF TISSUE PARAMETER STABILIZATION.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

The present disclosure provides an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples. The features illustrated or described in connection with one example may be combined with the features of other examples. Such modifications and variations are intended to be included within the scope of the present disclosure.

Reference throughout the specification to "various aspects," "some aspects," "one aspect," or "an aspect", or the like, means that a particular feature, structure, or characteristic described in connection with the aspect is included in at least one aspect. Thus, appearances of the phrases "in various aspects," "in some aspects," "in one aspect", or "in an aspect", or the like, in places throughout the specification are not necessarily all referring to the same aspect. Furthermore, the particular features, structures, or characteristics may be combined in any suitable manner in one or more aspects. Thus, the particular features, structures, or characteristics illustrated or described in connection with one aspect may be combined, in whole or in part, with the features structures, or characteristics of one or more other aspects without limitation. Such modifications and variations are intended to be included within the scope of the present disclosure.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated examples, the instrument 10 includes a housing 12 that comprises a handle assembly 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719, is incorporated by reference herein in its entirety.

Figure 2:
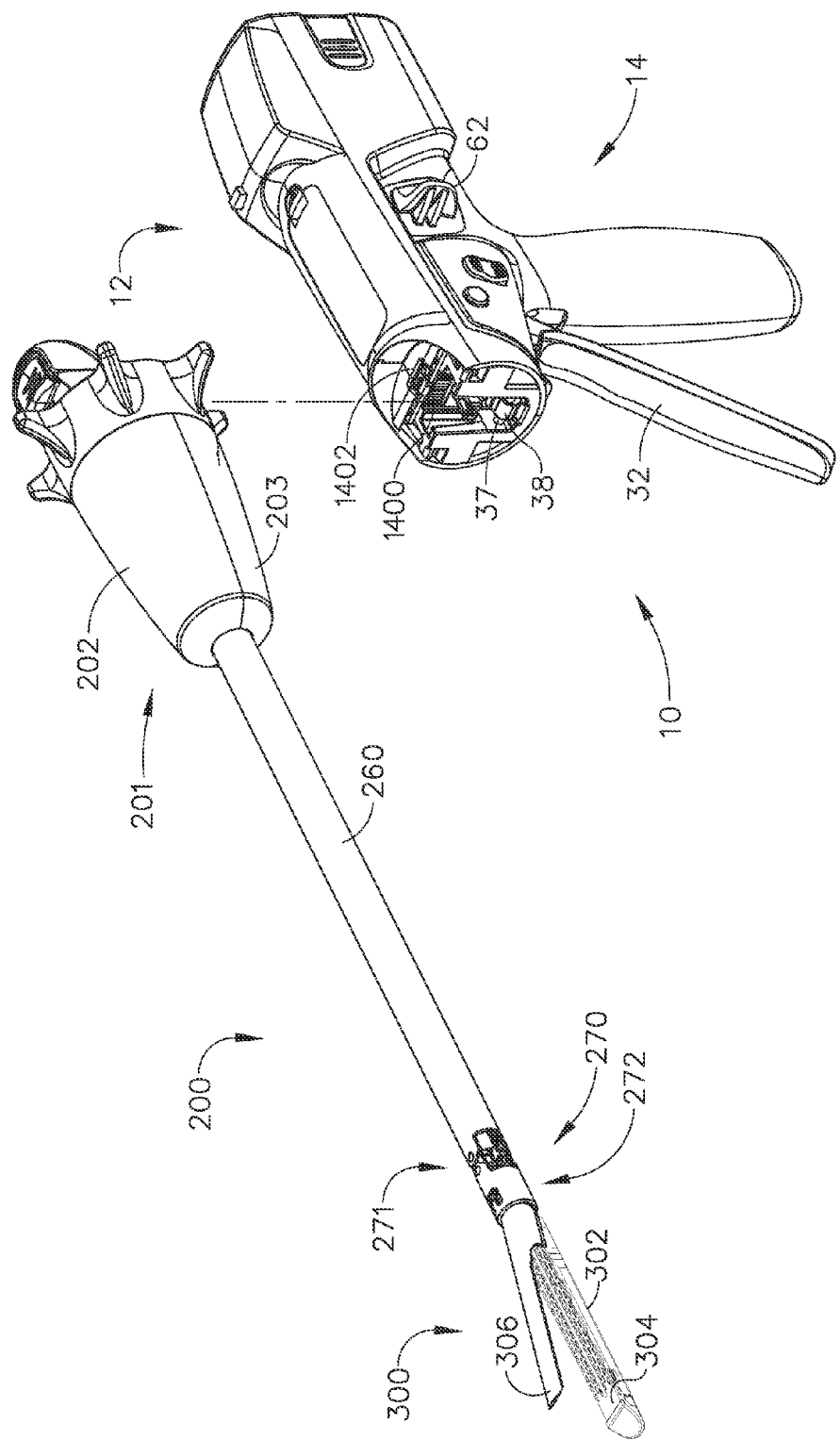
FIG. 2 is an exploded assembly view of the interchangeable shaft assembly and surgical instrument of FIG. 1.
Figure 3:
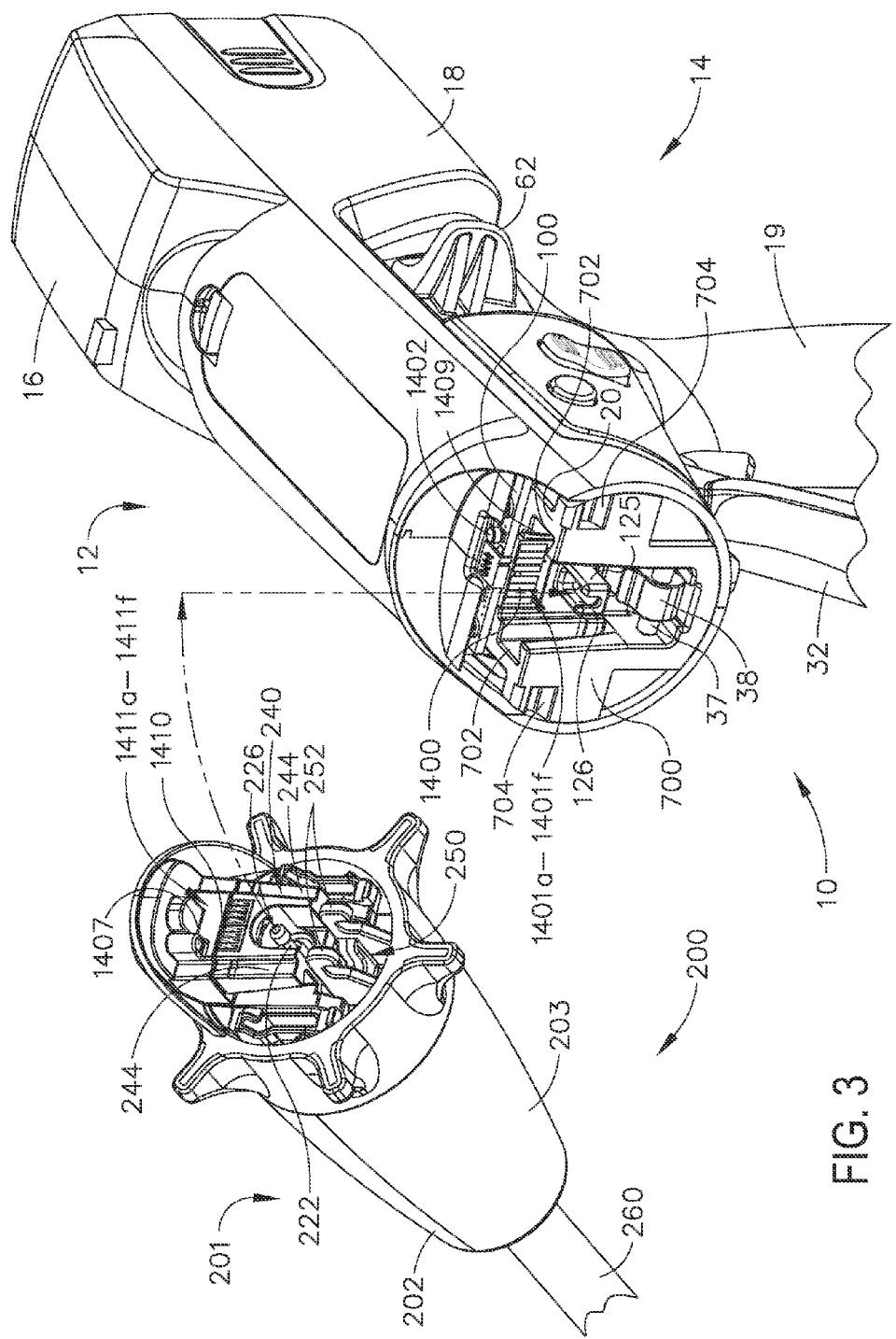
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
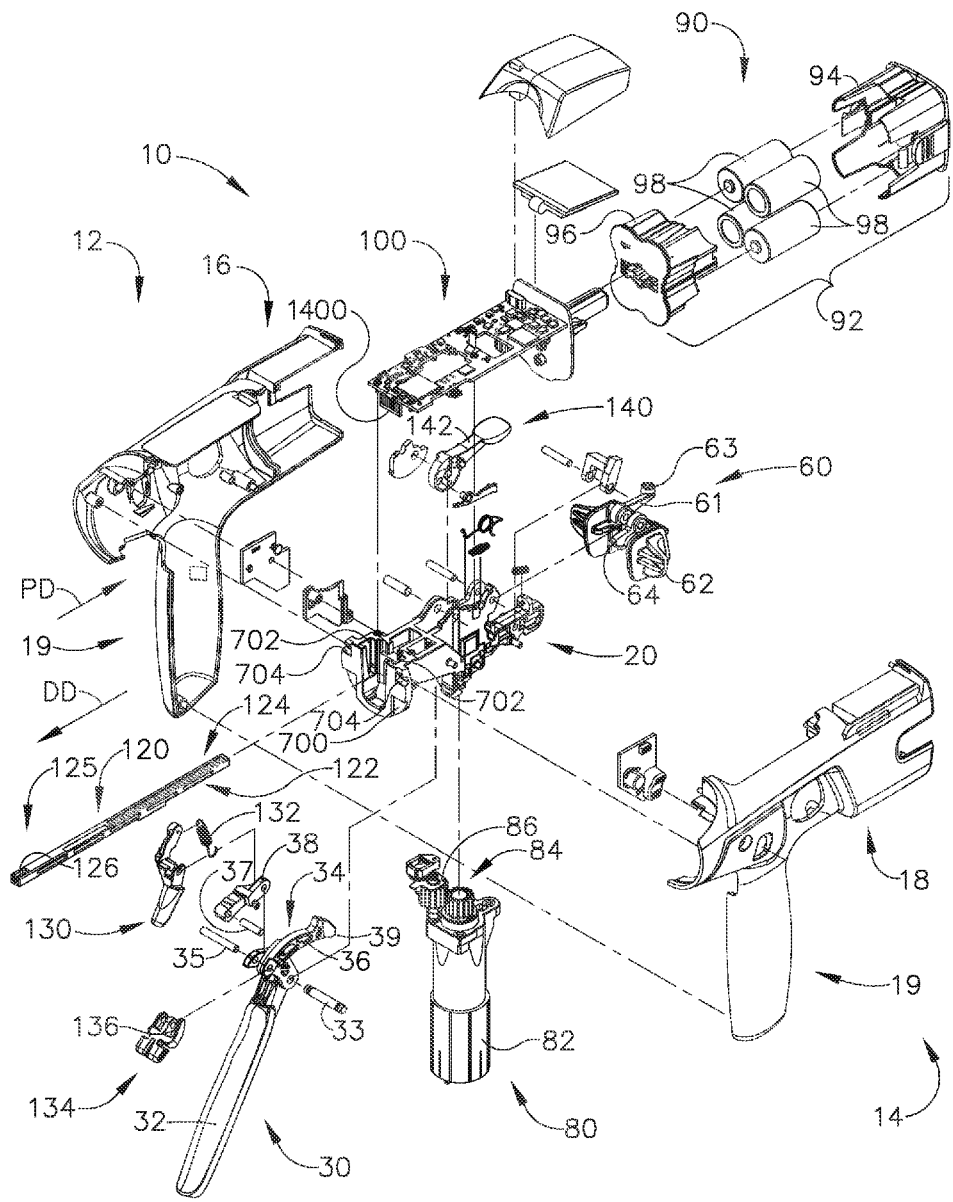
FIG. 4 is an exploded assembly view of a portion of the surgical instrument of FIGS. 1-3.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle assembly 14. As shown in FIG. 4, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle assembly 14 operably supports a plurality of drive systems therein that are configured to generate and apply various control motions to corresponding portions of the interchangeable shaft assembly that is operably attached thereto.

Referring now to FIG. 4, the handle assembly 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle assembly 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 also may be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle assembly 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements also may be employed.

Figure 13:
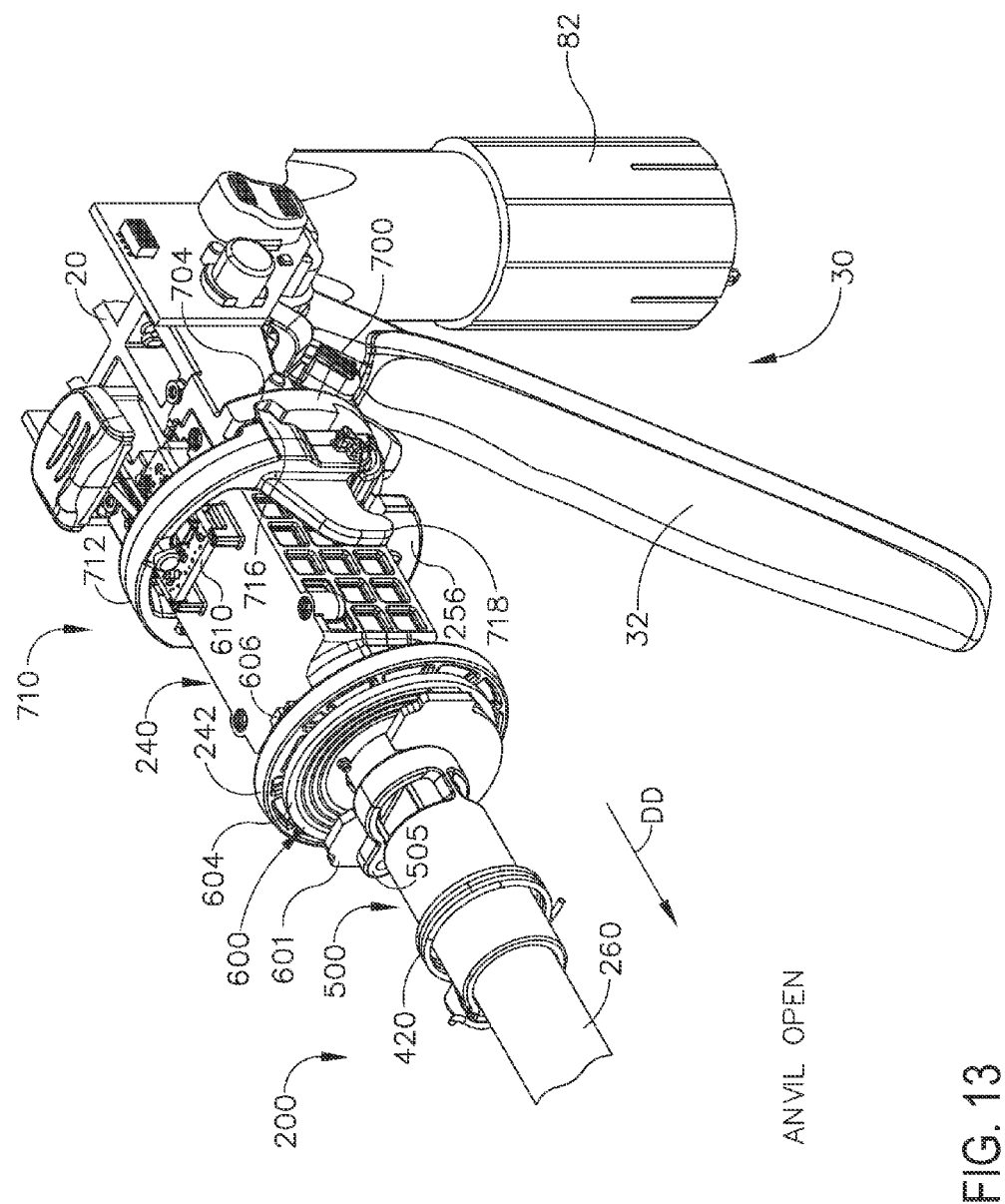
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
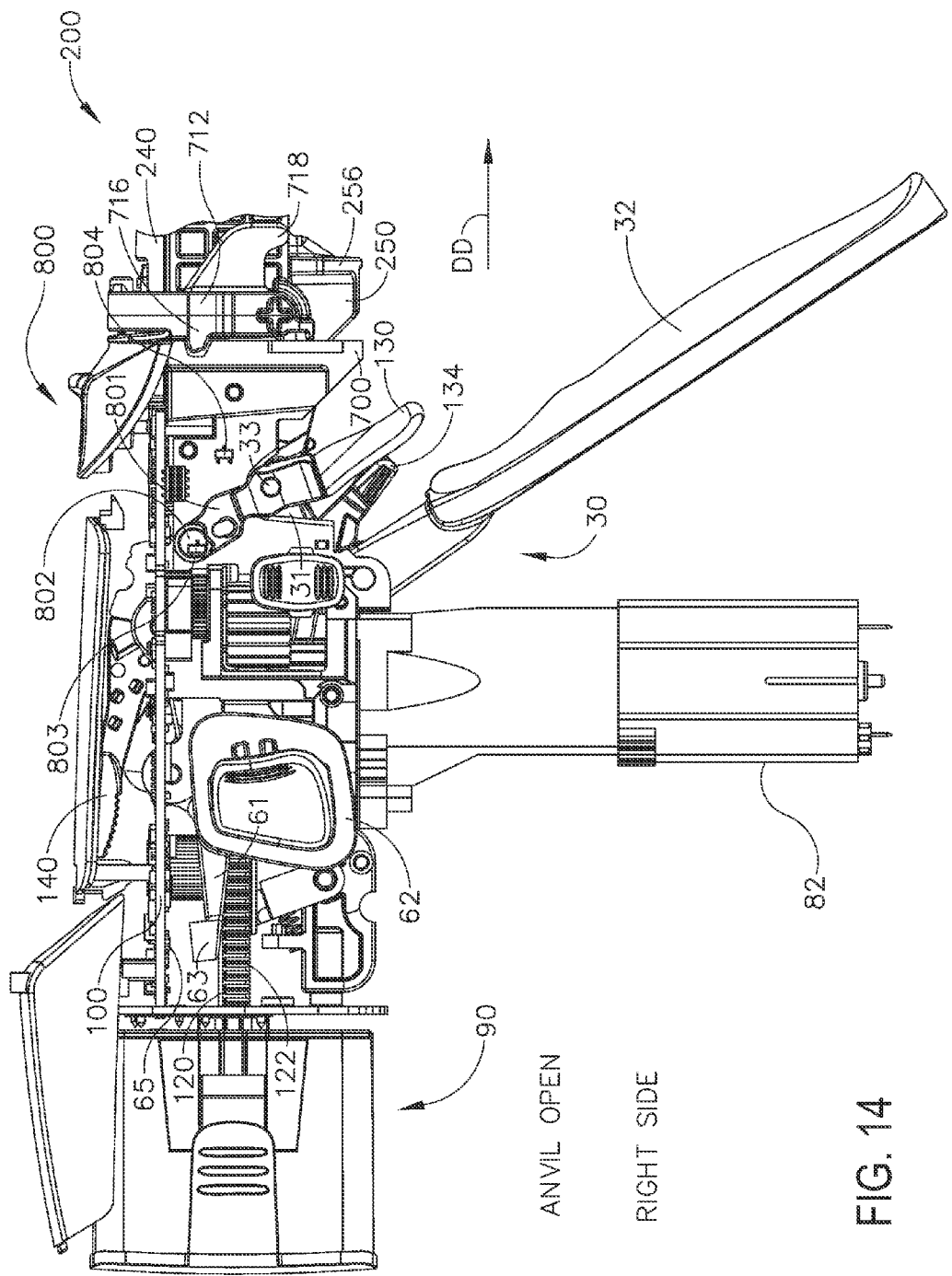
FIG. 14 is a right side elevational view of the interchangeable shaft assembly and surgical instrument of FIG. 13.
Figure 15:
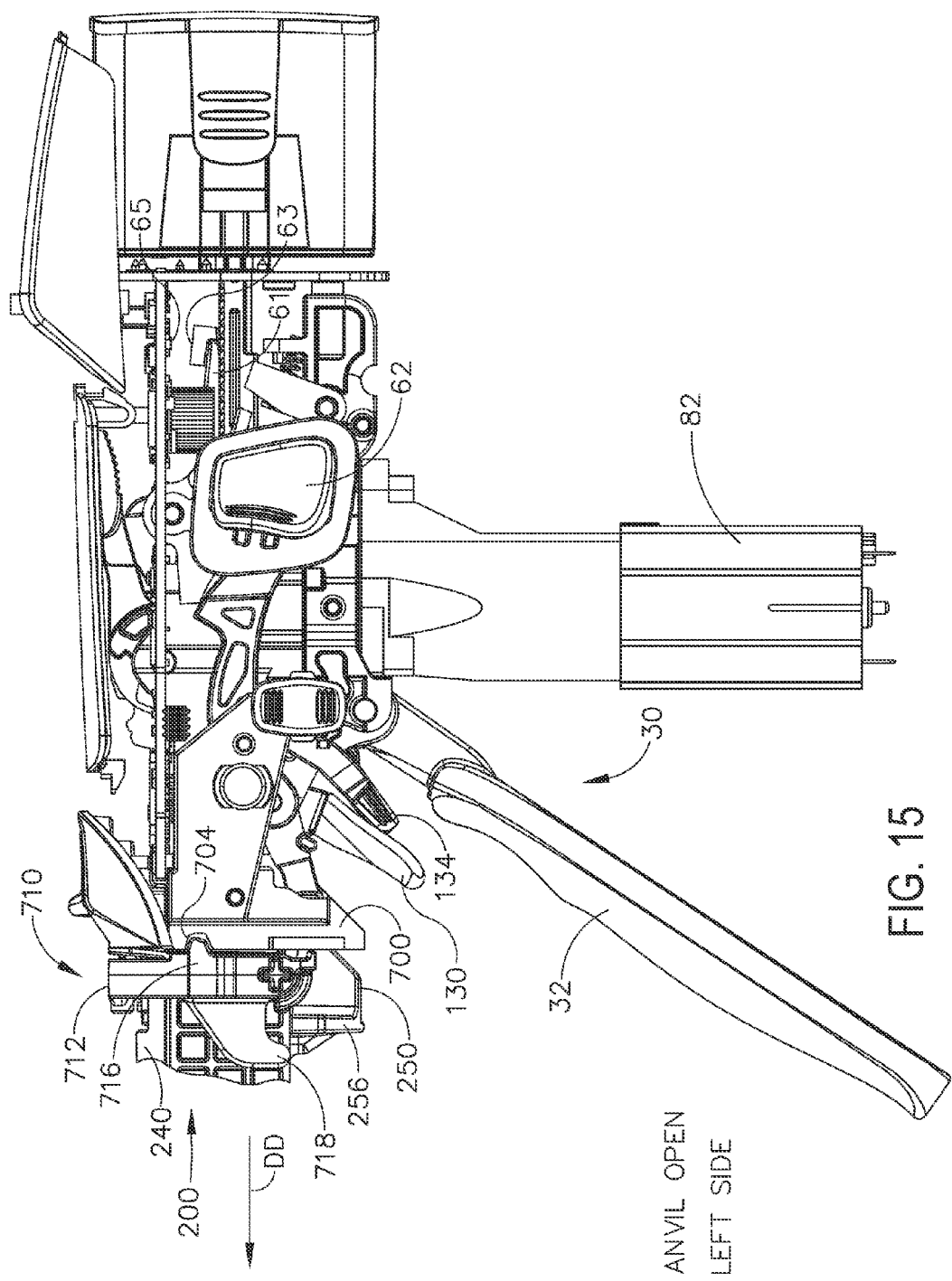
FIG. 15 is a left side elevational view of the interchangeable shaft assembly and surgical instrument of FIGS. 13 and 14.
Figure 16:
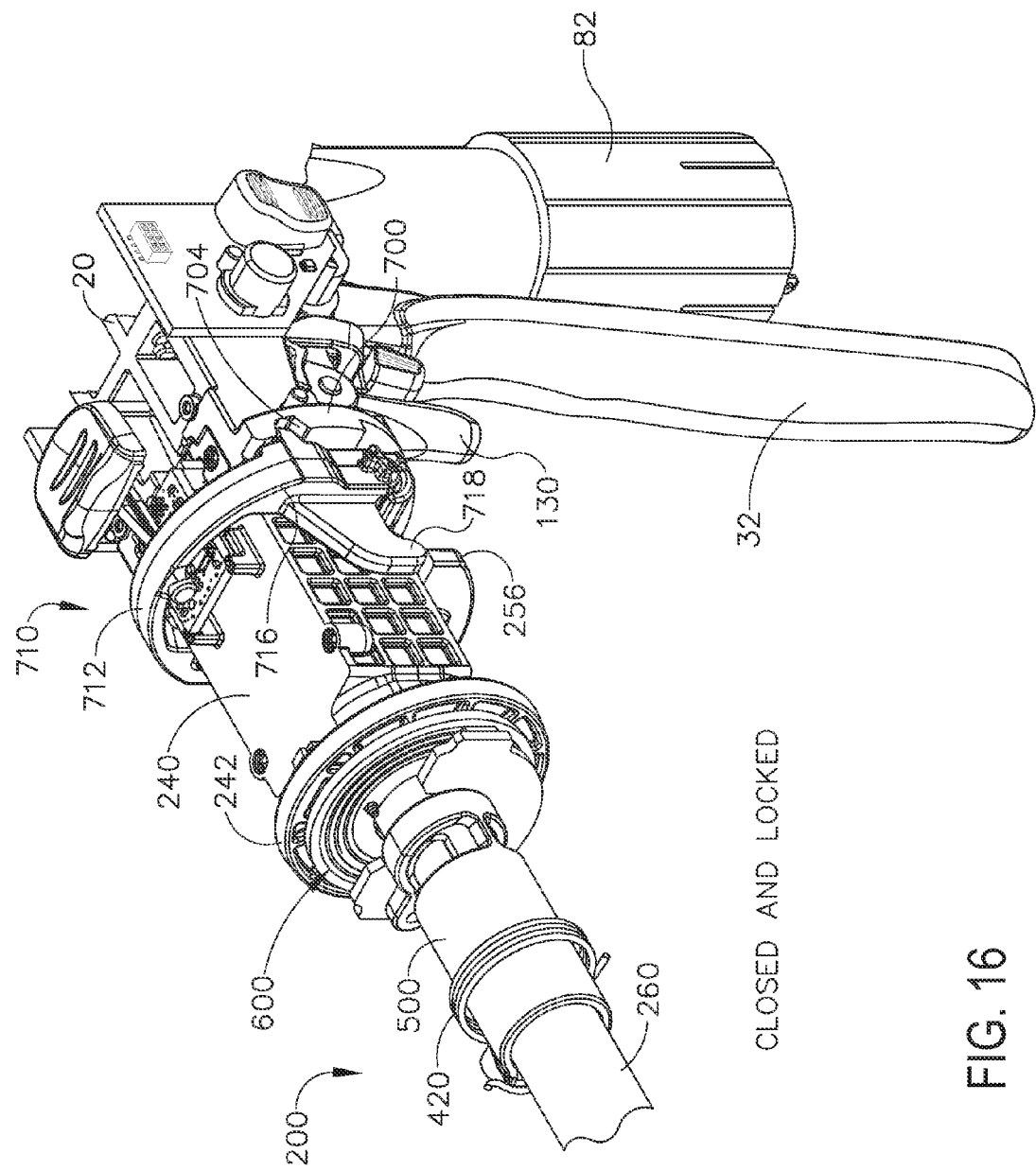
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
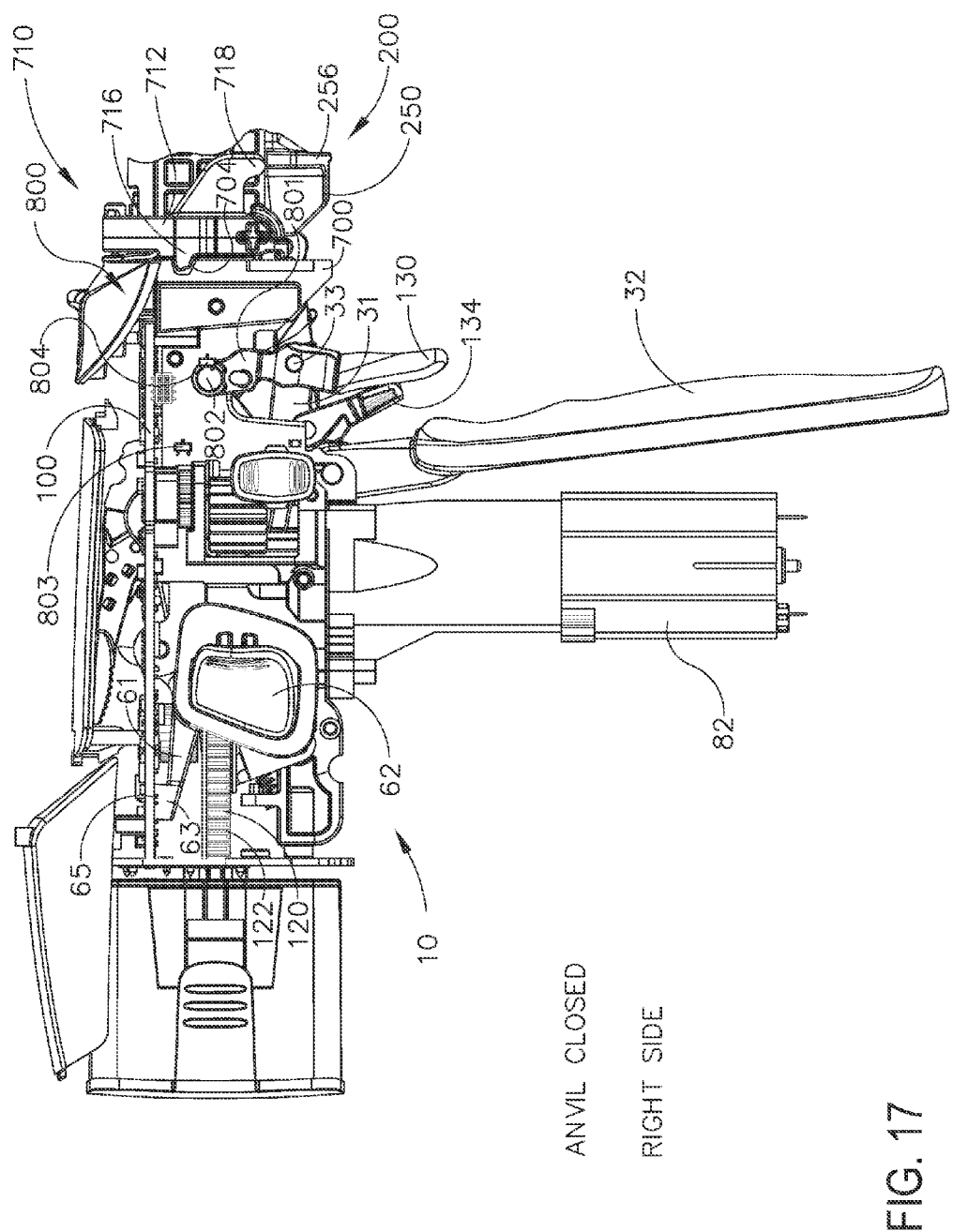
FIG. 17 is a right side elevational view of the interchangeable shaft assembly and surgical instrument of FIG. 16.
Figure 18:
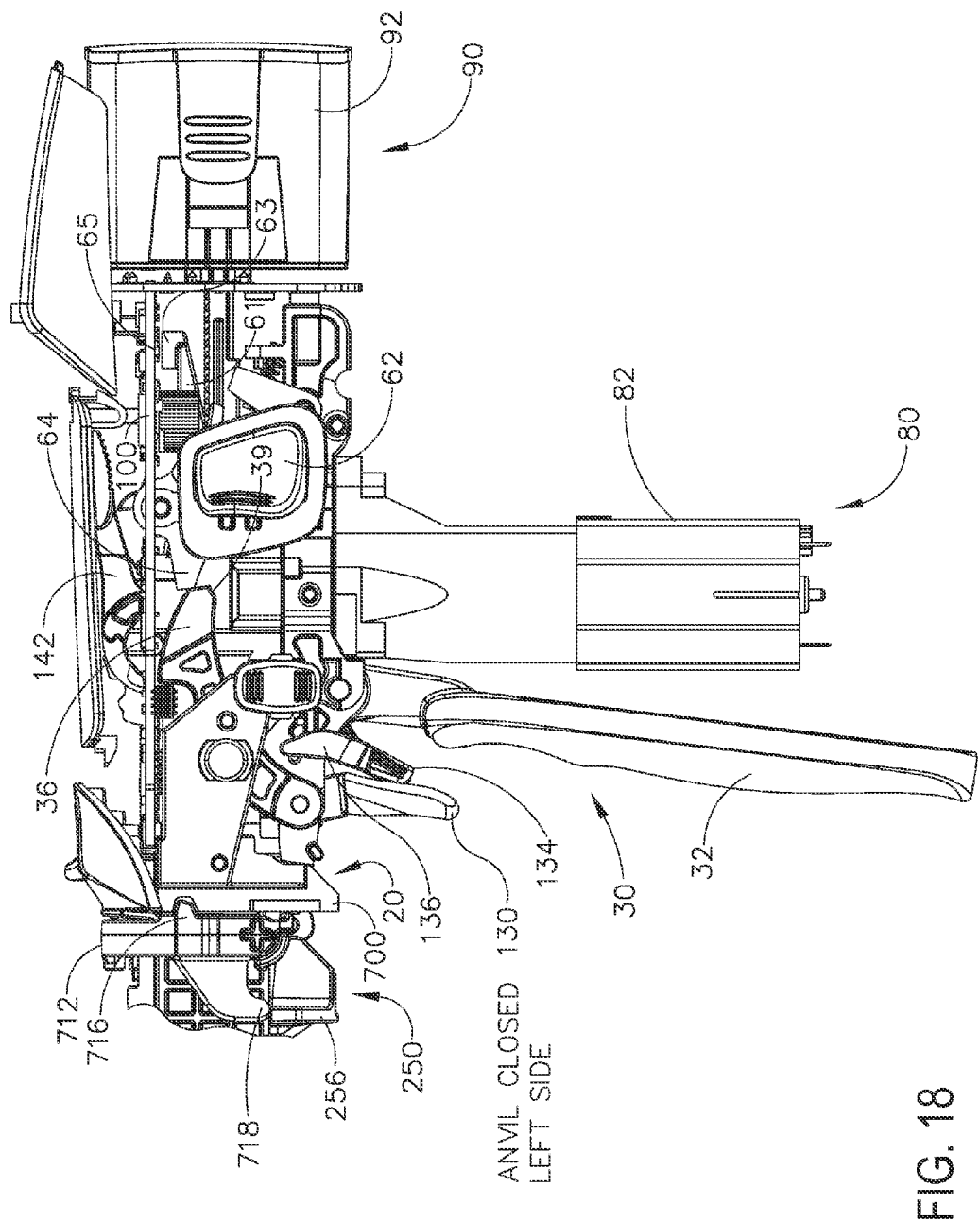
FIG. 18 is a left side elevational view of the interchangeable shaft assembly and surgical instrument of FIGS. 16 and 17.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one aspect, a magnetic field sensor 65, for example, can be mounted to the bottom surface of the circuit board 100. The magnetic field sensor 65 can be configured to detect changes in a magnetic field surrounding the magnetic field sensor 65 caused by the movement of the magnetic element 63. The magnetic field sensor 65 can be in signal communication with a microcontroller 1500 (FIG. 19), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

As used throughout the present disclosure, a magnetic field sensor may be a Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In at least one form, the handle assembly 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle assembly 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As shown in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle assembly 14 can include a switch which can be configured to reverse the polarity applied to the electric motor 82 by the power source 90. As with the other forms described herein, the handle assembly 14 can also include a sensor that is configured to detect the position of the drive member 120 and/or the direction in which the drive member 120 is being moved.

Actuation of the motor 82 can be controlled by a firing trigger 130 that is pivotally supported on the handle assembly 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle assembly 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle assembly 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle assembly 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first magnetic field sensor 803 and a second magnetic field sensor 804, for example, which can be configured to track the position of the magnet 802.

Upon comparing FIGS. 14 and 17, the reader will appreciate that, when the closure trigger 32 is moved from its unactuated position to its actuated position, the magnet 802 can move between a first position adjacent the first magnetic field sensor 803 and a second position adjacent the second magnetic field sensor 804.

Upon comparing FIGS. 17 and 18A, the reader will further appreciate that, when the firing trigger 130 is moved from an unfired position (FIG. 17) to a fired position (FIG. 18A), the magnet 802 can move relative to the second magnetic field sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 14 that is configured to be manually pivoted into ratcheting engagement with teeth 124 also provided in the drive member 120. Thus, the clinician can manually retract the drive member 120 by using the bailout handle assembly 14 to ratchet the drive member 120 in the proximal direction "PD". U.S. Patent Application Publication No. US 2010/0089970, now U.S. Pat. No. 8,608,045 discloses bailout arrangements and other components, arrangements and systems that also may be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, U.S. Patent Application Publication No. 2010/0089970, now U.S. Pat. No. 8,608,045, is hereby incorporated by reference in its entirety.

Figure 7:
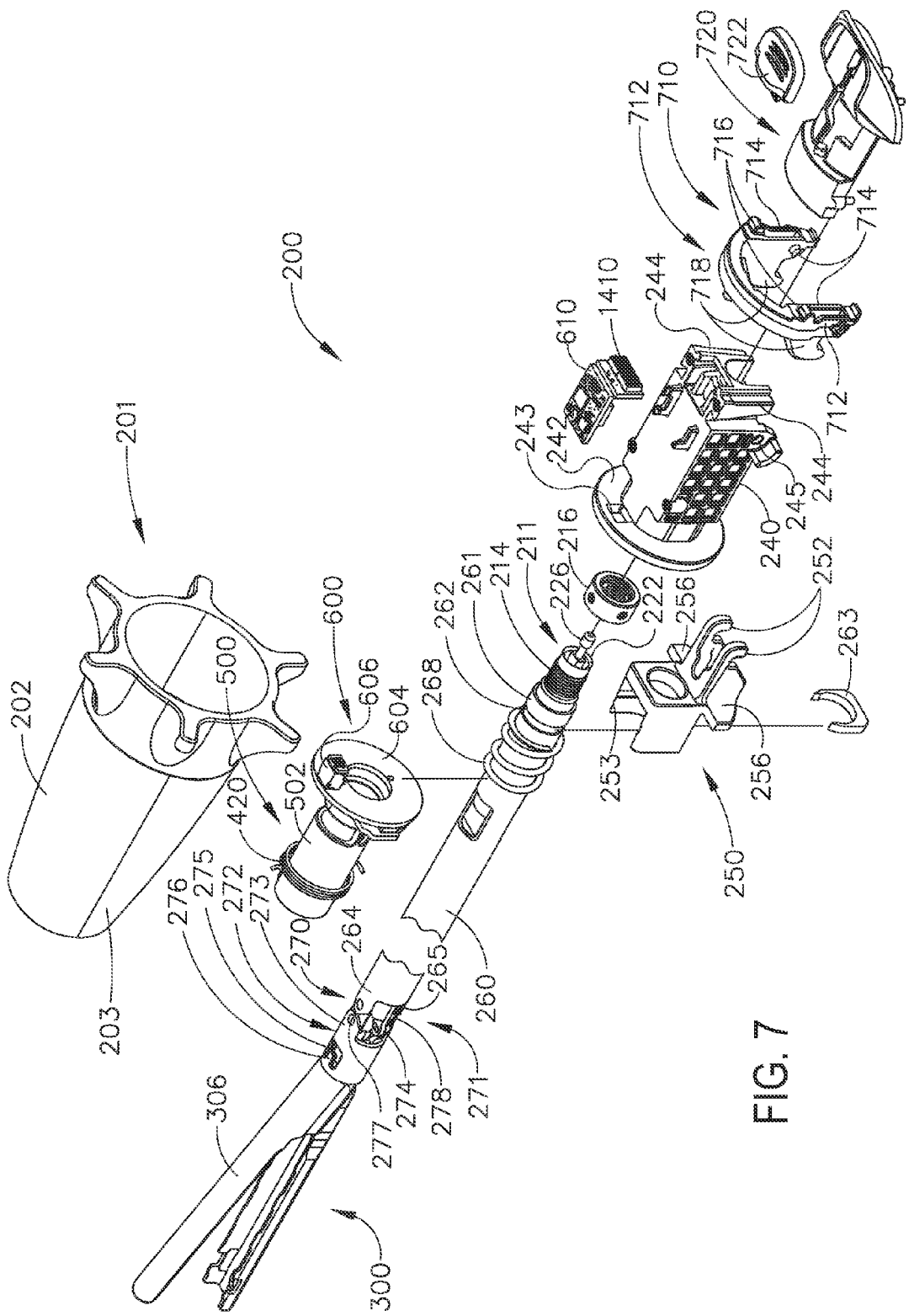
FIG. 7 is an exploded assembly view of one form of an interchangeable shaft assembly.
Figure 8:
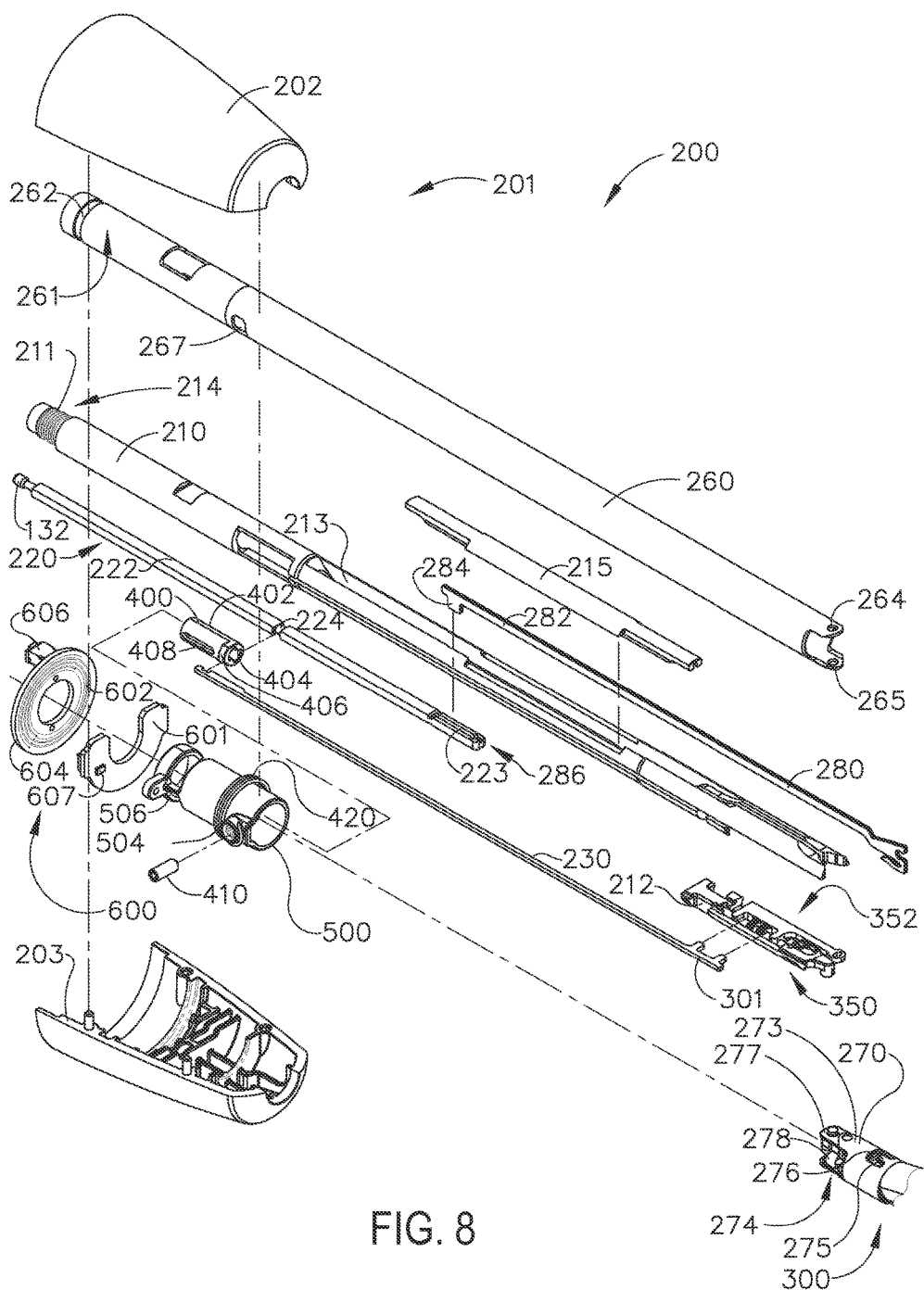
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As shown in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086, now U.S. Patent Application Publication No. 2014/0263541. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As shown in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle assembly 14.

In at least one form, the interchangeable shaft assembly 200 may further include an articulation joint 270. Other interchangeable shaft assemblies, however, may not be capable of articulation. As shown in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086, now U.S. Patent Application Publication No. 2014/0263541. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086, now U.S. Patent Application Publication No. 2014/0263541, which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 also may be articulated relative to the closure tube 260 by an articulation driver 230.

Figure 9:
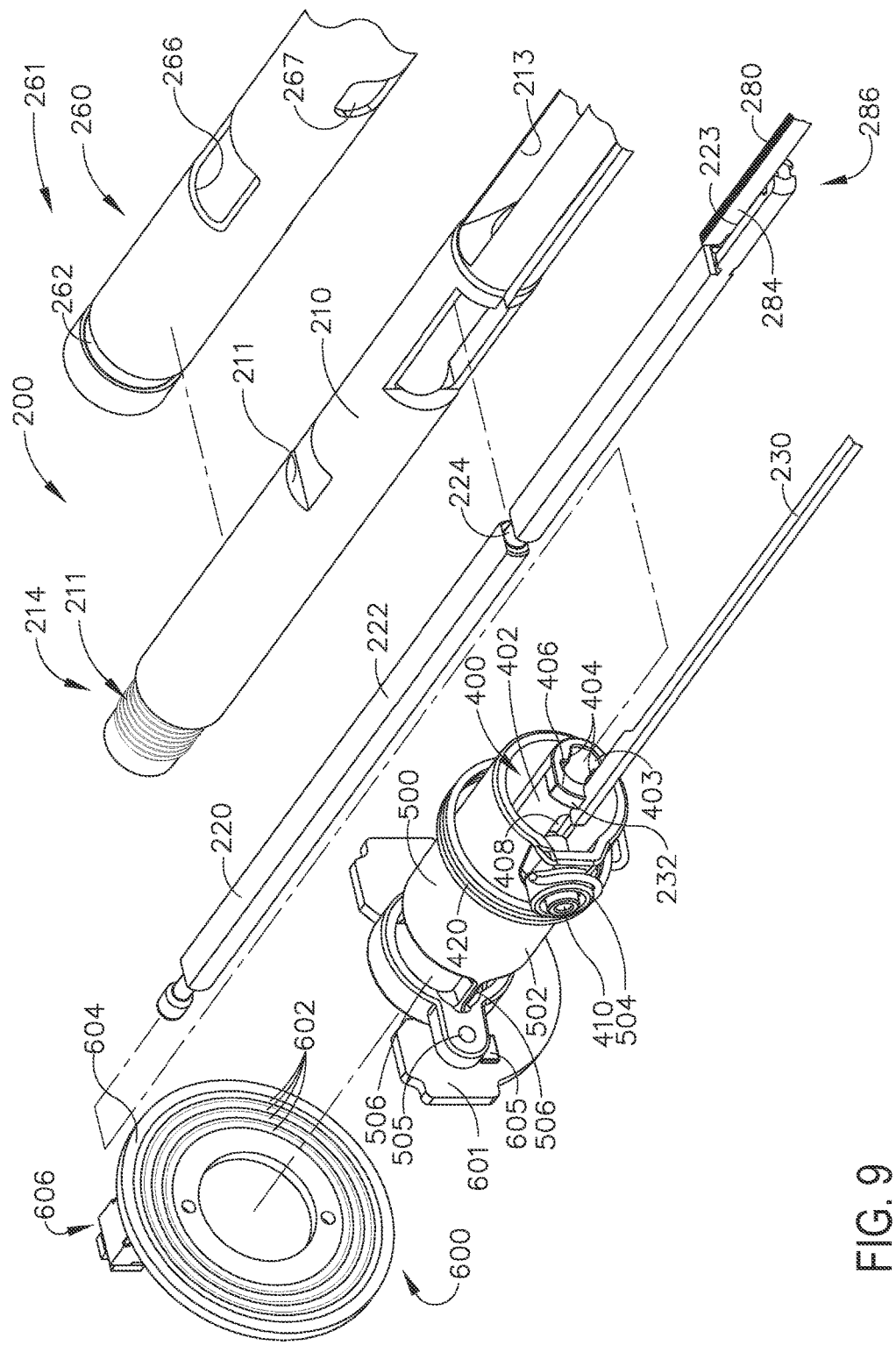
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 also may be referred to herein as a "second shaft" and/or a "second shaft assembly". As shown in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086, now U.S. Patent Application Publication No. 2014/0263541.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
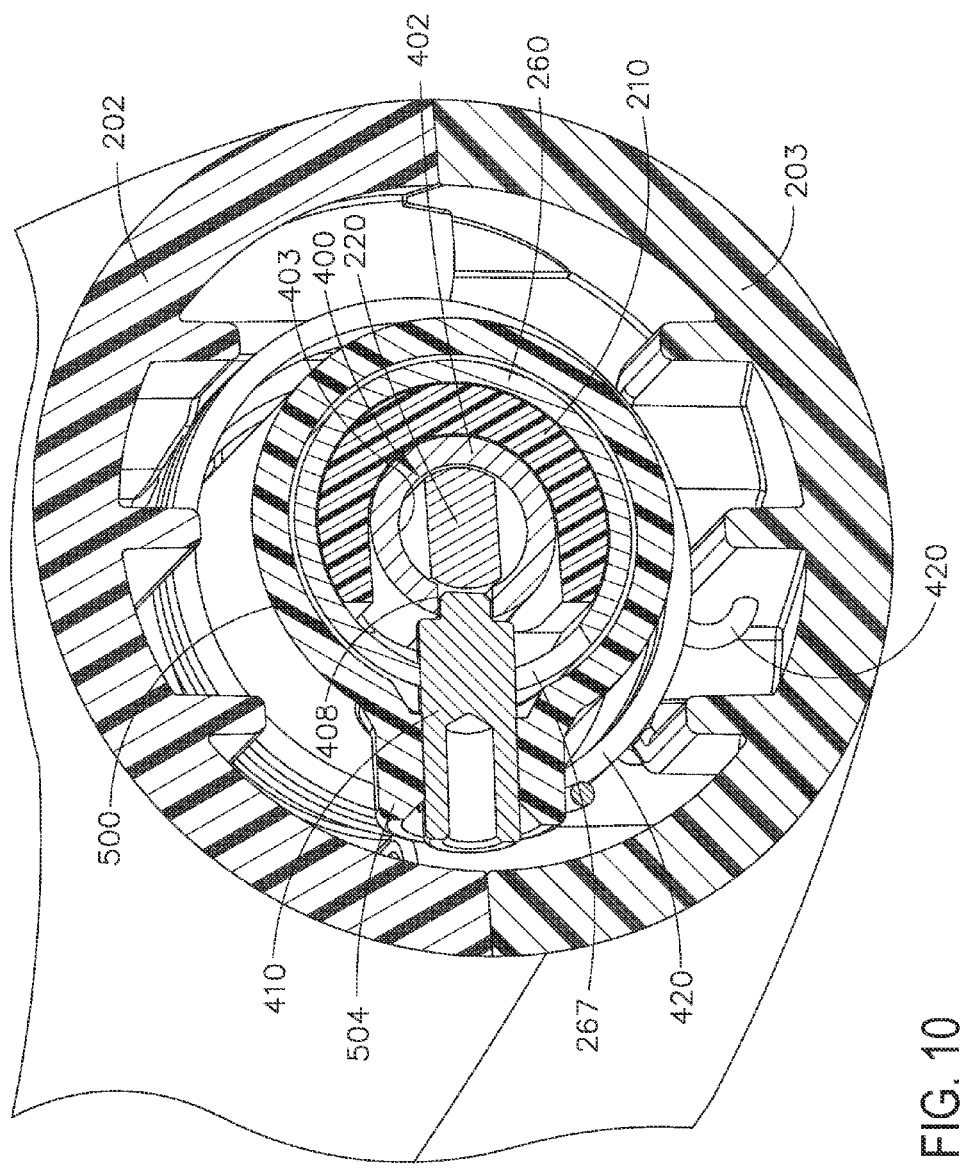
FIG. 10 is a cross-sectional view of a portion of the interchangeable shaft assembly of FIGS. 7-9.

As shown in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As shown in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of eth actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803, 086, now U.S. Patent Application Publication No. 2014/ 0263541.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551, is incorporated by reference in its entirety. Further details regarding slip ring assembly 600 may be found in U.S. patent application Ser. No. 13/803, 086, now U.S. Patent Application Publication No. 2014/ 0263541.

Figure 11:
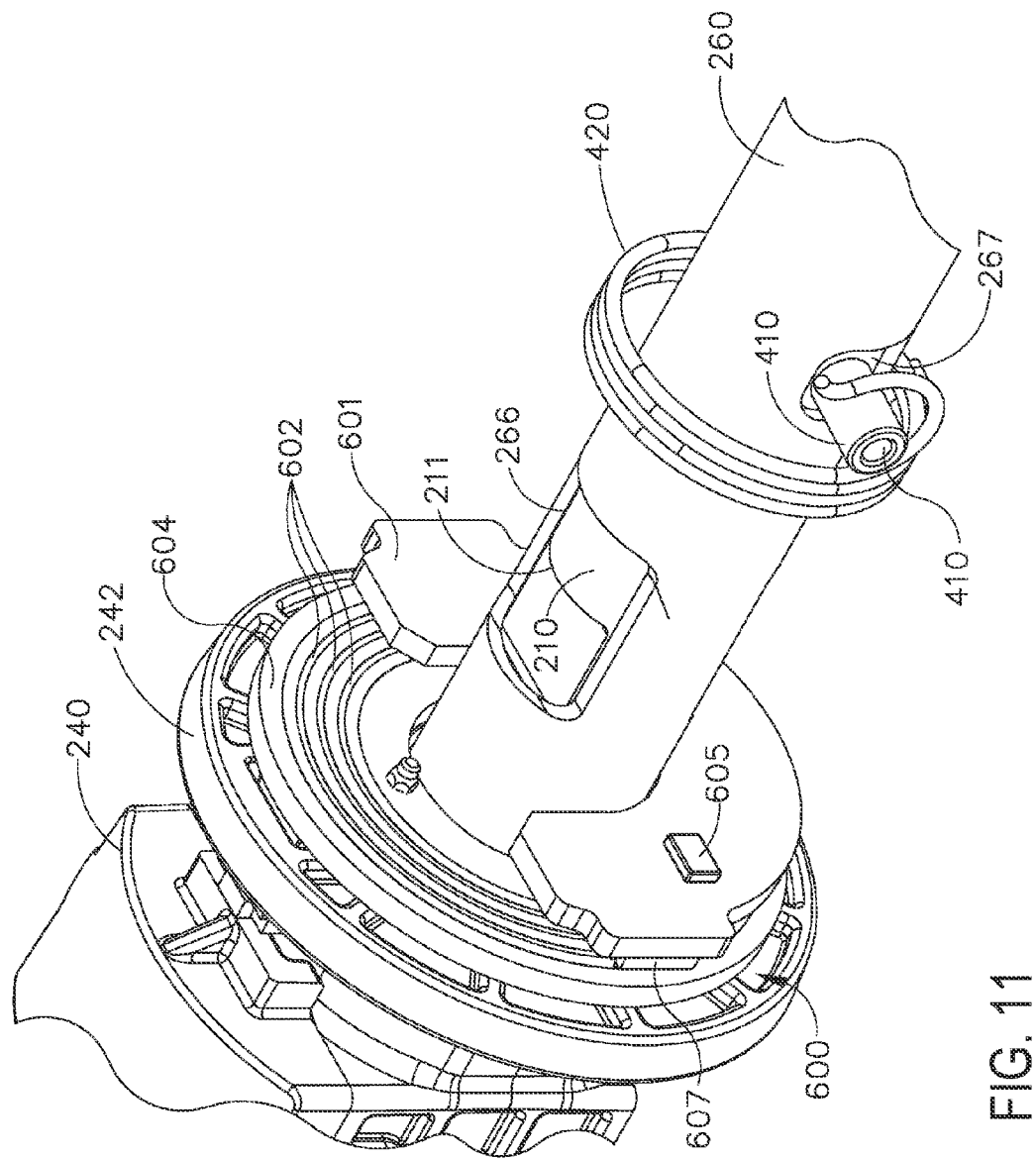
FIG. 11 is a perspective view of a portion of the shaft assembly of FIGS. 7-10 with the switch drum omitted for clarity.
Figure 12:
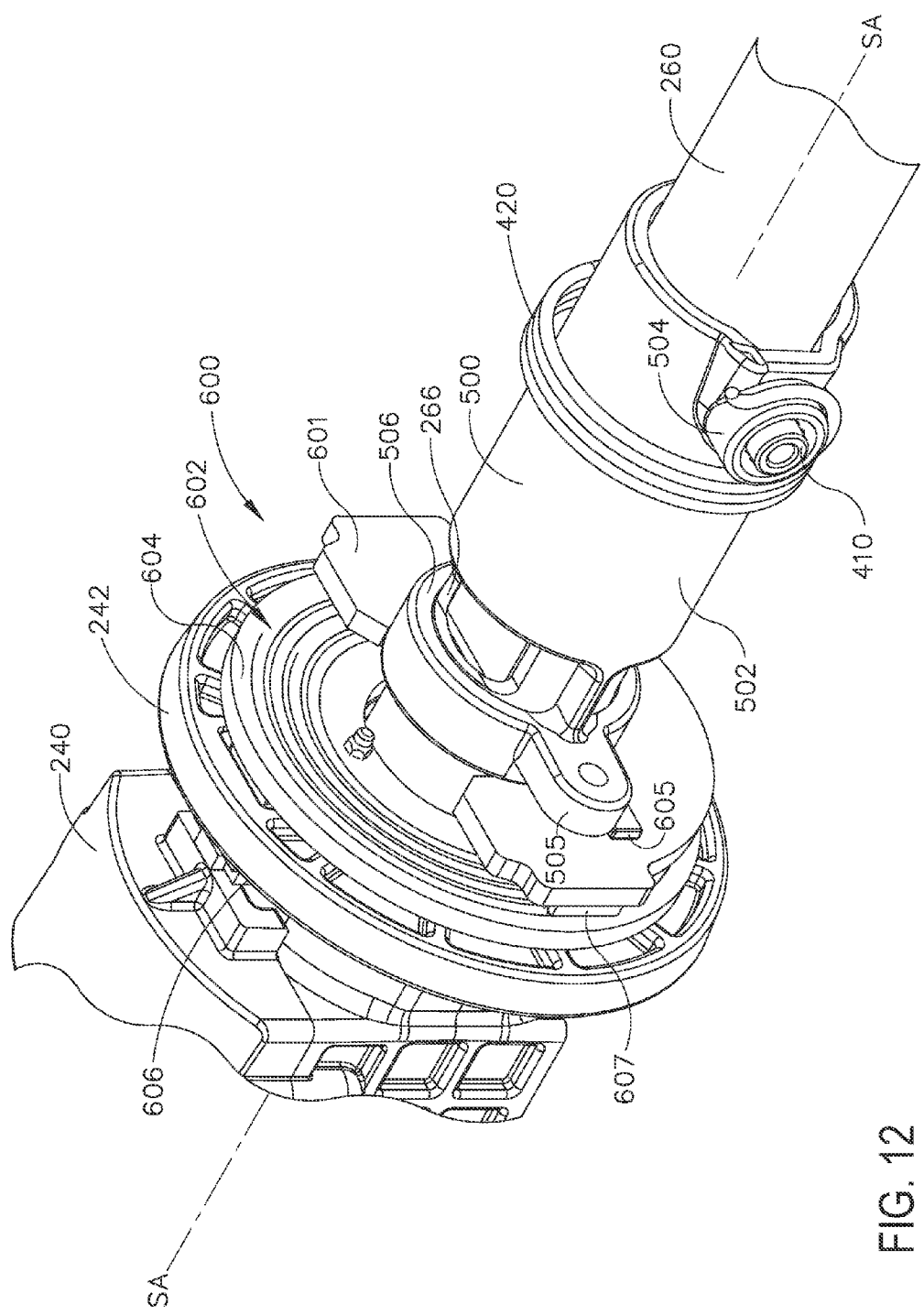
FIG. 12 is another perspective view of the portion of the interchangeable shaft assembly of FIG. 11 with the switch drum mounted thereon.

As discussed above, the shaft assembly 200 can include a proximal portion which is fixably mounted to the handle assembly 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a magnetic field sensor 605, for example, and the switch drum 500 can comprise a magnetic element, such as permanent magnet 505, for example. The magnetic field sensor 605 can be configured to detect the position of the permanent magnet 505. When the switch drum 500 is rotated between its first position and its second position, the permanent magnet 505 can move relative to the magnetic field sensor 605. In various instances, magnetic field sensor 605 can detect changes in a magnetic field created when the permanent magnet 505 is moved. The magnetic field sensor 605 can be in signal communication with the shaft circuit board 610 and/or the handle circuit board 100, for example. Based on the signal from the magnetic field sensor 605, a microcontroller on the shaft circuit board 610 and/or the handle circuit board 100 can determine whether the articulation drive system is engaged with or disengaged from the firing drive system.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle assembly 14, the shaft attachment lug 226 is received in a firing shaft attachment cradle 126 formed in the distal end 125 of the longitudinal drive member 120 as shown in FIGS. 3 and 6, for example.

Various shaft assemblies employ a latch system 710 for removably coupling the shaft assembly 200 to the housing 12 and more specifically to the frame 20. As shown in FIG. 7, for example, in at least one form, the latch system 710 includes a lock member or lock yoke 712 that is movably coupled to the chassis 240. In the illustrated example, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was inadvertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle assembly 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle assembly 14. A first system can comprise a frame system which couples and/or aligns the frame or spine of the shaft assembly 200 with the frame 20 of the handle assembly 14. Another system can comprise a closure drive system 30 which can operably connect the closure trigger 32 of the handle assembly 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle assembly 14 with the intermediate firing shaft 222 of the shaft assembly 200.

As outlined above, the shaft attachment lug 226 can be operably connected with the cradle 126 of the longitudinal drive member 120. Another system can comprise an electrical system which can signal to a controller in the handle assembly 14, such as microcontroller, for example, that a shaft assembly, such as shaft assembly 200, for example, has been operably engaged with the handle assembly 14 and/or, two, conduct power and/or communication signals between the shaft assembly 200 and the handle assembly 14. For instance, the shaft assembly 200 can include an electrical connector 1410 that is operably mounted to the shaft circuit board 610. The electrical connector 1410 is configured for mating engagement with a corresponding electrical connector 1400 on the handle control board 100. Further details regaining the circuitry and control systems may be found in U.S. patent application Ser. No. 13/803,086, the entire disclosure of which was previously incorporated by reference herein. The fifth system may consist of the latching system for releasably locking the shaft assembly 200 to the handle assembly 14.

Figure 19:
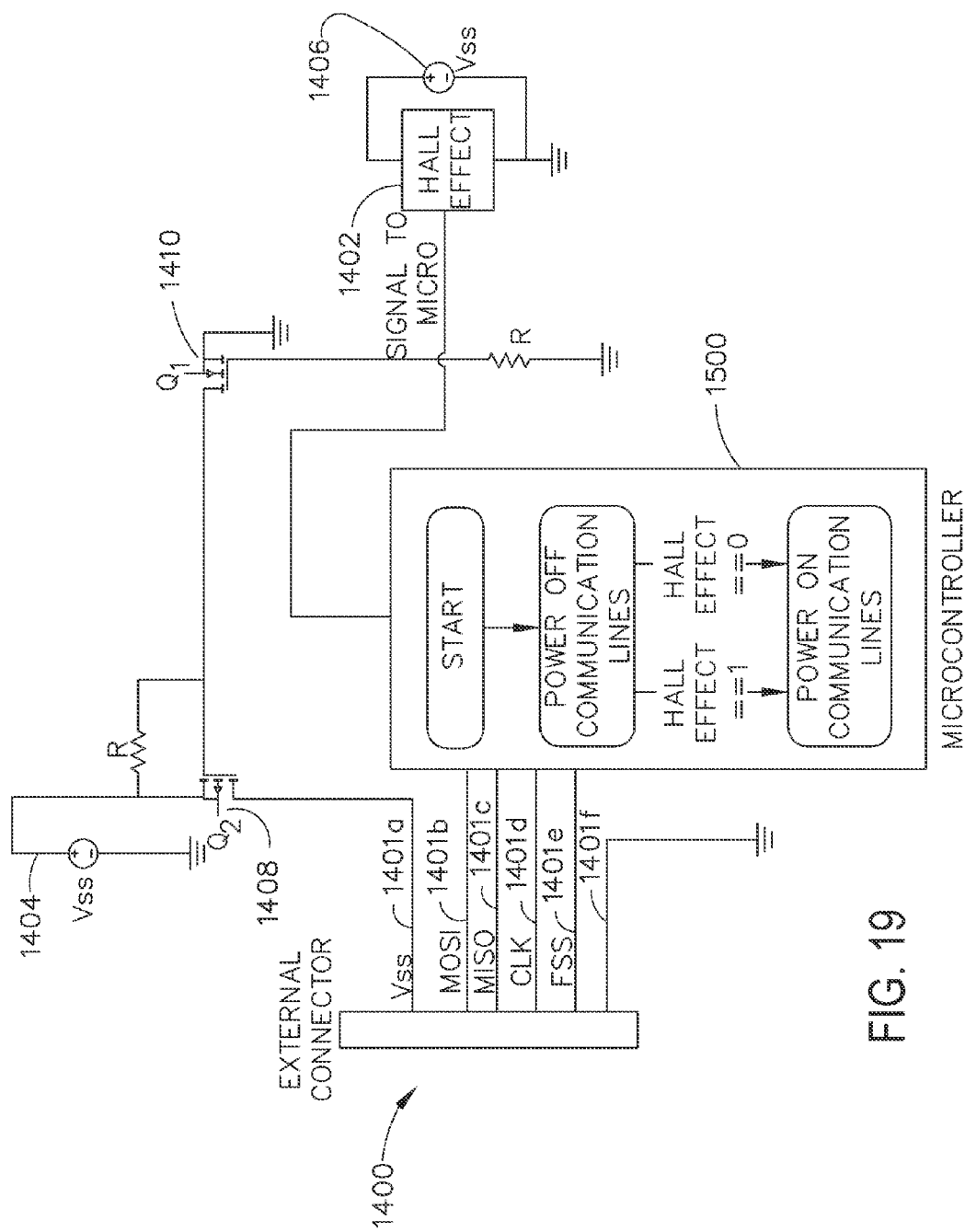
FIG. 19 is a schematic of a system for powering down an electrical connector of a surgical instrument handle when a shaft assembly is not coupled thereto.

Referring again to FIGS. 2 and 3, the handle assembly 14 can include an electrical connector 1400 comprising a plurality of electrical contacts. Turning now to FIG. 19, the electrical connector 1400 can comprise a first contact 1401a, a second contact 1401b, a third contact 1401c, a fourth contact 1401d, a fifth contact 1401e, and a sixth contact 1401f, for example. While the illustrated example utilizes six contacts, other examples are envisioned which may utilize more than six contacts or less than six contacts.

As illustrated in FIG. 19, the first contact 1401a can be in electrical communication with a transistor 1408, contacts 1401b-1401e can be in electrical communication with a microcontroller 1500, and the sixth contact 1401f can be in electrical communication with a ground. In certain circumstances, one or more of the electrical contacts 1401b-1401e may be in electrical communication with one or more output channels of the microcontroller 1500 and can be energized, or have a voltage potential applied thereto, when the handle 1042 is in a powered state. In some circumstances, one or more of the electrical contacts 1401b-1401e may be in electrical communication with one or more input channels of the microcontroller 1500 and, when the handle assembly 14 is in a powered state, the microcontroller 1500 can be configured to detect when a voltage potential is applied to such electrical contacts. When a shaft assembly, such as shaft assembly 200, for example, is assembled to the handle assembly 14, the electrical contacts 1401a-1401f may not communicate with each other. When a shaft assembly is not assembled to the handle assembly 14, however, the electrical contacts 1401a-1401f of the electrical connector 1400 may be exposed and, in some circumstances, one or more of the contacts 1401a-1401f may be accidentally placed in electrical communication with each other. Such circumstances can arise when one or more of the contacts 1401a-1401f come into contact with an electrically conductive material, for example. When this occurs, the microcontroller 1500 can receive an erroneous input and/or the shaft assembly 200 can receive an erroneous output, for example. To address this issue, in various circumstances, the handle assembly 14 may be unpowered when a shaft assembly, such as shaft assembly 200, for example, is not attached to the handle assembly 14.

In other circumstances, the handle 1042 can be powered when a shaft assembly, such as shaft assembly 200, for example, is not attached thereto. In such circumstances, the microcontroller 1500 can be configured to ignore inputs, or voltage potentials, applied to the contacts in electrical communication with the microcontroller 1500, i.e., contacts 1401b-1401e, for example, until a shaft assembly is attached to the handle assembly 14. Even though the microcontroller 1500 may be supplied with power to operate other functionalities of the handle assembly 14 in such circumstances, the handle assembly 14 may be in a powered-down state. In a way, the electrical connector 1400 may be in a powered-down state as voltage potentials applied to the electrical contacts 1401b-1401e may not affect the operation of the handle assembly 14. The reader will appreciate that, even though contacts 1401b-1401e may be in a powered-down state, the electrical contacts 1401a and 1401f, which are not in electrical communication with the microcontroller 1500, may or may not be in a powered-down state. For instance, sixth contact 1401f may remain in electrical communication with a ground regardless of whether the handle assembly 14 is in a powered-up or a powered-down state.

Furthermore, the transistor 1408, and/or any other suitable arrangement of transistors, such as transistor 1410, for example, and/or switches may be configured to control the supply of power from a power source 1404, such as a battery 90 within the handle assembly 14, for example, to the first electrical contact 1401a regardless of whether the handle assembly 14 is in a powered-up or a powered-down state. In various circumstances, the shaft assembly 200, for example, can be configured to change the state of the transistor 1408 when the shaft assembly 200 is engaged with the handle assembly 14. In certain circumstances, further to the below, a magnetic field sensor 1402 can be configured to switch the state of transistor 1410 which, as a result, can switch the state of transistor 1408 and ultimately supply power from power source 1404 to first contact 1401*a*. In this way, both the power circuits and the signal circuits to the connector 1400 can be powered down when a shaft assembly is not installed to the handle assembly 14 and powered up when a shaft assembly is installed to the handle assembly 14.

In various circumstances, referring again to FIG. 19, the handle assembly 14 can include the magnetic field sensor 1402, for example, which can be configured to detect a detectable element, such as a magnetic element 1407 (FIG. 3), for example, on a shaft assembly, such as shaft assembly 200, for example, when the shaft assembly is coupled to the handle assembly 14. The magnetic field sensor 1402 can be powered by a power source 1406, such as a battery, for example, which can, in effect, amplify the detection signal of the magnetic field sensor 1402 and communicate with an input channel of the microcontroller 1500 via the circuit illustrated in FIG. 19. Once the microcontroller 1500 has a received an input indicating that a shaft assembly has been at least partially coupled to the handle assembly 14, and that, as a result, the electrical contacts 1401*a*-1401*f* are no longer exposed, the microcontroller 1500 can enter into its normal, or powered-up, operating state. In such an operating state, the microcontroller 1500 will evaluate the signals transmitted to one or more of the contacts 1401*b*-1401*e* from the shaft assembly and/or transmit signals to the shaft assembly through one or more of the contacts 1401*b*-1401*e* in normal use thereof. In various circumstances, the shaft assembly 200 may have to be fully seated before the magnetic field sensor 1402 can detect the magnetic element 1407. While a magnetic field sensor 1402 can be utilized to detect the presence of the shaft assembly 200, any suitable system of sensors and/or switches can be utilized to detect whether a shaft assembly has been assembled to the handle assembly 14, for example. In this way, further to the above, both the power circuits and the signal circuits to the connector 1400 can be powered down when a shaft assembly is not installed to the handle assembly 14 and powered up when a shaft assembly is installed to the handle assembly 14.

In various examples, as may be used throughout the present disclosure, any suitable magnetic field sensor may be employed to detect whether a shaft assembly has been assembled to the handle assembly 14, for example. For example, the technologies used for magnetic field sensing include Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 19, the microcontroller 1500 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 1500 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 1500 may include a hybrid circuit comprising discrete and integrated circuit elements or components on one or more substrates, for example.

Referring to FIG. 19, the microcontroller 1500 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle assembly 14 and/or the shaft assembly 200 can include systems and configurations configured to prevent, or at least reduce the possibility of, the contacts of the handle electrical connector 1400 and/or the contacts of the shaft electrical connector 1410 from becoming shorted out when the shaft assembly 200 is not assembled, or completely assembled, to the handle assembly 14. Referring to FIG. 3, the handle electrical connector 1400 can be at least partially recessed within a cavity 1409 defined in the handle frame 20. The six contacts 1401*a*-1401*f* of the electrical connector 1400 can be completely recessed within the cavity 1409. Such arrangements can reduce the possibility of an object accidentally contacting one or more of the contacts 1401*a*-1401*f*. Similarly, the shaft electrical connector 1410 can be positioned within a recess defined in the shaft chassis 240 which can reduce the possibility of an object accidentally contacting one or more of the contacts 1411*a*-1411*f* of the shaft electrical connector 1410. With regard to the particular example depicted in FIG. 3, the shaft contacts 1411*a*-1411*f* can comprise male contacts. In at least one example, each shaft contact 1411*a*-1411*f* can comprise a flexible projection extending therefrom which can be configured to engage a corresponding handle contact 1401*a*-1401*f*, for example. The handle contacts 1401*a*-1401*f* can comprise female contacts. In at least one example, each handle contact 1401*a*-1401*f* can comprise a flat surface, for example, against which the male shaft contacts 1401*a*-1401*f* can wipe, or slide, against and maintain an electrically conductive interface therebetween. In various instances, the direction in which the shaft assembly 200 is assembled to the handle assembly 14 can be parallel to, or at least substantially parallel to, the handle contacts 1401*a*-1401*f* such that the shaft contacts 1411*a*-1411*f* slide against the handle contacts 1401*a*-1401*f* when the shaft assembly 200 is assembled to the handle assembly 14. In various alternative examples, the handle contacts 1401*a*-1401*f* can comprise male contacts and the shaft contacts 1411*a*-1411*f* can comprise female contacts. In certain alternative examples, the handle contacts 1401*a*-1401*f* and the shaft contacts 1411*a*-1411*f* can comprise any suitable arrangement of contacts.

In various instances, the handle assembly 14 can comprise a connector guard configured to at least partially cover the handle electrical connector 1400 and/or a connector guard configured to at least partially cover the shaft electrical connector 1410. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one example, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the microcontroller 1500, for example, can monitor the contacts 1401*a*-1401*f* when a shaft assembly has not been assembled to the handle assembly 14 to determine whether one or more of the contacts 1401*a*-1401*f* may have been shorted. The microcontroller 1500 can be configured to apply a low voltage potential to each of the contacts 1401*a*-1401*f* and assess whether only a minimal resistance is present at each of the contacts. Such an operating state can comprise the monitored condition. In the event that the resistance detected at a contact is high, or above a threshold resistance, the microcontroller 1500 can deactivate that contact, more than one contact, or, alternatively, all of the contacts. Such an operating state can comprise the deactivated condition. If a shaft assembly is assembled to the handle assembly 14 and it is detected by the microcontroller 1500, as discussed above, the microcontroller 1500 can increase the voltage potential to the contacts 1401*a*-1401*f*. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 20:
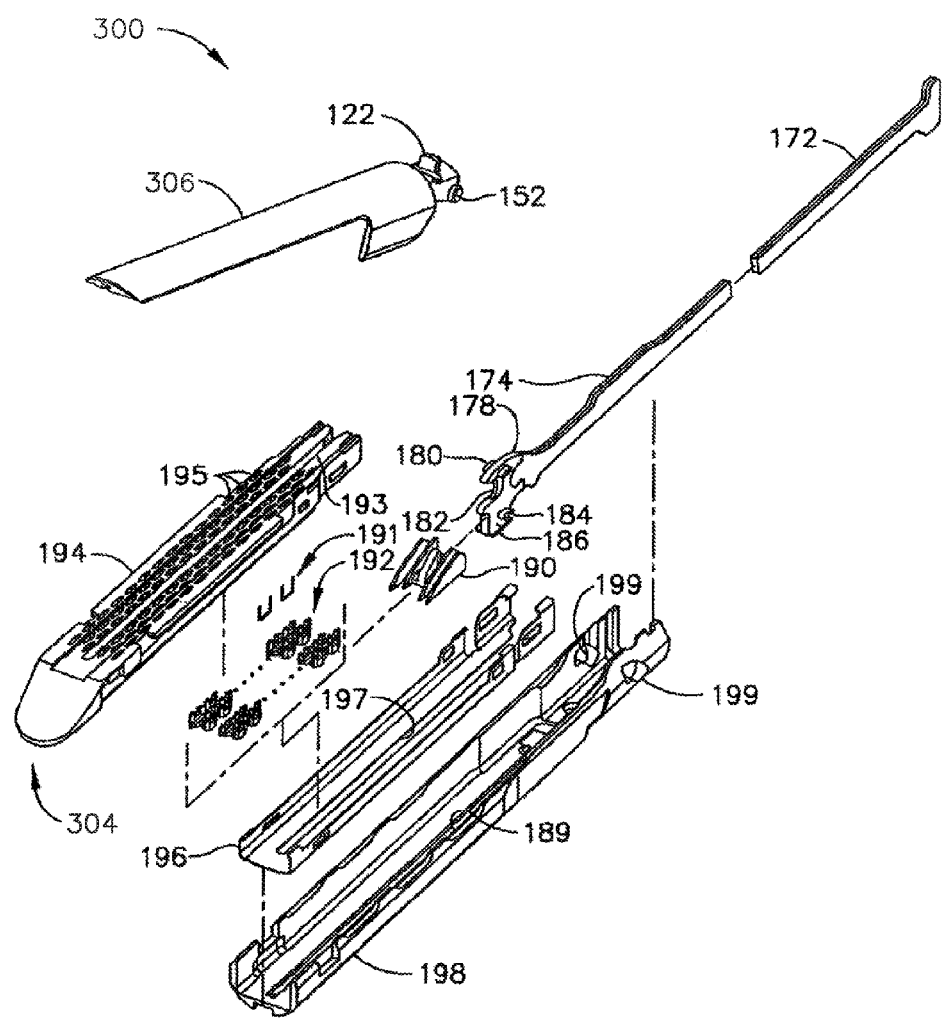
FIG. 20 is an exploded view of one aspect of an end effector of the surgical instrument of FIG. 1.

Referring to FIG. 20, a non-limiting form of the end effector 300 is illustrated. As described above, the end effector 300 may include the anvil 306 and the staple cartridge 304. In this non-limiting example, the anvil 306 is coupled to an elongate channel 198. For example, apertures 199 can be defined in the elongate channel 198 which can receive pins 152 extending from the anvil 306 and allow the anvil 306 to pivot from an open position to a closed position relative to the elongate channel 198 and staple cartridge 304. In addition, FIG. 20 shows a firing bar 172, configured to longitudinally translate into the end effector 300. The firing bar 172 may be constructed from one solid section, or in various examples, may include a laminate material comprising, for example, a stack of steel plates. A distally projecting end of the firing bar 172 can be attached to an E-beam 178 that can, among other things, assist in spacing the anvil 306 from a staple cartridge 304 positioned in the elongate channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 304. The staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 304. The wedge sled 190 upwardly cams the staple drivers 192 to force out the staples 191 into deforming contact with the anvil 306 while a cutting surface 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongate channel 198. When a staple cartridge 304 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 20, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the staple cartridge 304 as the firing bar 172 is moved distally to fire the staples from the staple cartridge 304 and/or incise the tissue captured between the anvil 306 and the staple cartridge 304. Thereafter, the firing bar 172 and the E-beam 178 can be retracted proximally allowing the anvil 306 to be opened to release the two stapled and severed tissue portions (not shown).

Figure 21A:
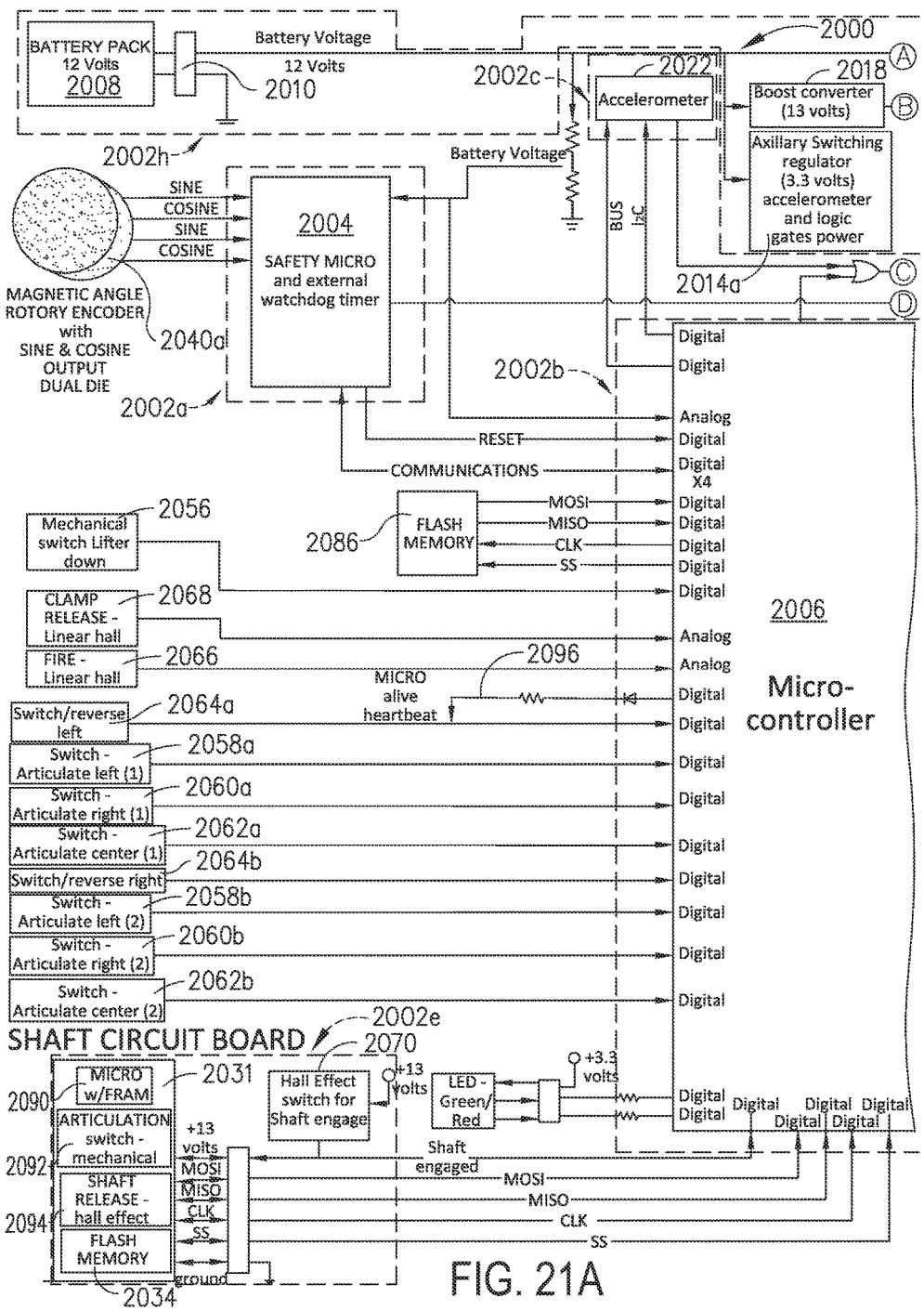
FIGS. 21A-21B is a circuit diagram of the surgical instrument of FIG. 1 spanning two drawings sheets.
Figure 21B:
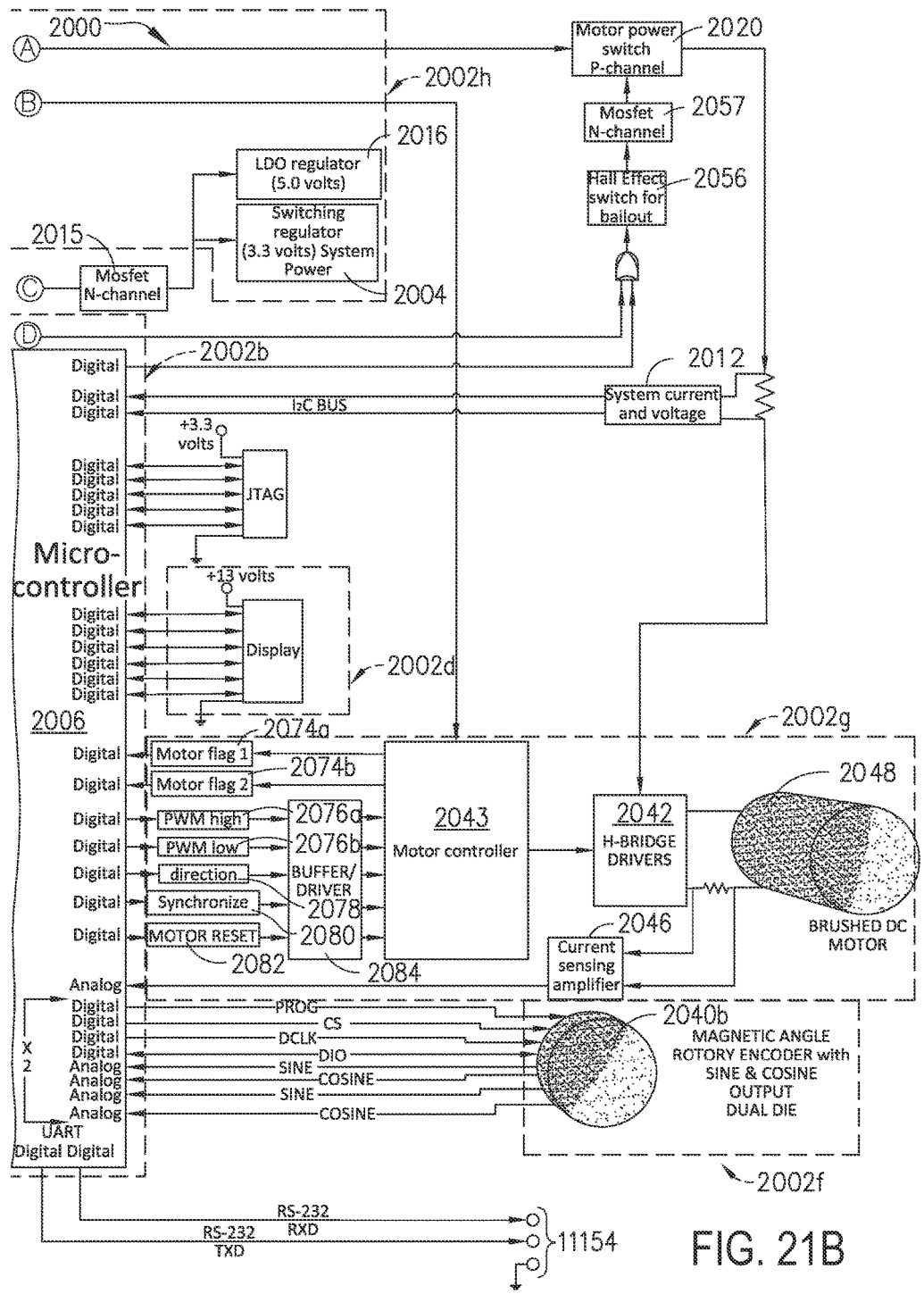

Having described a surgical instrument 10 (FIGS. 1-4) in general terms, the description now turns to a detailed description of various electrical/electronic components of the surgical instrument 10. Turning now to FIGS. 21A-21B, where one example of a segmented circuit 2000 comprising a plurality of circuit segments 2002a-2002g is illustrated. The segmented circuit 2000 comprising the plurality of circuit segments 2002a-2002g is configured to control a powered surgical instrument, such as, for example, the surgical instrument 10 illustrated in FIGS. 1-18A, without limitation. The plurality of circuit segments 2002a-2002g is configured to control one or more operations of the powered surgical instrument 10. A safety processor segment 2002a (Segment 1) comprises a safety processor 2004. A primary processor segment 2002b (Segment 2) comprises a primary processor 2006. The safety processor 2004 and/or the primary processor 2006 are configured to interact with one or more additional circuit segments 2002c-2002g to control operation of the powered surgical instrument 10. The primary processor 2006 comprises a plurality of inputs coupled to, for example, one or more circuit segments 2002c-2002g, a battery 2008, and/or a plurality of switches 2058a-2070. The segmented circuit 2000 may be implemented by any suitable circuit, such as, for example, a printed circuit board assembly (PCBA) within the powered surgical instrument 10. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one aspect, the main processor 2006 may be any single core or multicore processor such as those known under the trade name ARM Cortex by Texas Instruments. In one example, the safety processor 2004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one example, the safety processor 2004 may be configured specifically for IEC 61508 and ISO 26262 safety critical applications, among others, to provide advanced integrated safety features while delivering scalable performance, connectivity, and memory options.

In certain instances, the main processor 2006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other processors may be readily substituted and, accordingly, the present disclosure should not be limited in this context.

In one aspect, the segmented circuit 2000 comprises an acceleration segment 2002c (Segment 3). The acceleration segment 2002c comprises an acceleration sensor 2022. The acceleration sensor 2022 may comprise, for example, an accelerometer. The acceleration sensor 2022 is configured to detect movement or acceleration of the powered surgical instrument 10. In some examples, input from the acceleration sensor 2022 is used, for example, to transition to and from a sleep mode, identify an orientation of the powered surgical instrument, and/or identify when the surgical instrument has been dropped. In some examples, the acceleration segment 2002c is coupled to the safety processor 2004 and/or the primary processor 2006.

In one aspect, the segmented circuit 2000 comprises a display segment 2002d (Segment 4). The display segment 2002d comprises a display connector 2024 coupled to the primary processor 2006. The display connector 2024 couples the primary processor 2006 to a display 2028 through one or more display driver integrated circuits 2026. The display driver integrated circuits 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some examples, the display segment 2002d is coupled to the safety processor 2004.

In some aspects, the segmented circuit 2000 comprises a shaft segment 2002e (Segment 5). The shaft segment 2002e comprises one or more controls for a shaft 2004 coupled to the surgical instrument 10 and/or one or more controls for an end effector 2006 coupled to the shaft 2004. The shaft segment 2002e comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some examples, the shaft PCBA EEPROM 2034 comprises one or more parameters, routines, and/or programs specific to the shaft 2004 and/or the shaft PCBA 2031. The shaft PCBA 2031 may be coupled to the shaft 2004 and/or integral with the surgical instrument 10. In some examples, the shaft segment 2002e comprises a second shaft EEPROM 2038. The second shaft EEPROM 2038 comprises a plurality of algorithms, routines, parameters, and/or other data corresponding to one or more shafts 2004 and/or end effectors 2006 which may be interfaced with the powered surgical instrument 10.

In some aspects, the segmented circuit 2000 comprises a position encoder segment 2002f (Segment 6). The position encoder segment 2002f comprises one or more magnetic rotary position encoders 2040a-2040b. The one or more magnetic rotary position encoders 2040a-2040b are configured to identify the rotational position of a motor 2048, a shaft 2004, and/or an end effector 2006 of the surgical instrument 10. In some examples, the magnetic rotary position encoders 2040a-2040b may be coupled to the safety processor 2004 and/or the primary processor 2006.

In some aspects, the segmented circuit 2000 comprises a motor segment 2002g (Segment 7). The motor segment 2002g comprises a motor 2048 configured to control one or more movements of the powered surgical instrument 10. The motor 2048 is coupled to the primary processor 2006 by an H-Bridge driver 2042 and one or more H-bridge field-effect transistors (FETs) 2044. The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some examples, the motor 2048 is coupled to a motor electromagnetic interference (EMI) filter 2050.

In some aspects, the segmented circuit 2000 comprises a power segment 2002h (Segment 8). A battery 2008 is coupled to the safety processor 2004, the primary processor 2006, and one or more of the additional circuit segments 2002c-2002g. The battery 2008 is coupled to the segmented circuit 2000 by a battery connector 2010 and a current sensor 2012. The current sensor 2012 is configured to measure the total current draw of the segmented circuit 2000. In some examples, one or more voltage converters 2014a, 2014b, 2016 are configured to provide predetermined voltage values to one or more circuit segments 2002a-2002g. For example, in some examples, the segmented circuit 2000 may comprise 3.3V voltage converters 2014a-2014b and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some aspects, the safety segment 2002a comprises a motor power interrupt 2020. The motor power interrupt 2020 is coupled between the power segment 2002h and the motor segment 2002g. The safety segment 2002a is configured to interrupt power to the motor segment 2002g when an error or fault condition is detected by the safety processor 2004 and/or the primary processor 2006 as discussed in more detail herein. Although the circuit segments 2002a-2002g are illustrated with all components of the circuit segments 2002a-2002h located in physical proximity, one skilled in the art will recognize that a circuit segment 2002a-2002h may comprise components physically and/or electrically separate from other components of the same circuit segment 2002a-2002g. In some examples, one or more components may be shared between two or more circuit segments 2002a-2002g.

In some aspects, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058a, a left side articulation right switch 2060a, a left side articulation center switch 2062a, a right side articulation left switch 2058b, a right side articulation right switch 2060b, and a right side articulation center switch 2062b are configured to control articulation of a shaft 2004 and/or an end effector 2006. A left side reverse switch 2064a and a right side reverse switch 2064b are coupled to the primary processor 2006. In some examples, the left side switches comprising the left side articulation left switch 2058a, the left side articulation right switch 2060a, the left side articulation center switch 2062a, and the left side reverse switch 2064a are coupled to the primary processor 2006 by a left flex connector 2072a. The right side switches comprising the right side articulation left switch 2058b, the right side articulation right switch 2060b, the right side articulation center switch 2062b, and the right side reverse switch 2064b are coupled to the primary processor 2006 by a right flex connector 2072b. In some examples, a firing switch 2066, a clamp release switch 2068, and a shaft engaged switch 2070 are coupled to the primary processor 2006.

In some aspects, the plurality of switches 2056-2070 may comprise, for example, a plurality of handle controls mounted to a handle of the surgical instrument 10, a plurality of indicator switches, and/or any combination thereof. In various examples, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some examples, additional or fewer switches may be coupled to the segmented circuit 2000, one or more of the switches 2056-2070 may be combined into a single switch, and/or expanded to multiple switches. For example, in one example, one or more of the left side and/or right side articulation switches 2058a-2064b may be combined into a single multi-position switch.

In one aspect, the safety processor 2004 is configured to implement a watchdog function, among other safety operations. The safety processor 2004 and the primary processor 2006 of the segmented circuit 2000 are in signal communication. A microprocessor alive heartbeat signal is provided at output 2096. The acceleration segment 2002c comprises an accelerometer 2022 configured to monitor movement of the surgical instrument 10. In various examples, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration $g=9.8$ m/s$^2$ (gravity) straight upwards, due to its weight. Another type of acceleration that accelerometer 2022 can measure is g-force acceleration. In various other examples, the accelerometer 2022 may comprise a single, double, or triple axis accelerometer. Further, the acceleration segment 2002c may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one aspect, the safety processor 2004 is configured to implement a watchdog function with respect to one or more circuit segments 2002c-2002h, such as, for example, the motor segment 2002g. In this regards, the safety processor 2004 employs the watchdog function to detect and recover from malfunctions of the primary processor 2006. During normal operation, the safety processor 2004 monitors for hardware faults or program errors of the primary processor 2004 and to initiate corrective action or actions. The corrective actions may include placing the primary processor 2006 in a safe state and restoring normal system operation. In one example, the safety processor 2004 is coupled to at least a first sensor. The first sensor measures a first property of the surgical instrument 10 (FIGS. 1-4). In some examples, the safety processor 2004 is configured to compare the measured property of the surgical instrument 10 to a predetermined value. For example, in one example, a motor sensor 2040a is coupled to the safety processor 2004. The motor sensor 2040a provides motor speed and position information to the safety processor 2004. The safety processor 2004 monitors the motor sensor 2040a and compares the value to a maximum speed and/or position value and prevents operation of the motor 2048 above the predetermined values. In some examples, the predetermined values are calculated based on real-time speed and/or position of the motor 2048, calculated from values supplied by a second motor sensor 2040b in communication with the primary processor 2006, and/or provided to the safety processor 2004 from, for example, a memory module coupled to the safety processor 2004.

In some aspects, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002c-2002h, such as, for example, the motor segment 2002g. For example, in the example illustrated in FIGS. 21A-21B, the safety processor 2004 is coupled to a first motor position sensor 2040a and the primary processor 2006 is coupled to a second motor position sensor 2040b. The motor position sensors 2040a, 2040b may comprise any suitable motor position sensor, such as, for example, a magnetic angle rotary input comprising a sine and cosine output. The motor position sensors 2040a, 2040b provide respective signals to the safety processor 2004 and the primary processor 2006 indicative of the position of the motor 2048.

The safety processor 2004 and the primary processor 2006 generate an activation signal when the values of the first motor sensor 2040a and the second motor sensor 2040b are within a predetermined range. When either the primary processor 2006 or the safety processor 2004 to detect a value outside of the predetermined range, the activation signal is terminated and operation of at least one circuit segment 2002c-2002h, such as, for example, the motor segment 2002g, is interrupted and/or prevented. For example, in some examples, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the motor sensors 2040a, 2040b within the predetermined range. When either of the motor sensors 2040a, 2040b detect a value outside of the predetermined range, the activation signal from that motor sensor 2040a, 2040b is set low, and the output of the AND gate is set low, opening the motor power switch 2020. In some examples, the value of the first sensor 2040a and the second sensor 2040b is compared, for example, by the safety processor 2004 and/or the primary processor 2006. When the values of the first sensor and the second sensor are different, the safety processor 2004 and/or the primary processor 2006 may prevent operation of the motor segment 2002g.

In some aspects, the safety processor 2004 receives a signal indicative of the value of the second sensor 2040b and compares the second sensor value to the first sensor value. For example, in one aspect, the safety processor 2004 is coupled directly to a first motor sensor 2040a. A second motor sensor 2040b is coupled to a primary processor 2006, which provides the second motor sensor 2040b value to the safety processor 2004, and/or coupled directly to the safety processor 2004. The safety processor 2004 compares the value of the first motor sensor 2040 to the value of the second motor sensor 2040b. When the safety processor 2004 detects a mismatch between the first motor sensor 2040a and the second motor sensor 2040b, the safety processor 2004 may interrupt operation of the motor segment 2002g, for example, by cutting power to the motor segment 2002g.

In some aspects, the safety processor 2004 and/or the primary processor 2006 is coupled to a first sensor 2040a configured to measure a first property of a surgical instrument and a second sensor 2040b configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002g when a fault is detected.

In one aspect, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one example, the safety processor 2004 is reprogrammed with new parameters and/or safety algorithms each time a new shaft and/or end effector is coupled to the surgical instrument 10. In some examples, one or more safety values stored by the safety processor 2004 are duplicated by the primary processor 2006. Two-way error detection is performed to ensure values and/or parameters stored by either of the processors 2004, 2006 are correct.

In some aspects, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some examples, communication between the safety processor 2004 and the primary processor 2006 occurs at a predetermined interval. The predetermined interval may be constant or may be variable based on the circuit state and/or operation of the surgical instrument 10.

Figure 22:
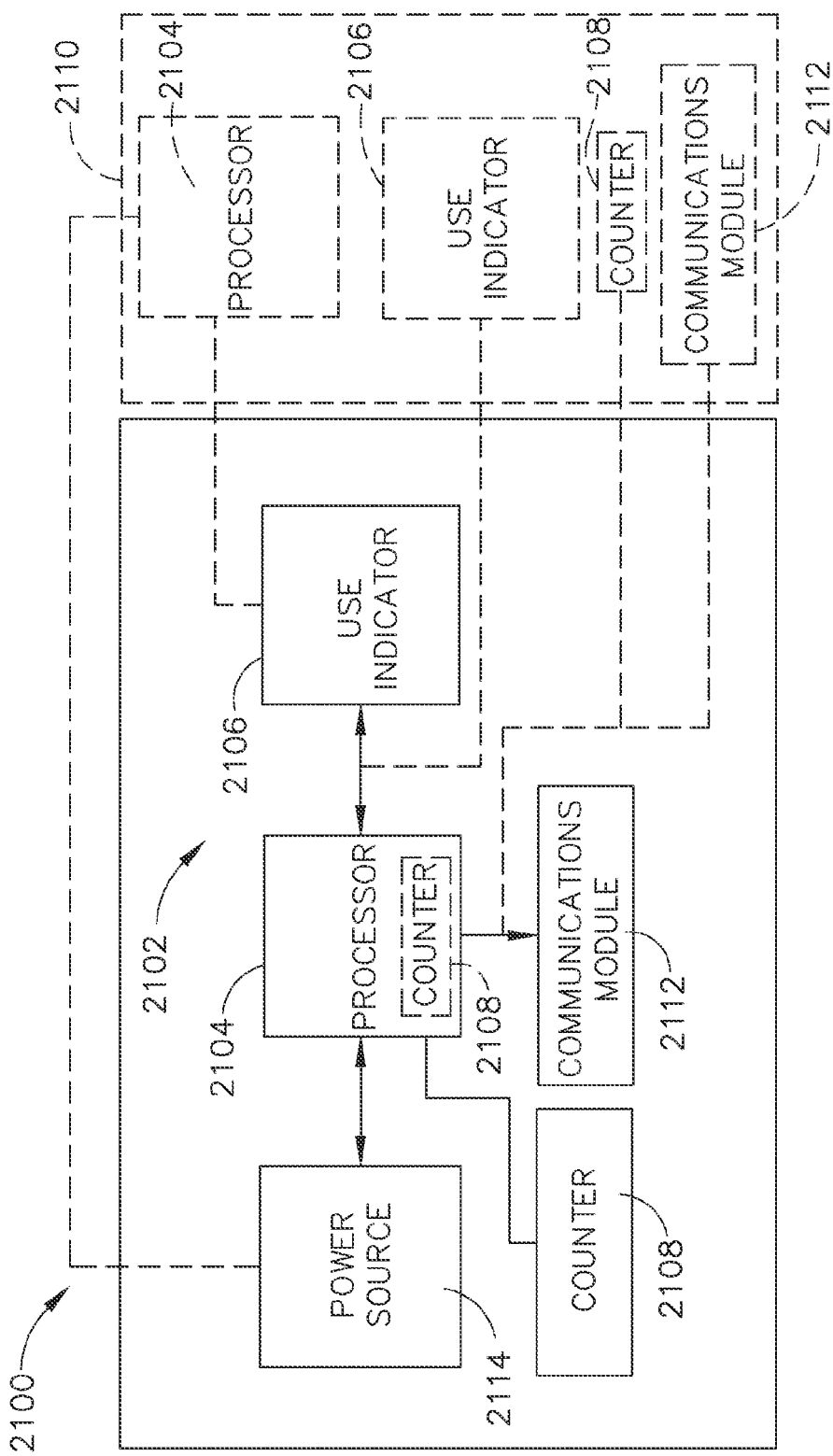
FIG. 22 illustrates one instance of a power assembly comprising a usage cycle circuit configured to generate a usage cycle count of the battery back.

FIG. 22 illustrates one example of a power assembly 2100 comprising a usage cycle circuit 2102 configured to monitor a usage cycle count of the power assembly 2100. The power assembly 2100 may be coupled to a surgical instrument 2110. The usage cycle circuit 2102 comprises a processor 2104 and a use indicator 2106. The use indicator 2106 is configured to provide a signal to the processor 2104 to indicate a use of the battery back 2100 and/or a surgical instrument 2110 coupled to the power assembly 2100. A "use" may comprise any suitable action, condition, and/or parameter such as, for example, changing a modular component of a surgical instrument 2110, deploying or firing a disposable component coupled to the surgical instrument 2110, delivering electrosurgical energy from the surgical instrument 2110, reconditioning the surgical instrument 2110 and/or the power assembly 2100, exchanging the power assembly 2100, recharging the power assembly 2100, and/or exceeding a safety limitation of the surgical instrument 2110 and/or the battery back 2100.

In some instances, a usage cycle, or use, is defined by one or more power assembly 2100 parameters. For example, in one instance, a usage cycle comprises using more than 5% of the total energy available from the power assembly 2100 when the power assembly 2100 is at a full charge level. In another instance, a usage cycle comprises a continuous energy drain from the power assembly 2100 exceeding a predetermined time limit. For example, a usage cycle may correspond to five minutes of continuous and/or total energy draw from the power assembly 2100. In some instances, the power assembly 2100 comprises a usage cycle circuit 2102 having a continuous power draw to maintain one or more components of the usage cycle circuit 2102, such as, for example, the use indicator 2106 and/or a counter 2108, in an active state.

The processor 2104 maintains a usage cycle count. The usage cycle count indicates the number of uses detected by the use indicator 2106 for the power assembly 2100 and/or the surgical instrument 2110. The processor 2104 may increment and/or decrement the usage cycle count based on input from the use indicator 2106. The usage cycle count is used to control one or more operations of the power assembly 2100 and/or the surgical instrument 2110. For example, in some instances, a power assembly 2100 is disabled when the usage cycle count exceeds a predetermined usage limit Although the instances discussed herein are discussed with respect to incrementing the usage cycle count above a predetermined usage limit, those skilled in the art will recognize that the usage cycle count may start at a predetermined amount and may be decremented by the processor 2104. In this instance, the processor 2104 initiates and/or prevents one or more operations of the power assembly 2100 when the usage cycle count falls below a predetermined usage limit.

The usage cycle count is maintained by a counter 2108. The counter 2108 comprises any suitable circuit, such as, for example, a memory module, an analog counter, and/or any circuit configured to maintain a usage cycle count. In some instances, the counter 2108 is formed integrally with the processor 2104. In other instances, the counter 2108 comprises a separate component, such as, for example, a solid state memory module. In some instances, the usage cycle count is provided to a remote system, such as, for example, a central database. The usage cycle count is transmitted by a communications module 2112 to the remote system. The communications module 2112 is configured to use any suitable communications medium, such as, for example, wired and/or wireless communication. In some instances, the communications module 2112 is configured to receive one or more instructions from the remote system, such as, for example, a control signal when the usage cycle count exceeds the predetermined usage limit.

In some instances, the use indicator 2106 is configured to monitor the number of modular components used with a surgical instrument 2110 coupled to the power assembly 2100. A modular component may comprise, for example, a modular shaft, a modular end effector, and/or any other modular component. In some instances, the use indicator 2106 monitors the use of one or more disposable components, such as, for example, insertion and/or deployment of a staple cartridge within an end effector coupled to the surgical instrument 2110. The use indicator 2106 comprises one or more sensors for detecting the exchange of one or more modular and/or disposable components of the surgical instrument 2110.

In some instances, the use indicator 2106 is configured to monitor single patient surgical procedures performed while the power assembly 2100 is installed. For example, the use indicator 2106 may be configured to monitor firings of the surgical instrument 2110 while the power assembly 2100 is coupled to the surgical instrument 2110. A firing may correspond to deployment of a staple cartridge, application of electrosurgical energy, and/or any other suitable surgical event. The use indicator 2106 may comprise one or more circuits for measuring the number of firings while the power assembly 2100 is installed. The use indicator 2106 provides a signal to the processor 2104 when a single patient procedure is performed and the processor 2104 increments the usage cycle count.

In some instances, the use indicator 2106 comprises a circuit configured to monitor one or more parameters of the power source 2114, such as, for example, a current draw from the power source 2114. The one or more parameters of the power source 2114 correspond to one or more operations performable by the surgical instrument 2110, such as, for example, a cutting and sealing operation. The use indicator 2106 provides the one or more parameters to the processor 2104, which increments the usage cycle count when the one or more parameters indicate that a procedure has been performed.

In some instances, the use indicator 2106 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2100 is coupled to the surgical instrument 2110, the processor 2104 polls the use indicator 2106 to determine when the single patient procedure time has expired. When the predetermined time period has elapsed, the processor 2104 increments the usage cycle count. After incrementing the usage cycle count, the processor 2104 resets the timing circuit of the use indicator 2106.

In some instances, the use indicator 2106 comprises a time constant that approximates the single patient procedure time. In one example, the usage cycle circuit 2102 comprises a resistor-capacitor (RC) timing circuit 2506. The RC timing circuit comprises a time constant defined by a resistor-capacitor pair. The time constant is defined by the values of the resistor and the capacitor. In one example, the usage cycle circuit 2552 comprises a rechargeable battery and a clock. When the power assembly 2100 is installed in a surgical instrument, the rechargeable battery is charged by the power source. The rechargeable battery comprises enough power to run the clock for at least the single patient procedure time. The clock may comprise a real time clock, a processor configured to implement a time function, or any other suitable timing circuit.

Referring still to FIG. 22, in some instances, the use indicator 2106 comprises a sensor configured to monitor one or more environmental conditions experienced by the power assembly 2100. For example, the use indicator 2106 may comprise an accelerometer. The accelerometer is configured to monitor acceleration of the power assembly 2100. The power assembly 2100 comprises a maximum acceleration tolerance. Acceleration above a predetermined threshold indicates, for example, that the power assembly 2100 has been dropped. When the use indicator 2106 detects acceleration above the maximum acceleration tolerance, the processor 2104 increments a usage cycle count. In some instances, the use indicator 2106 comprises a moisture sensor. The moisture sensor is configured to indicate when the power assembly 2100 has been exposed to moisture. The moisture sensor may comprise, for example, an immersion sensor configured to indicate when the power assembly 2100 has been fully immersed in a cleaning fluid, a moisture sensor configured to indicate when moisture is in contact with the power assembly 2100 during use, and/or any other suitable moisture sensor.

In some instances, the use indicator 2106 comprises a chemical exposure sensor. The chemical exposure sensor is configured to indicate when the power assembly 2100 has come into contact with harmful and/or dangerous chemicals. For example, during a sterilization procedure, an inappropriate chemical may be used that leads to degradation of the power assembly 2100. The processor 2104 increments the usage cycle count when the use indicator 2106 detects an inappropriate chemical.

In some instances, the usage cycle circuit 2102 is configured to monitor the number of reconditioning cycles experienced by the power assembly 2100. A reconditioning cycle may comprise, for example, a cleaning cycle, a sterilization cycle, a charging cycle, routine and/or preventative maintenance, and/or any other suitable reconditioning cycle. The use indicator 2106 is configured to detect a reconditioning cycle. For example, the use indicator 2106 may comprise a moisture sensor to detect a cleaning and/or sterilization cycle. In some instances, the usage cycle circuit 2102 monitors the number of reconditioning cycles experienced by the power assembly 2100 and disables the power assembly 2100 after the number of reconditioning cycles exceeds a predetermined threshold.

The usage cycle circuit 2102 may be configured to monitor the number of power assembly 2100 exchanges. The usage cycle circuit 2102 increments the usage cycle count each time the power assembly 2100 is exchanged. When the maximum number of exchanges is exceeded the usage cycle circuit 2102 locks out the power assembly 2100 and/or the surgical instrument 2110. In some instances, when the power assembly 2100 is coupled the surgical instrument 2110, the usage cycle circuit 2102 identifies the serial number of the power assembly 2100 and locks the power assembly 2100 such that the power assembly 2100 is usable only with the surgical instrument 2110. In some instances, the usage cycle circuit 2102 increments the usage cycle each time the power assembly 2100 is removed from and/or coupled to the surgical instrument 2110.

In some instances, the usage cycle count corresponds to sterilization of the power assembly 2100. The use indicator 2106 comprises a sensor configured to detect one or more parameters of a sterilization cycle, such as, for example, a temperature parameter, a chemical parameter, a moisture parameter, and/or any other suitable parameter. The processor 2104 increments the usage cycle count when a sterilization parameter is detected. The usage cycle circuit 2102 disables the power assembly 2100 after a predetermined number of sterilizations. In some instances, the usage cycle circuit 2102 is reset during a sterilization cycle, a voltage sensor to detect a recharge cycle, and/or any suitable sensor. The processor 2104 increments the usage cycle count when a reconditioning cycle is detected. The usage cycle circuit 2102 is disabled when a sterilization cycle is detected. The usage cycle circuit 2102 is reactivated and/or reset when the power assembly 2100 is coupled to the surgical instrument 2110. In some instances, the use indicator comprises a zero power indicator. The zero power indicator changes state during a sterilization cycle and is checked by the processor 2104 when the power assembly 2100 is coupled to a surgical instrument 2110. When the zero power indicator indicates that a sterilization cycle has occurred, the processor 2104 increments the usage cycle count.

A counter 2108 maintains the usage cycle count. In some instances, the counter 2108 comprises a non-volatile memory module. The processor 2104 increments the usage cycle count stored in the non-volatile memory module each time a usage cycle is detected. The memory module may be accessed by the processor 2104 and/or a control circuit, such as, for example, the control circuit 200. When the usage cycle count exceeds a predetermined threshold, the processor 2104 disables the power assembly 2100. In some instances, the usage cycle count is maintained by a plurality of circuit components. For example, in one instance, the counter 2108 comprises a resistor (or fuse) pack. After each use of the power assembly 2100, a resistor (or fuse) is burned to an open position, changing the resistance of the resistor pack. The power assembly 2100 and/or the surgical instrument 2110 reads the remaining resistance. When the last resistor of the resistor pack is burned out, the resistor pack has a predetermined resistance, such as, for example, an infinite resistance corresponding to an open circuit, which indicates that the power assembly 2100 has reached its usage limit. In some instances, the resistance of the resistor pack is used to derive the number of uses remaining.

In some instances, the usage cycle circuit 2102 prevents further use of the power assembly 2100 and/or the surgical instrument 2110 when the usage cycle count exceeds a predetermined usage limit. In one instance, the usage cycle count associated with the power assembly 2100 is provided to an operator, for example, utilizing a screen formed integrally with the surgical instrument 2110. The surgical instrument 2110 provides an indication to the operator that the usage cycle count has exceeded a predetermined limit for the power assembly 2100, and prevents further operation of the surgical instrument 2110.

In some instances, the usage cycle circuit 2102 is configured to physically prevent operation when the predetermined usage limit is reached. For example, the power assembly 2100 may comprise a shield configured to deploy over contacts of the power assembly 2100 when the usage cycle count exceeds the predetermined usage limit. The shield prevents recharge and use of the power assembly 2100 by covering the electrical connections of the power assembly 2100.

In some instances, the usage cycle circuit 2102 is located at least partially within the surgical instrument 2110 and is configured to maintain a usage cycle count for the surgical instrument 2110. FIG. 22 illustrates one or more components of the usage cycle circuit 2102 within the surgical instrument 2110 in phantom, illustrating the alternative positioning of the usage cycle circuit 2102. When a predetermined usage limit of the surgical instrument 2110 is exceeded, the usage cycle circuit 2102 disables and/or prevents operation of the surgical instrument 2110. The usage cycle count is incremented by the usage cycle circuit 2102 when the use indicator 2106 detects a specific event and/or requirement, such as, for example, firing of the surgical instrument 2110, a predetermined time period corresponding to a single patient procedure time, based on one or more motor parameters of the surgical instrument 2110, in response to a system diagnostic indicating that one or more predetermined thresholds are met, and/or any other suitable requirement. As discussed above, in some instances, the use indicator 2106 comprises a timing circuit corresponding to a single patient procedure time. In other instances, the use indicator 2106 comprises one or more sensors configured to detect a specific event and/or condition of the surgical instrument 2110.

In some instances, the usage cycle circuit 2102 is configured to prevent operation of the surgical instrument 2110 after the predetermined usage limit is reached. In some instances, the surgical instrument 2110 comprises a visible indicator to indicate when the predetermined usage limit has been reached and/or exceeded. For example, a flag, such as a red flag, may pop-up from the surgical instrument 2110, such as from the handle, to provide a visual indication to the operator that the surgical instrument 2110 has exceeded the predetermined usage limit. As another example, the usage cycle circuit 2102 may be coupled to a display formed integrally with the surgical instrument 2110. The usage cycle circuit 2102 displays a message indicating that the predetermined usage limit has been exceeded. The surgical instrument 2110 may provide an audible indication to the operator that the predetermined usage limit has been exceeded. For example, in one instance, the surgical instrument 2110 emits an audible tone when the predetermined usage limit is exceeded and the power assembly 2100 is removed from the surgical instrument 2110. The audible tone indicates the last use of the surgical instrument 2110 and indicates that the surgical instrument 2110 should be disposed or reconditioned.

In some instances, the usage cycle circuit 2102 is configured to transmit the usage cycle count of the surgical instrument 2110 to a remote location, such as, for example, a central database. The usage cycle circuit 2102 comprises a communications module 2112 configured to transmit the usage cycle count to the remote location. The communications module 2112 may utilize any suitable communications system, such as, for example, wired or wireless communications system. The remote location may comprise a central database configured to maintain usage information. In some instances, when the power assembly 2100 is coupled to the surgical instrument 2110, the power assembly 2100 records a serial number of the surgical instrument 2110. The serial number is transmitted to the central database, for example, when the power assembly 2100 is coupled to a charger. In some instances, the central database maintains a count corresponding to each use of the surgical instrument 2110. For example, a bar code associated with the surgical instrument 2110 may be scanned each time the surgical instrument 2110 is used. When the use count exceeds a predetermined usage limit, the central database provides a signal to the surgical instrument 2110 indicating that the surgical instrument 2110 should be discarded.

The surgical instrument 2110 may be configured to lock and/or prevent operation of the surgical instrument 2110 when the usage cycle count exceeds a predetermined usage limit. In some instances, the surgical instrument 2110 comprises a disposable instrument and is discarded after the usage cycle count exceeds the predetermined usage limit. In other instances, the surgical instrument 2110 comprises a reusable surgical instrument which may be reconditioned after the usage cycle count exceeds the predetermined usage limit. The surgical instrument 2110 initiates a reversible lockout after the predetermined usage limit is met. A technician reconditions the surgical instrument 2110 and releases the lockout, for example, utilizing a specialized technician key configured to reset the usage cycle circuit 2102.

Figure 23:
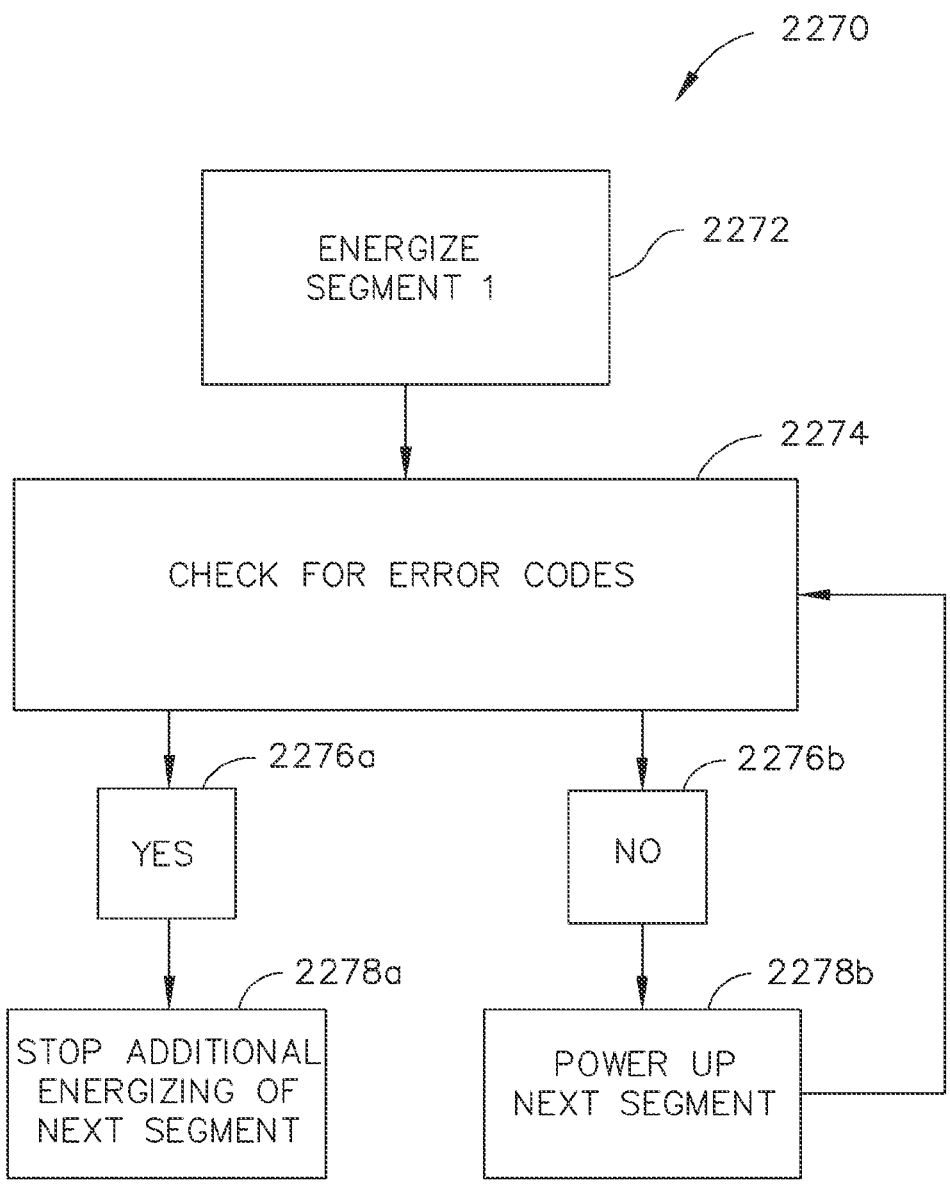
FIG. 23 illustrates one aspect of a process for sequentially energizing a segmented circuit.

In some aspects, the segmented circuit 2000 is configured for sequential start-up. An error check is performed by each circuit segment 2002a-2002g prior to energizing the next sequential circuit segment 2002a-2002g. FIG. 23 illustrates one example of a process for sequentially energizing a segmented circuit 2270, such as, for example, the segmented circuit 2000. When a battery 2008 is coupled to the segmented circuit 2000, the safety processor 2004 is energized 2272. The safety processor 2004 performs a self-error check 2274. When an error is detected 2276a, the safety processor stops energizing the segmented circuit 2000 and generates an error code 2278a. When no errors are detected 2276b, the safety processor 2004 initiates 2278b power-up of the primary processor 2006. The primary processor 2006 performs a self-error check. When no errors are detected, the primary processor 2006 begins sequential power-up of each of the remaining circuit segments 2278b. Each circuit segment is energized and error checked by the primary processor 2006. When no errors are detected, the next circuit segment is energized 2278b. When an error is detected, the safety processor 2004 and/or the primary process stops energizing the current segment and generates an error 2278a. The sequential start-up continues until all of the circuit segments 2002a-2002g have been energized. In some examples, the segmented circuit 2000 transitions from sleep mode following a similar sequential power-up process 11250.

Figure 24:
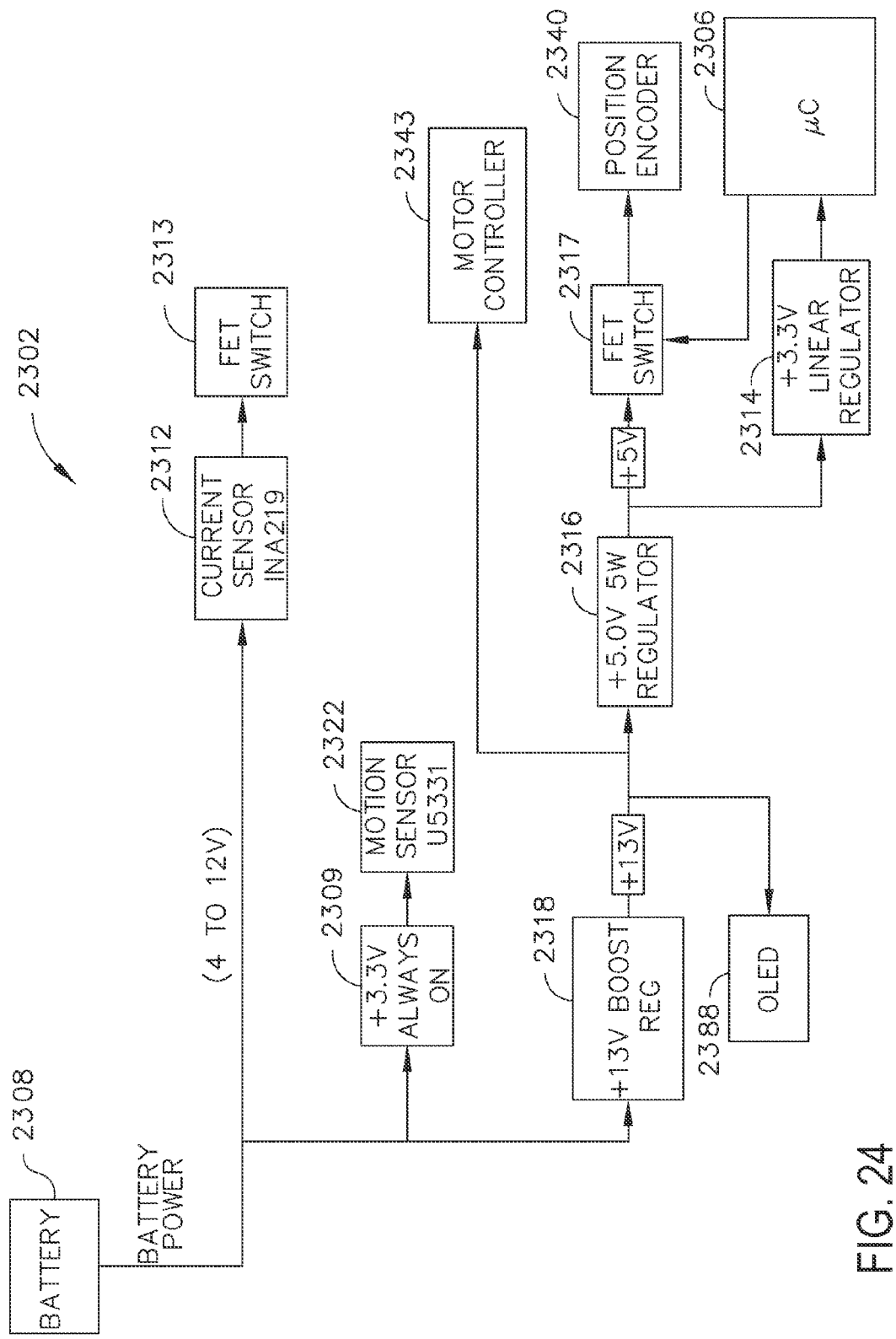
FIG. 24 illustrates one aspect of a power segment comprising a plurality of daisy chained power converters.

FIG. 24 illustrates one aspect of a power segment 2302 comprising a plurality of daisy chained power converters 2314, 2316, 2318. The power segment 2302 comprises a battery 2308. The battery 2308 is configured to provide a source voltage, such as, for example, 12V. A current sensor 2312 is coupled to the battery 2308 to monitor the current draw of a segmented circuit and/or one or more circuit segments. The current sensor 2312 is coupled to an FET switch 2313. The battery 2308 is coupled to one or more voltage converters 2309, 2314, 2316. An always on converter 2309 provides a constant voltage to one or more circuit components, such as, for example, a motion sensor 2322. The always on converter 2309 comprises, for example, a 3.3V converter. The always on converter 2309 may provide a constant voltage to additional circuit components, such as, for example, a safety processor (not shown). The battery 2308 is coupled to a boost converter 2318. The boost converter 2318 is configured to provide a boosted voltage above the voltage provided by the battery 2308. For example, in the illustrated example, the battery 2308 provides a voltage of 12V. The boost converter 2318 is configured to boost the voltage to 13V. The boost converter 2318 is configured to maintain a minimum voltage during operation of a surgical instrument, for example, the surgical instrument 10 (FIGS. 1-4). Operation of a motor can result in the power provided to the primary processor 2306 dropping below a minimum threshold and creating a brownout or reset condition in the primary processor 2306. The boost converter 2318 ensures that sufficient power is available to the primary processor 2306 and/or other circuit components, such as the motor controller 2343, during operation of the surgical instrument 10. In some examples, the boost converter 2318 is coupled directly one or more circuit components, such as, for example, an OLED display 2388.

The boost converter 2318 is coupled to one or more step-down converters to provide voltages below the boosted voltage level. A first voltage converter 2316 is coupled to the boost converter 2318 and provides a first stepped-down voltage to one or more circuit components. In the illustrated example, the first voltage converter 2316 provides a voltage of 5V. The first voltage converter 2316 is coupled to a rotary position encoder 2340. A FET switch 2317 is coupled between the first voltage converter 2316 and the rotary position encoder 2340. The FET switch 2317 is controlled by the processor 2306. The processor 2306 opens the FET switch 2317 to deactivate the position encoder 2340, for example, during power intensive operations. The first voltage converter 2316 is coupled to a second voltage converter 2314 configured to provide a second stepped-down voltage. The second stepped-down voltage comprises, for example, 3.3V. The second voltage converter 2314 is coupled to a processor 2306. In some examples, the boost converter 2318, the first voltage converter 2316, and the second voltage converter 2314 are coupled in a daisy chain configuration. The daisy chain configuration allows the use of smaller, more efficient converters for generating voltage levels below the boosted voltage level. The examples, however, are not limited to the particular voltage range(s) described in the context of this specification.

Figure 25:
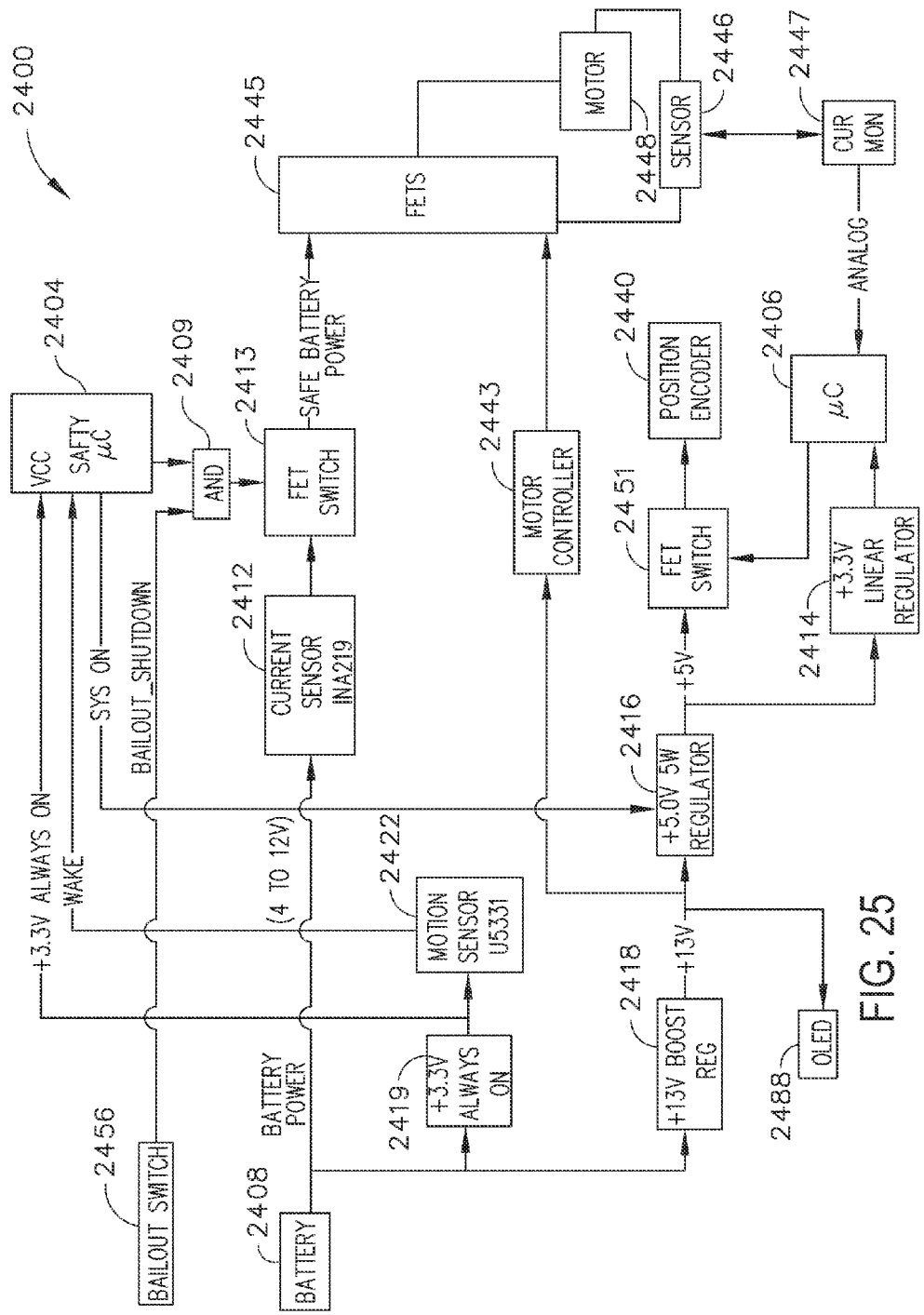
FIG. 25 illustrates one aspect of a segmented circuit configured to maximize power available for critical and/or power intense functions.

FIG. 25 illustrates one aspect of a segmented circuit 2400 configured to maximize power available for critical and/or power intense functions. The segmented circuit 2400 comprises a battery 2408. The battery 2408 is configured to provide a source voltage such as, for example, 12V. The source voltage is provided to a plurality of voltage converters 2409, 2418. An always-on voltage converter 2409 provides a constant voltage to one or more circuit components, for example, a motion sensor 2422 and a safety processor 2404. The always-on voltage converter 2409 is directly coupled to the battery 2408. The always-on converter 2409 provides a voltage of 3.3V, for example. The examples, however, are not limited to the particular voltage range(s) described in the context of this specification.

The segmented circuit 2400 comprises a boost converter 2418. The boost converter 2418 provides a boosted voltage above the source voltage provided by the battery 2408, such as, for example, 13V. The boost converter 2418 provides a boosted voltage directly to one or more circuit components, such as, for example, an OLED display 2488 and a motor controller 2443. By coupling the OLED display 2488 directly to the boost converter 2418, the segmented circuit 2400 eliminates the need for a power converter dedicated to the OLED display 2488. The boost converter 2418 provides a boosted voltage to the motor controller 2443 and the motor 2448 during one or more power intensive operations of the motor 2448, such as, for example, a cutting operation. The boost converter 2418 is coupled to a step-down converter 2416. The step-down converter 2416 is configured to provide a voltage below the boosted voltage to one or more circuit components, such as, for example, 5V. The step-down converter 2416 is coupled to, for example, a FET switch 2451 and a position encoder 2440. The FET switch 2451 is coupled to the primary processor 2406. The primary processor 2406 opens the FET switch 2451 when transitioning the segmented circuit 2400 to sleep mode and/or during power intensive functions requiring additional voltage delivered to the motor 2448. Opening the FET switch 2451 deactivates the position encoder 2440 and eliminates the power draw of the position encoder 2440. The examples, however, are not limited to the particular voltage range(s) described in the context of this specification.

The step-down converter 2416 is coupled to a linear converter 2414. The linear converter 2414 is configured to provide a voltage of, for example, 3.3V. The linear converter 2414 is coupled to the primary processor 2406. The linear converter 2414 provides an operating voltage to the primary processor 2406. The linear converter 2414 may be coupled to one or more additional circuit components. The examples, however, are not limited to the particular voltage range(s) described in the context of this specification.

The segmented circuit 2400 comprises a bailout switch 2456. The bailout switch 2456 is coupled to a bailout door on the surgical instrument 10. The bailout switch 2456 and the safety processor 2404 are coupled to an AND gate 2419. The AND gate 2419 provides an input to a FET switch 2413. When the bailout switch 2456 detects a bailout condition, the bailout switch 2456 provides a bailout shutdown signal to the AND gate 2419. When the safety processor 2404 detects an unsafe condition, such as, for example, due to a sensor mismatch, the safety processor 2404 provides a shutdown signal to the AND gate 2419. In some examples, both the bailout shutdown signal and the shutdown signal are high during normal operation and are low when a bailout condition or an unsafe condition is detected. When the output of the AND gate 2419 is low, the FET switch 2413 is opened and operation of the motor 2448 is prevented. In some examples, the safety processor 2404 utilizes the shutdown signal to transition the motor 2448 to an off state in sleep mode. A third input to the FET switch 2413 is provided by a current sensor 2412 coupled to the battery 2408. The current sensor 2412 monitors the current drawn by the circuit 2400 and opens the FET switch 2413 to shut-off power to the motor 2448 when an electrical current above a predetermined threshold is detected. The FET switch 2413 and the motor controller 2443 are coupled to a bank of FET switches 2445 configured to control operation of the motor 2448.

A motor current sensor 2446 is coupled in series with the motor 2448 to provide a motor current sensor reading to a current monitor 2447. The current monitor 2447 is coupled to the primary processor 2406. The current monitor 2447 provides a signal indicative of the current draw of the motor 2448. The primary processor 2406 may utilize the signal from the motor current 2447 to control operation of the motor, for example, to ensure the current draw of the motor 2448 is within an acceptable range, to compare the current draw of the motor 2448 to one or more other parameters of the circuit 2400 such as, for example, the position encoder 2440, and/or to determine one or more parameters of a treatment site. In some examples, the current monitor 2447 may be coupled to the safety processor 2404.

In some aspects, actuation of one or more handle controls, such as, for example, a firing trigger, causes the primary processor 2406 to decrease power to one or more components while the handle control is actuated. For example, in one example, a firing trigger controls a firing stroke of a cutting member. The cutting member is driven by the motor 2448. Actuation of the firing trigger results in forward operation of the motor 2448 and advancement of the cutting member. During firing, the primary processor 2406 closes the FET switch 2451 to remove power from the position encoder 2440. The deactivation of one or more circuit components allows higher power to be delivered to the motor 2448. When the firing trigger is released, full power is restored to the deactivated components, for example, by closing the FET switch 2451 and reactivating the position encoder 2440.

In some aspects, the safety processor 2404 controls operation of the segmented circuit 2400. For example, the safety processor 2404 may initiate a sequential power-up of the segmented circuit 2400, transition of the segmented circuit 2400 to and from sleep mode, and/or may override one or more control signals from the primary processor 2406. For example, in the illustrated example, the safety processor 2404 is coupled to the step-down converter 2416. The safety processor 2404 controls operation of the segmented circuit 2400 by activating or deactivating the step-down converter 2416 to provide power to the remainder of the segmented circuit 2400.

Figure 26:
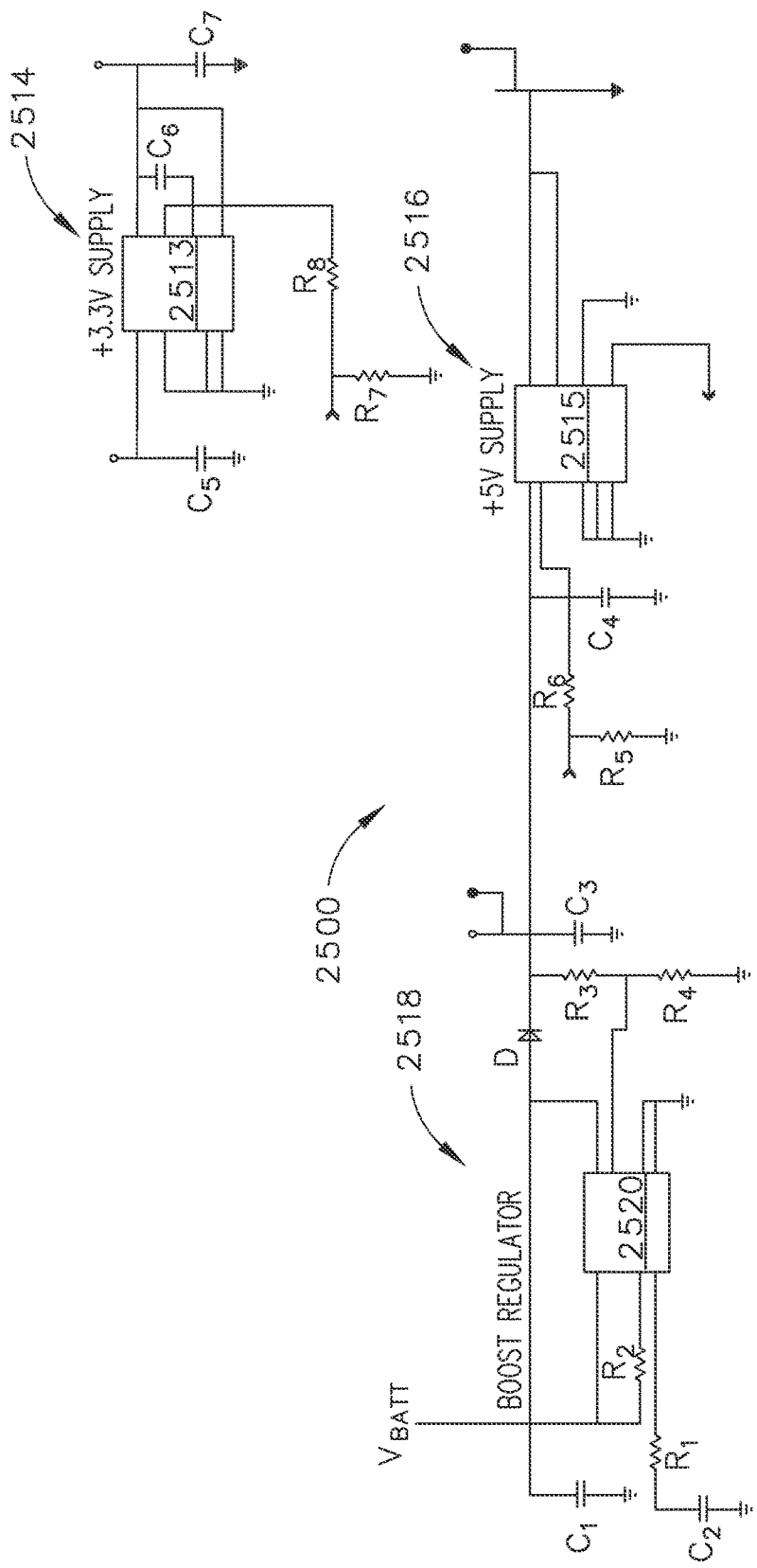
FIG. 26 illustrates one aspect of a power system comprising a plurality of daisy chained power converters configured to be sequentially energized.

FIG. 26 illustrates one aspect of a power system 2500 comprising a plurality of daisy chained power converters 2514, 2516, 2518 configured to be sequentially energized. The plurality of daisy chained power converters 2514, 2516, 2518 may be sequentially activated by, for example, a safety processor during initial power-up and/or transition from sleep mode. The safety processor may be powered by an independent power converter (not shown). For example, in one example, when a battery voltage $V_{BATT}$ is coupled to the power system 2500 and/or an accelerometer detects movement in sleep mode, the safety processor initiates a sequential start-up of the daisy chained power converters 2514, 2516, 2518. The safety processor activates the 13V boost section 2518. The boost section 2518 is energized and performs a self-check. In some examples, the boost section 2518 comprises an integrated circuit 2520 configured to boost the source voltage and to perform a self check. A diode D prevents power-up of a 5V supply section 2516 until the boost section 2518 has completed a self-check and provided a signal to the diode D indicating that the boost section 2518 did not identify any errors. In some examples, this signal is provided by the safety processor. The examples, however, are not limited to the particular voltage range(s) described in the context of this specification.

The 5V supply section 2516 is sequentially powered-up after the boost section 2518. The 5V supply section 2516 performs a self-check during power-up to identify any errors in the 5V supply section 2516. The 5V supply section 2516 comprises an integrated circuit 2515 configured to provide a step-down voltage from the boost voltage and to perform an error check. When no errors are detected, the 5V supply section 2516 completes sequential power-up and provides an activation signal to the 3.3V supply section 2514. In some examples, the safety processor provides an activation signal to the 3.3V supply section 2514. The 3.3V supply section comprises an integrated circuit 2513 configured to provide a step-down voltage from the 5V supply section 2516 and perform a self-error check during power-up. When no errors are detected during the self-check, the 3.3V supply section 2514 provides power to the primary processor. The primary processor is configured to sequentially energize each of the remaining circuit segments. By sequentially energizing the power system 2500 and/or the remainder of a segmented circuit, the power system 2500 reduces error risks, allows for stabilization of voltage levels before loads are applied, and prevents large current draws from all hardware being turned on simultaneously in an uncontrolled manner. The examples, however, are not limited to the particular voltage range(s) described in the context of this specification.

In one aspect, the power system 2500 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 27:
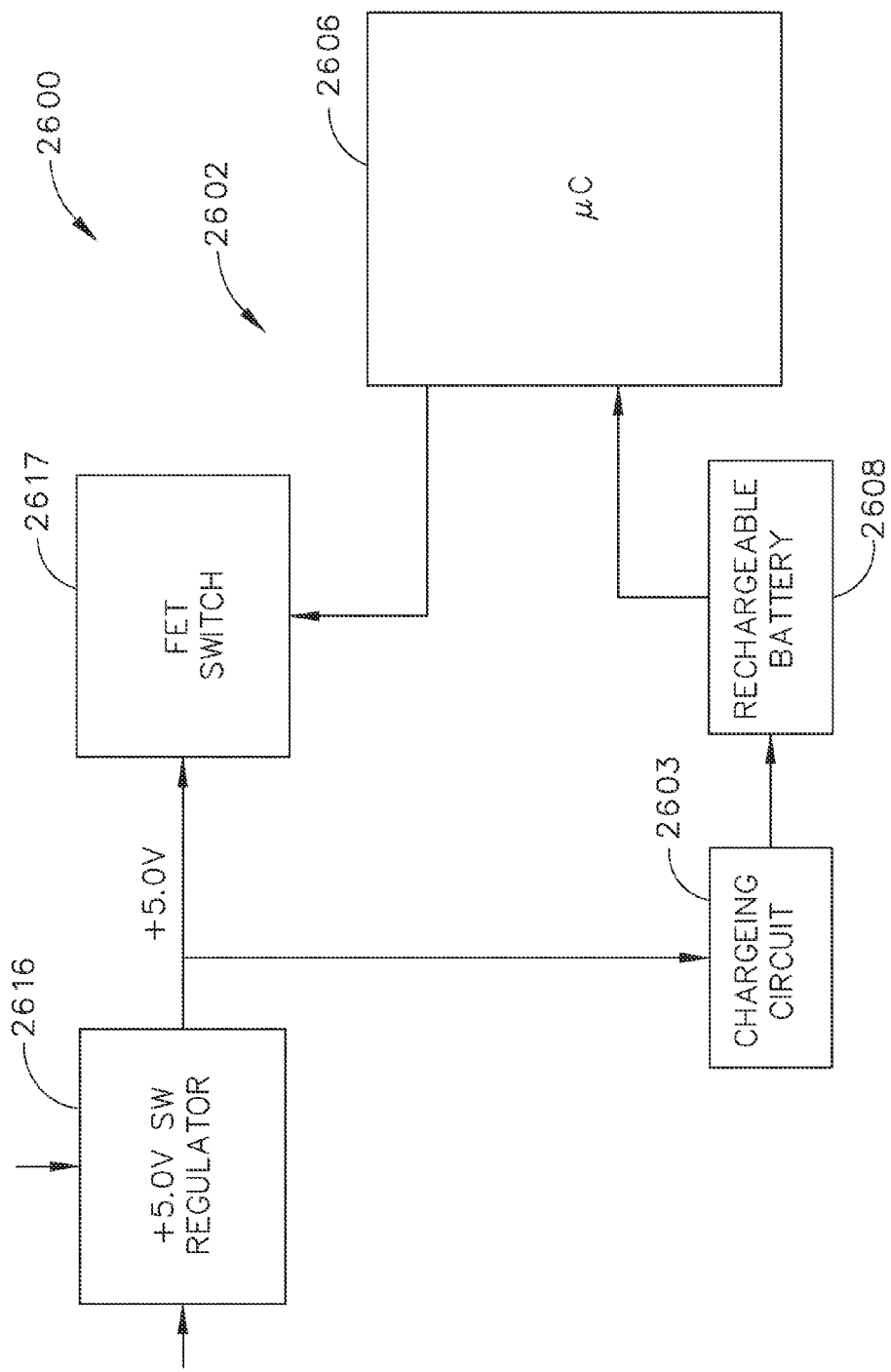
FIG. 27 illustrates one aspect of a segmented circuit comprising an isolated control section.

FIG. 27 illustrates one aspect of a segmented circuit 2600 comprising an isolated control section 2602. The isolated control section 2602 isolates control hardware of the segmented circuit 2600 from a power section (not shown) of the segmented circuit 2600. The control section 2602 comprises, for example, a primary processor 2606, a safety processor (not shown), and/or additional control hardware, for example, a FET Switch 2617. The power section comprises, for example, a motor, a motor driver, and/or a plurality of motor MOSFETS. The isolated control section 2602 comprises a charging circuit 2603 and a rechargeable battery 2608 coupled to a 5V power converter 2616. The charging circuit 2603 and the rechargeable battery 2608 isolate the primary processor 2606 from the power section. In some examples, the rechargeable battery 2608 is coupled to a safety processor and any additional support hardware. Isolating the control section 2602 from the power section allows the control section 2602, for example, the primary processor 2606, to remain active even when main power is removed, provides a filter, through the rechargeable battery 2608, to keep noise out of the control section 2602, isolates the control section 2602 from heavy swings in the battery voltage to ensure proper operation even during heavy motor loads, and/or allows for real-time operating system (RTOS) to be used by the segmented circuit 2600. In some examples, the rechargeable battery 2608 provides a stepped-down voltage to the primary processor, such as, for example, 3.3V. The examples, however, are not limited to the particular voltage range(s) described in the context of this specification.

Figure 28A:
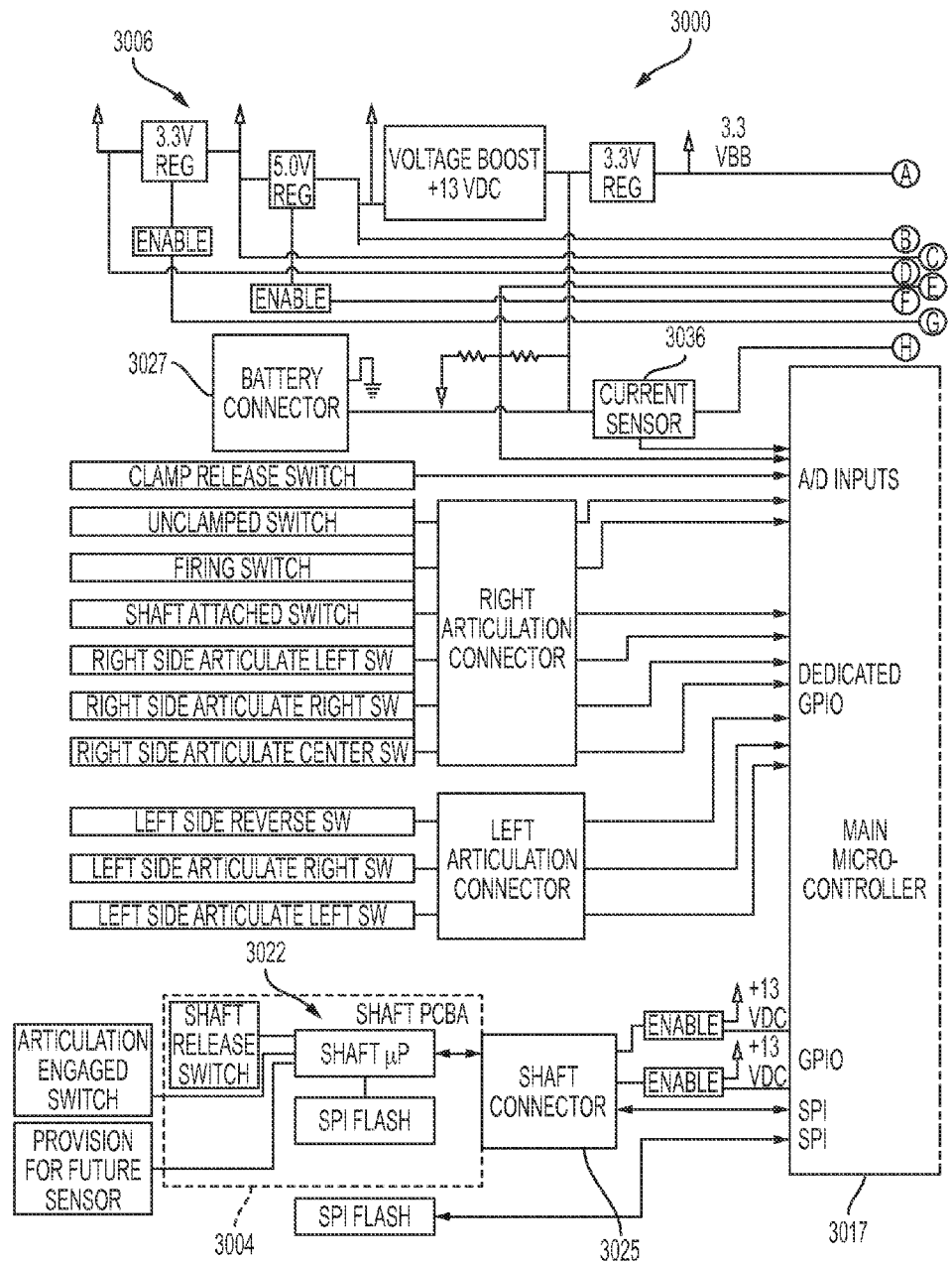
FIGS. 28A and 28B, is a circuit diagram of the surgical instrument of FIG. 1.
Figure 28B:
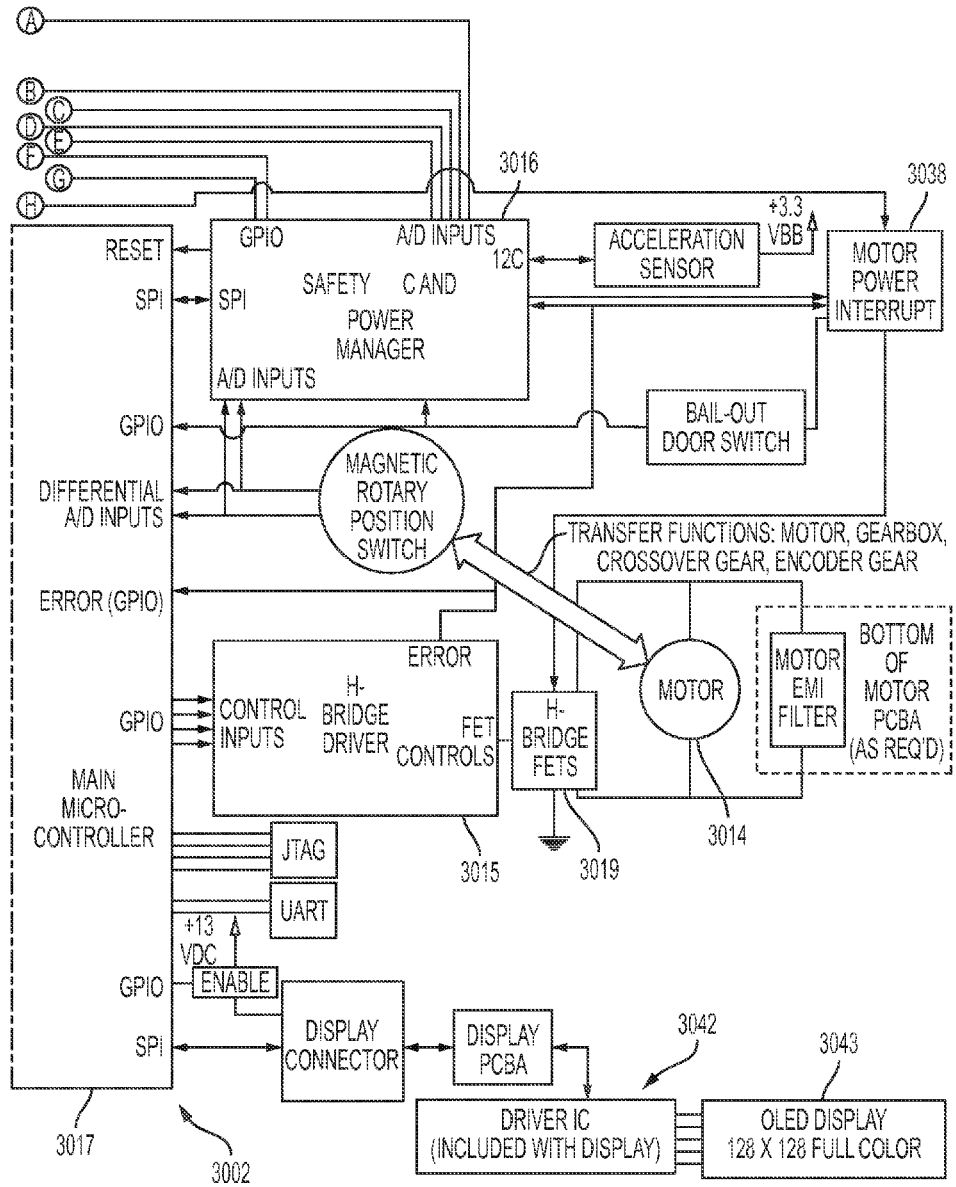

FIGS. 28A and 28B illustrate another aspect of a control circuit 3000 configured to control the powered surgical instrument 10, illustrated in FIGS. 1-18A. As shown in FIGS. 18A, 28B, the handle assembly 14 may include a motor 3014 which can be controlled by a motor driver 3015 and can be employed by the firing system of the surgical instrument 10. In various forms, the motor 3014 may be a DC brushed driving motor having a maximum rotation of, approximately, 25,000 RPM, for example. In other arrangements, the motor 3014 may include a brushless motor, a cordless motor, a synchronous motor, a stepper motor, or any other suitable electric motor. In certain circumstances, the motor driver 3015 may comprise an H-Bridge FETs 3019, as illustrated in FIGS. 28A and 28B, for example. The motor 3014 can be powered by a power assembly 3006, which can be releasably mounted to the handle assembly 14. The power assembly 3006 is configured to supply control power to the surgical instrument 10. The power assembly 3006 may comprise a battery which may include a number of battery cells connected in series that can be used as the power source to power the surgical instrument 10. In such configuration, the power assembly 3006 may be referred to as a battery pack. In certain circumstances, the battery cells of the power assembly 3006 may be replaceable and/or rechargeable. In at least one example, the battery cells can be Lithium-Ion batteries which can be separably couplable to the power assembly 3006.

Examples of drive systems and closure systems that are suitable for use with the surgical instrument 10 are disclosed in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety. For example, the electric motor 3014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery can operate the electric motor 3014 to drive the longitudinally-movable drive member to effectuate the end effector 300. For example, the motor 3014 can be configured to drive the longitudinally-movable drive member to advance a firing mechanism to fire staples into tissue captured by the end effector 300 from a staple cartridge assembled with the end effector 300 and/or advance a cutting member to cut tissue captured by the end effector 300, for example.

As illustrated in FIGS. 28A and 28B and as described below in greater detail, the power assembly 3006 may include a power management controller which can be configured to modulate the power output of the power assembly 3006 to deliver a first power output to power the motor 3014 to advance the cutting member while the interchangeable shaft 200 is coupled to the handle assembly 14 (FIG. 1) and to deliver a second power output to power the motor 3014 to advance the cutting member while the interchangeable shaft assembly 200 is coupled to the handle assembly 14, for example. Such modulation can be beneficial in avoiding transmission of excessive power to the motor 3014 beyond the requirements of an interchangeable shaft assembly that is coupled to the handle assembly 14.

In certain circumstances, the interface 3024 can facilitate transmission of the one or more communication signals between the power management controller 3016 and the shaft assembly controller 3022 by routing such communication signals through a main controller 3017 residing in the handle assembly 14 (FIG. 1), for example. In other circumstances, the interface 3024 can facilitate a direct line of communication between the power management controller 3016 and the shaft assembly controller 3022 through the handle assembly 14 while the shaft assembly 200 (FIG. 1) and the power assembly 3006 are coupled to the handle assembly 14.

In one instance, the main microcontroller 3017 may be any single core or multicore processor such as those known under the trade name ARM Cortex by Texas Instruments. In one instance, the surgical instrument 10 (FIGS. 1-4) may comprise a power management controller 3016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 2004 (FIG. 21A) may be configured specifically for IEC 61508 and ISO 26262 safety critical applications, among others, to provide advanced integrated safety features while delivering scalable performance, connectivity, and memory options.

In certain instances, the microcontroller 3017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Figure 29:
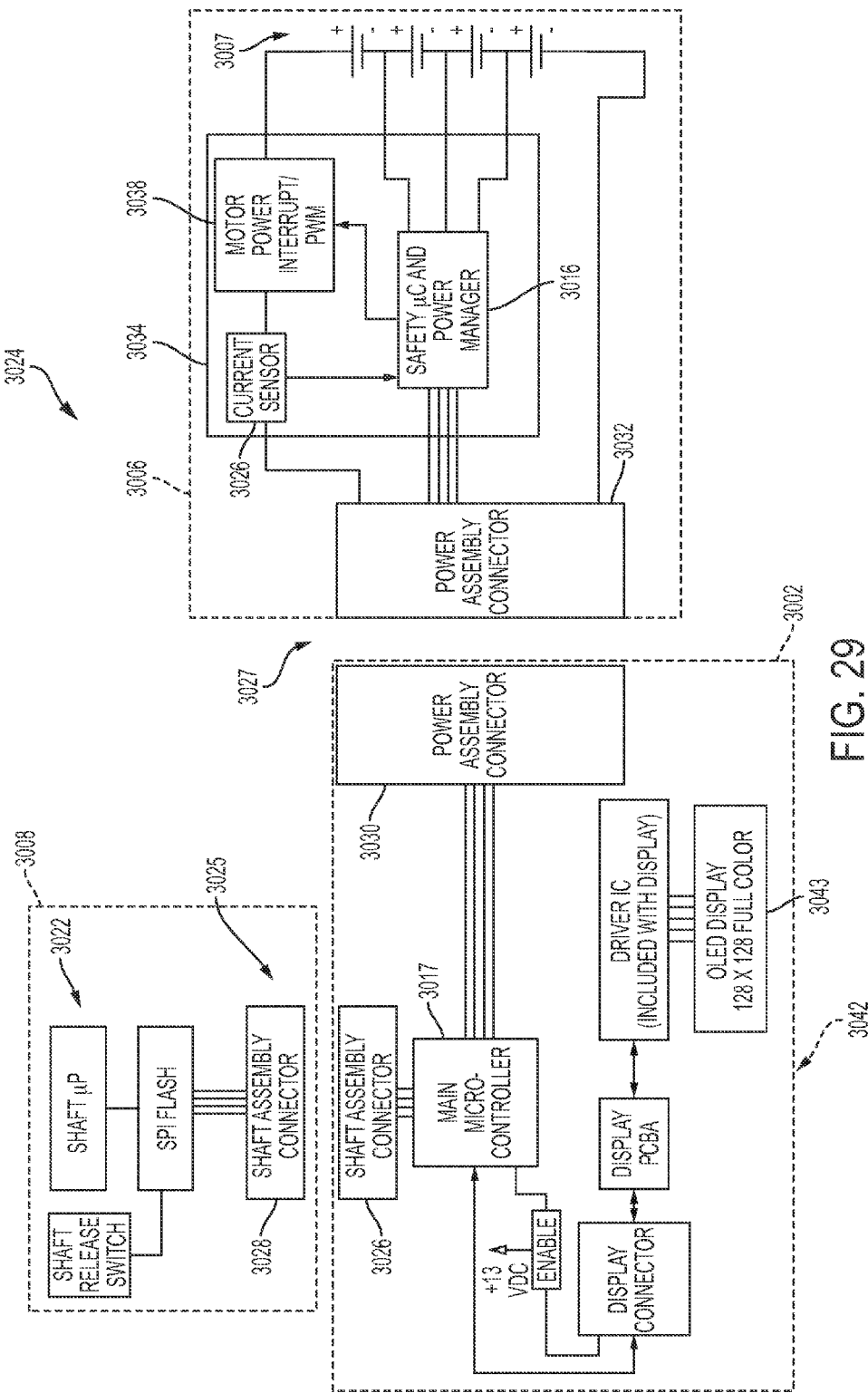
FIG. 29 is a block diagram the surgical instrument of FIG. 1 illustrating interfaces between the handle assembly 14 and the power assembly and between the handle assembly 14 and the interchangeable shaft assembly.

FIG. 29 is a block diagram the surgical instrument of FIG. 1 illustrating interfaces between the handle assembly 14 (FIG. 1) and the power assembly and between the handle assembly 14 and the interchangeable shaft assembly. As shown in FIG. 29, the power assembly 3006 may include a power management circuit 3034 which may comprise the power management controller 3016, a power modulator 3038, and a current sense circuit 3036. The power management circuit 3034 can be configured to modulate power output of the battery 3007 based on the power requirements of the shaft assembly 200 (FIG. 1) while the shaft assembly 200 and the power assembly 3006 are coupled to the handle assembly 14. For example, the power management controller 3016 can be programmed to control the power modulator 3038 of the power output of the power assembly 3006 and the current sense circuit 3036 can be employed to monitor power output of the power assembly 3006 to provide feedback to the power management controller 3016 about the power output of the battery 3007 so that the power management controller 3016 may adjust the power output of the power assembly 3006 to maintain a desired output.

It is noteworthy that the power management controller 3016 and/or the shaft assembly controller 3022 each may comprise one or more processors and/or memory units which may store a number of software modules. Although certain modules and/or blocks of the surgical instrument 14 (FIG. 1) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 10 (FIGS. 1-4) may comprise an output device 3042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 3042 may comprise a display 3043 which may be included in the handle assembly 14 (FIG. 1). The shaft assembly controller 3022 and/or the power management controller 3016 can provide feedback to a user of the surgical instrument 10 through the output device 3042. The interface 3024 can be configured to connect the shaft assembly controller 3022 and/or the power management controller 3016 to the output device 3042. The reader will appreciate that the output device 3042 can instead be integrated with the power assembly 3006. In such circumstances, communication between the output device 3042 and the shaft assembly controller 3022 may be accomplished through the interface 3024 while the shaft assembly 200 is coupled to the handle assembly 14.

Having described a surgical instrument 10 (FIGS. 1-4) and various control circuits 2000, 3000 for controlling the operation thereof, the disclosure now turns to various specific configurations of the surgical instrument 10 and control circuits 2000 (or 3000).

In various aspects the present disclosure provides techniques for data storage and usage. In one aspect, data storage and usage is based on multiple levels of action thresholds. Such thresholds include upper and lower ultimate threshold limits, ultimate threshold that shuts down motor or activates return is current, pressure, firing load, torque is exceeded, and alternatively, while running within the limits the device automatically compensates for loading of the motor.

In one aspect, the instrument 10 (described in connection with FIGS. 1-29) can be configured to monitor upper and lower ultimate threshold limits to maintain minimum and maximum closure clamp loads within acceptable limits. If a minimum is not achieved the instrument 10 cannot start or if it drops below minimum a user action is required. If the clamp load is at a suitable level but drops under minimum during firing, the instrument 10 can adjust the speed of the motor or warn the user. If the minimum limit is breached during operation the unit could give a warning that the firing may not be completely as anticipated. The instrument 10 also can be configured to monitor when the battery voltage drops below the lower ultimate limit the remaining battery power is only direct able towards returning the device to the I-beam parked state. The opening force on the anvil can be employed to sense jams in the end effector. Alternatively, the instrument 10 can be configured to monitor when the motor current goes up or the related speed goes down, then the motor control increases pulse width or frequency modulation to keep speed constant.

In another aspect, the instrument 10 can (FIG. 1) be configured to detect an ultimate threshold of current draw, pressure, firing load, torque such that when any of these thresholds are exceeded, the instrument 10 shuts down the motor or causes the motor to return the knife to a pre-fired position. A secondary threshold, which is less than the ultimate threshold, may be employed to alter the motor control program to accommodate changes in conditions by changing the motor control parameters. A marginal threshold can be configured as a step function or a ramp function based on a proportionate response to another counter or input. For example, in the case of sterilization, no changes between 0-200 sterilization cycles, slow motor 1% per use from 201-400 sterilization cycles, and prevent use over 400 sterilization cycles. The speed of the motor also can be varied based on tissue gap and current draw.

There are many parameters that could influence the ideal function of a powered reusable stapler device. Most of these parameters have an ultimate maximum and/or minimum threshold beyond which the device should not be operated. Nevertheless, there are also marginal limits that may influence the functional operation of the device. These multiple limits, from multiple parameters may provide an overlying and cumulative effect on the operations program of the device.

Accordingly, the present disclosure relates to surgical instruments and, in various circumstances, to surgical stapling and cutting instruments and staple cartridges therefor that are designed to staple and cut tissue.

Efficient performance of an electromechanical device depends on various factors. One is the operational envelope, i.e., range of parameters, conditions and events in which the device carries out its intended functions. For example, for a device powered by a motor driven by electrical current, there may be an operational region above a certain electrical current threshold where the device runs more inefficiently than desired. Put another way, there may be an upper "speed limit" above which there is decreasing efficiency. Such an upper threshold may have value in preventing substantial inefficiencies or even device degradation.

There may be thresholds within an operational envelope, however, that may form regions exploitable to enhance efficiency within operational states. In other words, there may be regions where the device can adjust and perform better within a defined operational envelope (or sub-envelope). Such a region can be one between a marginal threshold and an ultimate threshold. In addition, these regions may comprise "sweet spots" or a predetermined optional range or point. These regions also may comprise a large range within which performance is judged to be adequate.

An ultimate threshold can be defined, above which or below which an action or actions could be taken (or refrained from being taken) such as stopping the device. In addition, a marginal threshold or thresholds can be defined, above which or below which an action or actions could be taken (or refrained from being taken). By way of non-limiting example, a marginal threshold can be set to define where the current draw of the motor exceeds 75% of an ultimate threshold. Exceeding the marginal threshold can result, for example, in the device's beginning to slow motor speed at an increasing rate as it continues to climb toward the ultimate threshold.

Various mechanisms can be employed to carry out the adjustment(s) taken as a result of exceeding a threshold. For example, the adjustment can reflect a step function. It can also reflect a ramped function. Other functions can be utilized.

In various aspects, to enhance performance by additional mechanisms, an overlaying threshold can be defined. An overlaying threshold can comprise one or more thresholds defined by multiple parameters. An overlaying threshold can result in one or more thresholds being an input into the generation of another threshold or thresholds. An overlaying threshold can be predetermined or dynamically generated such as at runtime. The overlaying threshold may come into effect when you the threshold is defined by multiple inputs. For example, as the number of sterilization cycles exceeds 300 (the marginal threshold) but not 500 (the ultimate threshold) the device runs the motor slower. Then as the current draw exceeds its 75% marginal threshold it multiples the slow down going even slower.

Figure 30:
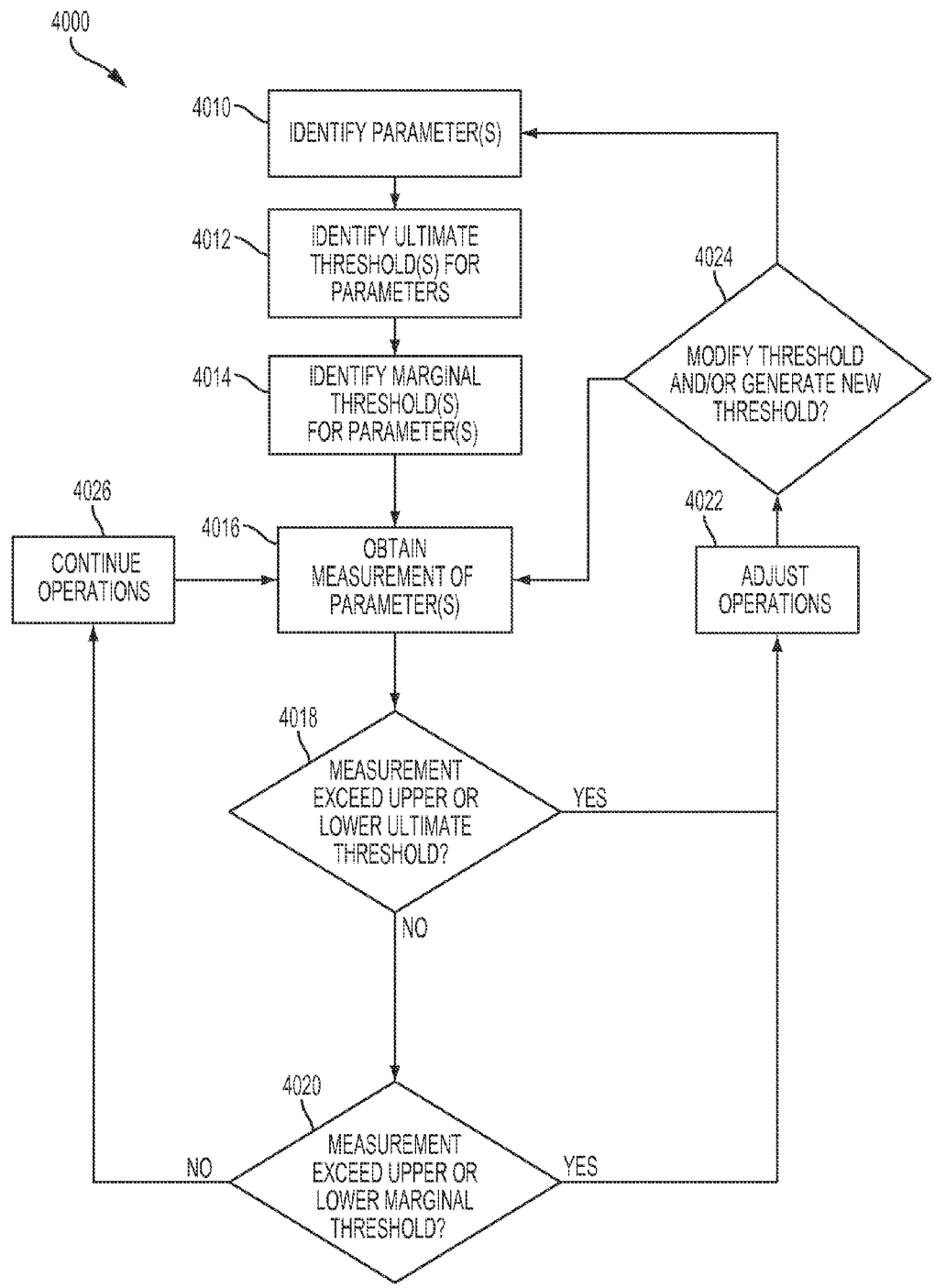
FIG. 30 illustrates one aspect of a process for utilizing thresholds to modify operations of a surgical instrument.

FIG. 30 is a logic diagram disclosing aspects of a multiple-level threshold system wherein a threshold rules framework 4000. Parameters can be identified 4010, such parameters representing quantities, amounts, states, events or more. For example, parameters identified can include one or more of current, voltage, tissue pressure, tissue thickness, jaw closure rate, tissue creep rate, firing load, knife thickness, torque, or battery usage. An ultimate threshold or thresholds for these parameters can be identified 4012. For instance, a predetermined current draw can be identified. As but one example, an ultimate electrical current draw threshold may be defined as 100% of a selected current magnitude. There can be an upper ultimate threshold, a lower ultimate threshold, multiple lower or upper ultimate thresholds depending on the circumstances, or a range defining an ultimate threshold. It will be appreciated that an "ultimate" threshold can be defined and/or calibrated in such a way as to remain essentially a unitary threshold but embody various action triggers. A marginal threshold or thresholds can be identified 4014. If the marginal threshold is exceeded, a motor control program can alter operations to accommodate change.

One or more thresholds can be monitored an acted on during a single surgical procedure, wherein the thresholds are independent of each other with no interaction. In addition, there can be an interactive association between thresholds of two or more parameters. For example, a marginal threshold for a parameter based on current draw can be 75% of the ultimate threshold. In addition, in connection with a parameter based on number of sterilization cycles, a marginal threshold may be set at 200 sterilization cycles, and an ultimate threshold at sterilization 400 cycles. Motor use can proceed normally from 0-199 cycles, and then slow by 1% from 200 cycles to 399. At cycle 400, motor use can be prevented. It will be appreciated, however, that there can be an interactive effect. In other words, because motor speed is reduced by 1% due to exceeding the sterilization cycle threshold, the current draw threshold can be correspondingly adjusted. This interactive effect can result in the motor running more slowly than it would if either input were considered independently.

Thus, the value of one threshold can be an input into the value of another threshold, or one threshold can be completely independent of another threshold. Where two or more thresholds are activated, it can be considered that there can be an overlaying threshold. As a result, multiple thresholds, defining multiple boundaries and limits, can have an overlaying or cumulative effect on operations of instrument 10 (FIGS. 1-4). And, one threshold in a multiple-threshold operation scenario can have a cause-and-effect with another threshold, or there may be no cause-and-effect and the thresholds may exist independent of each other.

In addition, a threshold can be dynamically set and/or reset depending on conditions experienced during surgery or other conditions. In other words, prior to a given surgical procedure, a module or modules can be preprogrammed into instrument 10 (FIGS. 1-4) or uploaded as needed. Also, a threshold can be dynamically determined, or uploaded, during a surgical procedure.

Turning briefly now to FIG. 1, numerous parameters can be assigned thresholds. Thus, in examples thresholds may be assigned based on tissue gap between the anvil 306 and staple cartridge 304, or anvil 306 and second jaw member 302, of an end effector 300, and motor speed varied thereby. In addition, in example thresholds based on current can vary motor speed control. Further, in various examples ultimate, marginal and overlaying thresholds can be established in connection with closure clamp loads in furtherance of an acceptable operating range. Plus, in various examples opening force on an anvil 306 can help to detect a jam. Further, in various examples if a minimum threshold is not achieved, the system may be prevented from starting or if it drops below a minimum then a user action can be required.

Still with reference to FIG. 1, in various aspects, it can be determined whether clamp load is acceptable and when clamp load drops under a minimum threshold during firing the speed of the motor can be adjusted and/or the clinician warned. In various examples, when a minimum threshold is exceeded during operation, instrument 10 can give a warning that the firing may not be completely as anticipated. Moreover, in various examples thresholds can be assigned wherein if battery charge falls below a threshold then remaining battery charge can be used to return the device to a parked state with respect to the I-beam.

However, thresholds can be referenced even during operations that do not exceed a threshold. Thus, for example, instrument 10 can, while running "within limits", compensate for the loading of the motor. For instance, if current goes up or related speed goes down, then motor control can increase pulse width or frequency modulation to help to maintain a constant speed. In other words, measures can be taken to improve and/or optimize operations of instrument 10 even while running "within limits."

In addition, dynamically during a surgical procedure, a threshold can be modified, or a new threshold generated. This can occur after several events including adjusting operations of the instrument 10.

Turning now back to FIG. 30, in various aspects a parameter or parameters are identified 4010. Further, an ultimate threshold or thresholds for a given parameter(s) are identified 4012. In addition, a marginal threshold or thresholds for a given parameter(s) are identified 4014. Measures 4010, 4012, and 4014 can be accomplished prior to the procedure, during the procedure, or both.

Measurements of a parameter(s) are obtained 4016. It can be determined whether the measurement of a given parameter exceeds an upper or lower ultimate threshold for the parameter 4018. When the answer is no, it can be determined whether the measurement of a given parameter exceeds an upper or lower marginal threshold for the parameter 4020. When the answer is no, operations can be continued 4026. And, measurements of a given parameter(s) can be again obtained.

When, however, the answer is yes to whether the measurement of a given parameter exceeds an upper or lower ultimate threshold for the parameter 4018, control can pass to where operations can be adjusted 4022. Many types of adjustments can be made. One example is to vary motor speed. It can be determined whether to modify a given threshold and/or generate a new threshold 4024. This can occur after operations have been adjusted 4022.

After operations are adjusted, it can be determined whether to modify a threshold or generate a new threshold. For example, a marginal threshold initially set at 75% can be set to a different value. In addition, a new threshold on the same parameter, or a new threshold on a new parameter, can be generated if desired.

Upon determining whether to modify a threshold or generate a new one, control can pass back to step 4016 where measurement of a parameter(s) is obtained. In addition, control can proceed to identify 4010 parameters.

When the answer to whether the measurement exceeds an upper or lower ultimate threshold is no, however, then it can be determined when the measurement exceeds an upper or lower marginal threshold. When the answer is yes, then operations can be adjusted 4022 and control proceed as above. When the answer is no, operations can be continued 4026 and control proceed to measuring a parameter(s).

It will be appreciated that the sequence of steps can be varied and is not limited to that specifically disclosed in FIG. 30. As just one example, after obtaining measurement of a parameter(s) 4016, it can then be determined whether a marginal threshold is exceeded 4020. In addition, an overlaying threshold can expressly be identified and considered in the course of the flow.

Figure 31:
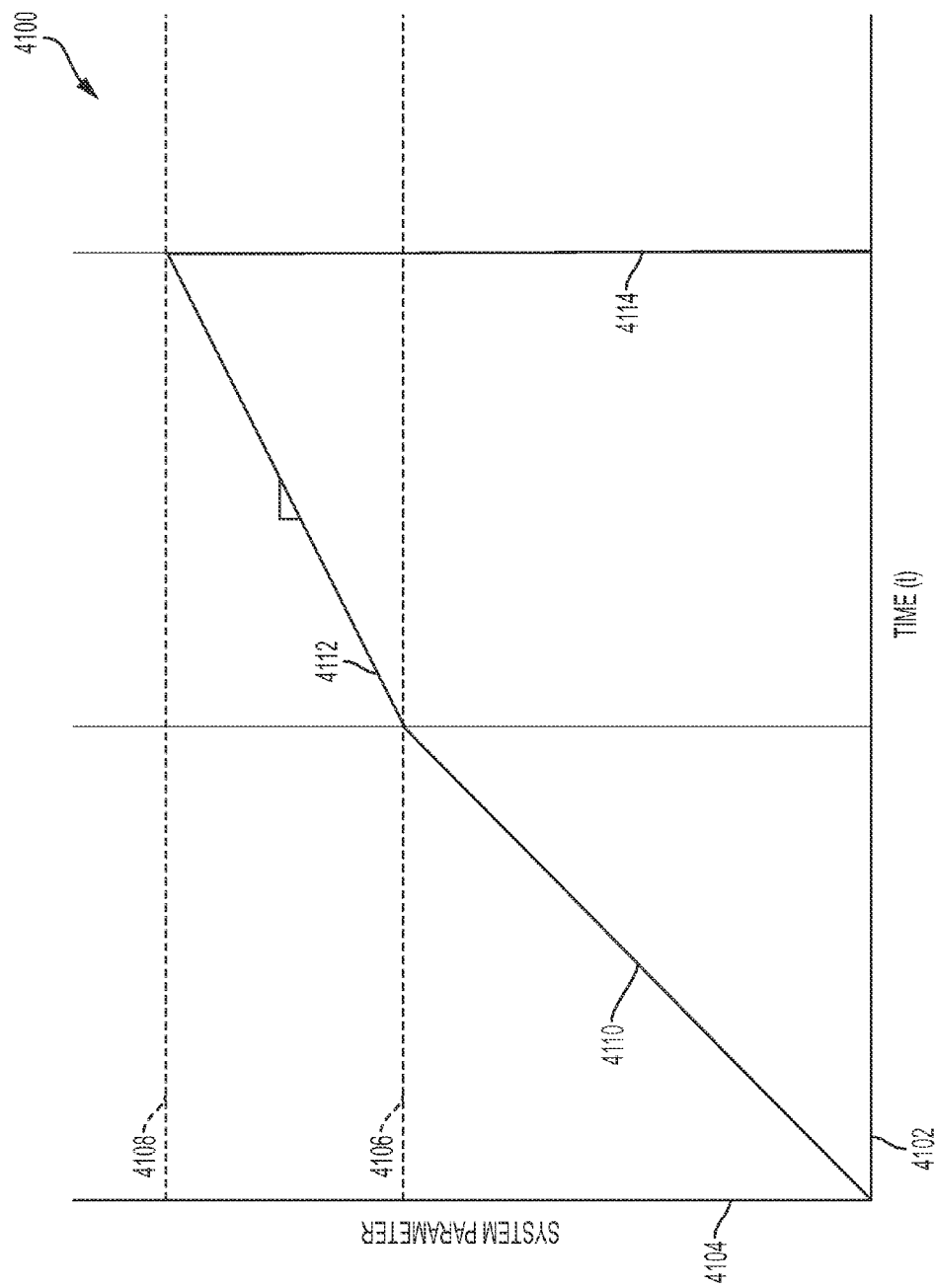
FIG. 31 illustrates an example graph showing modification of operations of a surgical instrument describing a linear function.

FIG. 31 is a graphical representation 4100 of instrument system parameters versus time depicting how, in one aspect, instrument system parameters can be adjusted in the event that a threshold is reached. Time (t) is shown along a horizontal (x) axis 4102 and the instrument System Parameter is shown along a vertical (y) axis 4104, marginal threshold 4104 and ultimate threshold 4106. In the graphical representation 4100 depicted in FIG. 34, the y-axis parameter 4102 is the one to which a threshold of instrument system parameter is assigned and the x-axis 4102 represents time. At a certain time during operation of instrument 10 (FIGS. 1-4), as evidenced by function 4110, a measurement can indicate that marginal threshold 4106 is reached. At this point, operations of the instrument 10 (FIGS. 1-4) can be adjusted. For example, when the y-axis 4104 parameter is electrical current draw by a motor, a function can be imposed on the subsequent electrical current draw and limit current in some fashion. In one example, the function can represent a linear progression 4112. At a certain time in the course of operation, an ultimate threshold 4108 can be reached. At this point, electrical current can be discontinued 4114. Accordingly, an adjustment mechanism can be accomplished via a linear function. An additional perspective with which to view the operational adjustment is that there can be a square-wave multiplier change.

Figure 32:
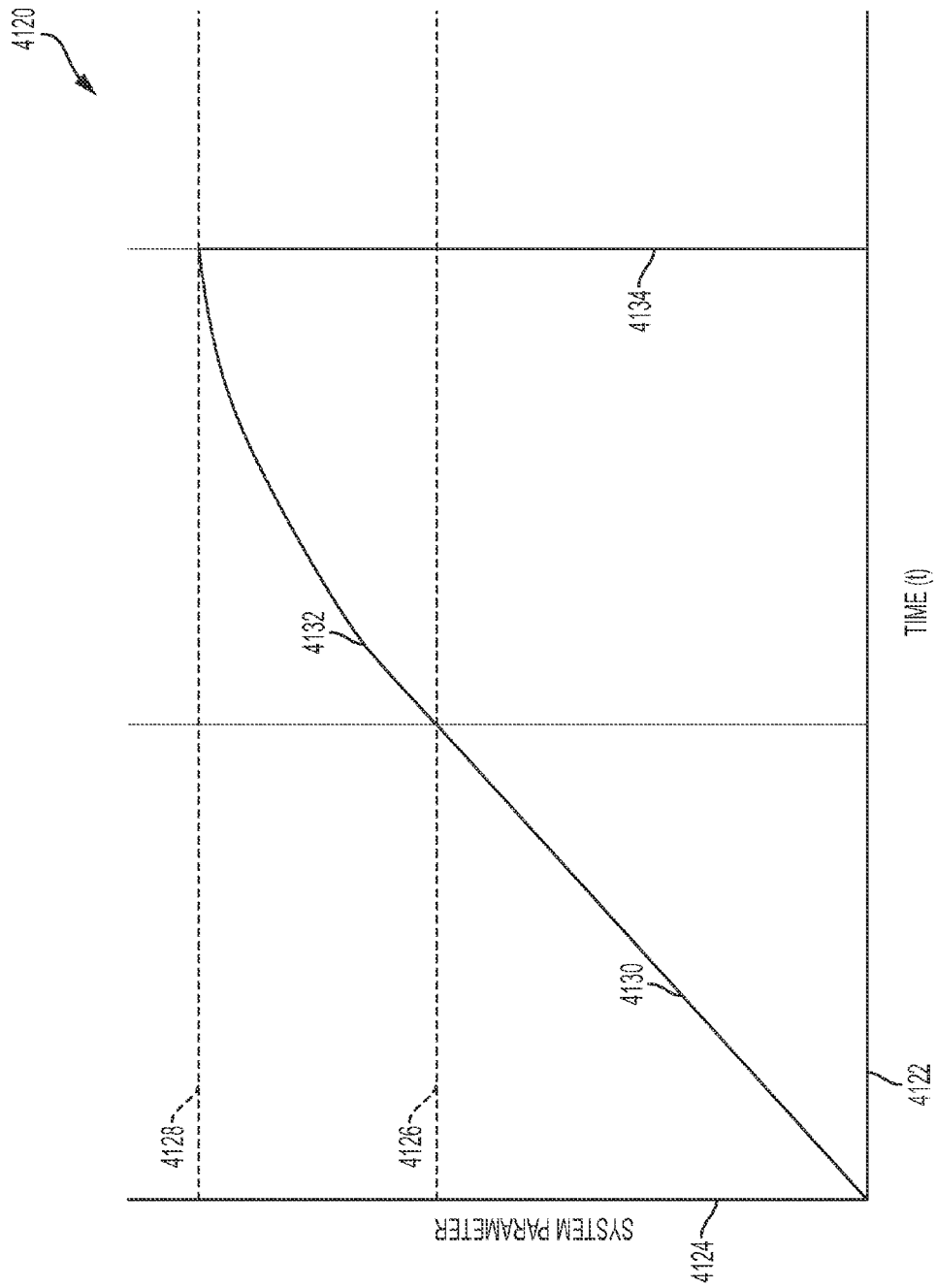
FIG. 32 illustrates an example graph showing modification of operations of a surgical instrument describing a non-linear function.

FIG. 32 is a graphical representation 4120 of instrument system parameter depicting how, in another aspect, a system parameter can be adjusted in the event that a threshold is reached. Time (t) is shown along a horizontal (x) axis 4122 and the number of Instrument Operations is shown along a vertical (y) axis 4124, marginal threshold 4126 and ultimate threshold 4128. Here the y-axis 4124 parameter is the one to which a threshold is assigned. At a certain time during operation of instrument 10 (FIGS. 1-4), a measurement can indicate that the marginal threshold 4126 is reached during the course of operation 4130. At this point, operations of the instrument 10 can be adjusted. For example, when the y-axis 4124 parameter is electrical current draw by a motor, a limit can be placed on the subsequent current draw representing a non-linear progression 4132. At a certain time after this, an ultimate threshold 4128 can be reached. At this point, current can be discontinued 4134. Accordingly, an adjustment mechanism can be accomplished via a non-linear function 4132, with a variable slope. An additional perspective with which to view the operational adjustment is that there is an exponential multiplier change; here, the closer the y-axis 4124 parameter comes to the ultimate threshold 4128, the rate at which current increases diminishes.

Figure 33:
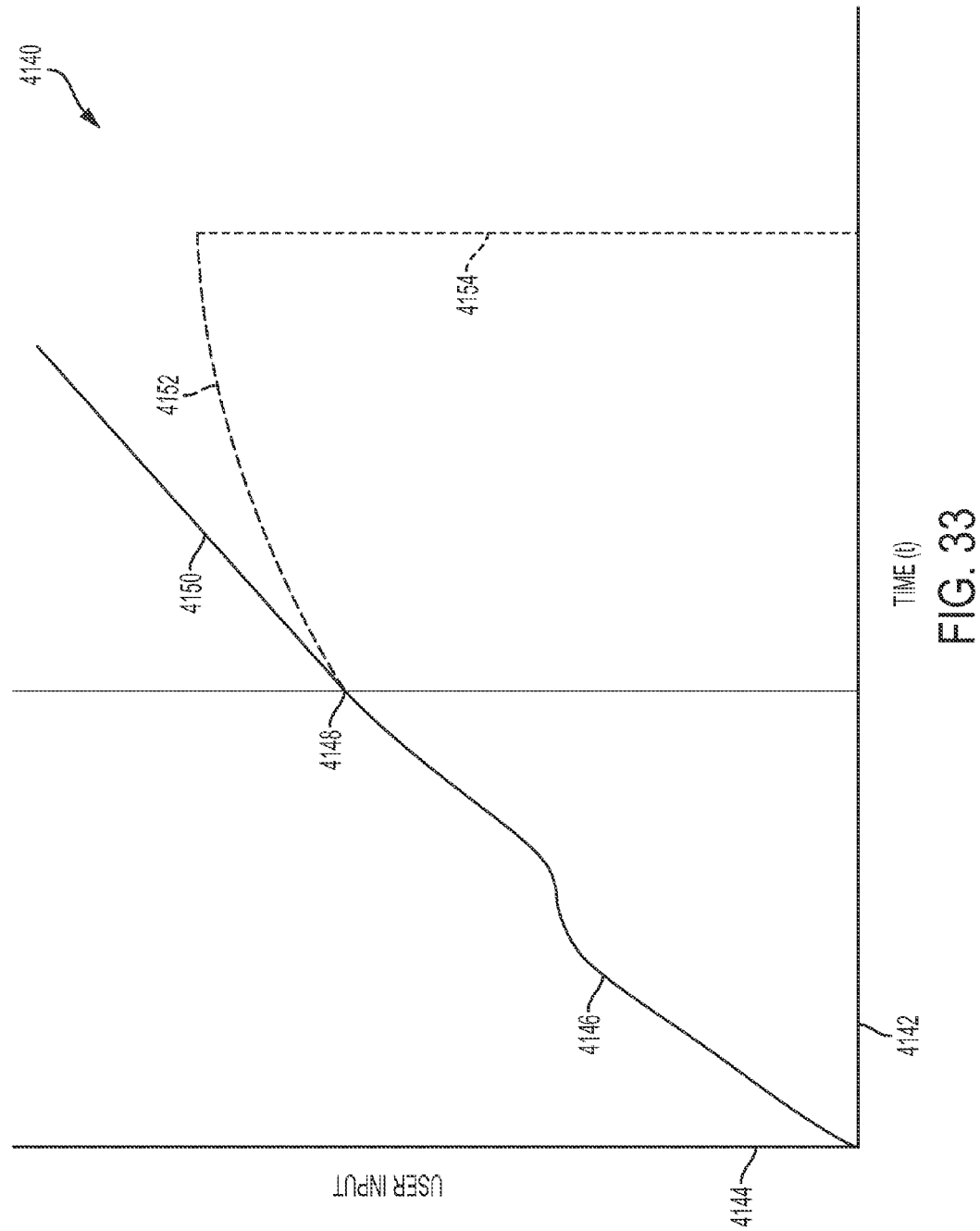
FIG. 33 illustrates an example graph showing modification of operations of a surgical instrument based on an expected user input parameter.

FIG. 33 is a graphical representation 4140 that represents one aspect wherein a response by instrument 10 (FIGS. 1-4) to clinician input (User Input) is detected and then a modification is made. Time (t) is shown along a horizontal (x) axis 4142 and User Input is represented along a vertical (y) axis 4144. In other words, a clinician, in performing a procedure, can actuate a response by instrument 10 such as depressing closure trigger 32 (FIG. 1) which may for example cause motor operation 4146. As motor speed increases there may or not be a threshold reached. At a certain point, however, here represented by the divergence point 4148 of curves 4150 and 4152, it can be determined that motor speed has reached an actual level, or a future level be predicted, that is or will be suboptimal or otherwise undesirable. At this point, rather than following the actual or expected speed curve 4150, instrument 10 can employ a control measure such as an algorithm to adapt or otherwise modify the output, thus regulating the motor. At a certain point, motor actuation can be discontinued 4154. In other words, instrument 10 can take an actual or expected y-axis parameter and, determining that such actual or expected measurement is excessive, employ an algorithm to modify such parameter. Put another way, measured clinician behavior can comprise a value for a threshold or thresholds.

Figure 34:
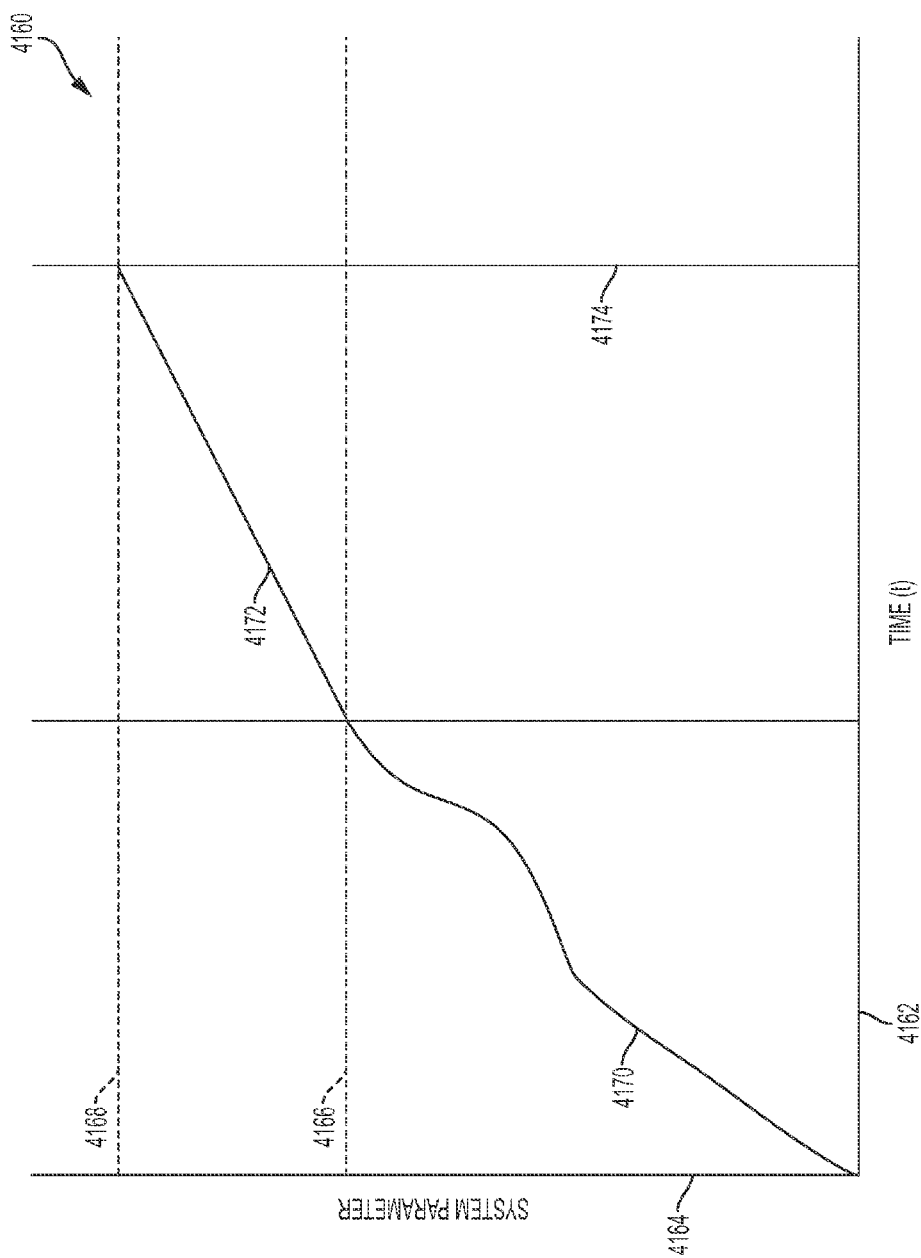
FIG. 34 illustrates an example graph showing modification of velocity of a drive based on detection of a threshold.

FIG. 34 is a graphical representation 4160 of instrument system parameters that represents one aspect wherein instrument 10 (FIGS. 1-4) detects whether a marginal threshold 4166 or ultimate threshold 4168 is reached, and responds accordingly. Time (t) is shown along the horizontal (x) axis 4162 and instrument System Parameters is shown along the vertical (y) axis 4164. For example, here the vertical (y) axis 4154 parameter can be the velocity of a drive, such as a closure drive system 30 (FIG. 1) or firing drive system 80 (FIG. 1). Instrument 10 can check whether during the course of operation 4170 a marginal threshold 4166 velocity is reached. When the marginal threshold 4166 is reached, a control measure such as an algorithm can be used to adapt or otherwise modify the velocity 4172. The modified velocity 4172 can be given by a linear or non-linear function. And, at an ultimate threshold, power to the motor can be discontinued 4174.

It will be appreciated that where FIG. 33 can represent a situation where an actual or predicted value is evaluated, whether or not an express threshold is provided, FIG. 34 is a graphical representation where thresholds are provided. It can be appreciated, however, that a threshold or thresholds can be implicitly given to FIG. 33 with equivalent results, insofar as a predetermined or dynamically determined value can serve as a functional equivalent of a threshold, or trigger actions associated with a threshold or thresholds. There may be two or more ceiling or floor values that can serve as such threshold functional equivalents.

Figure 35:
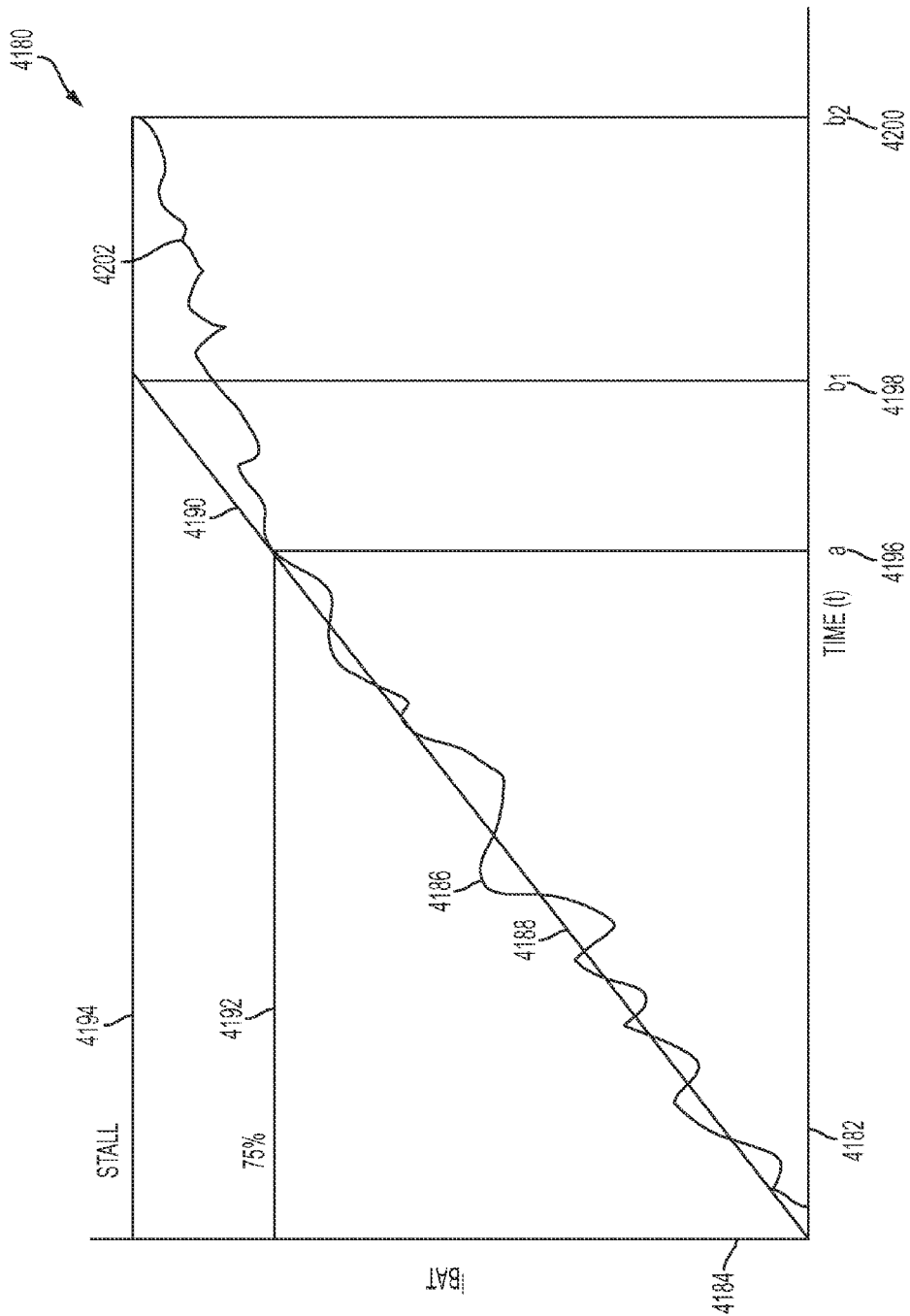
FIG. 35 illustrates an example graph showing modification in connection with operations based on battery current based on detection of a threshold.

Turning to another example using thresholds, FIG. 35 is a graphical representation 4180 of battery current versus time, where Time (t) is shown along the horizontal (x) axis 4182 and battery current $I_{BAT}$ is shown along the vertical (y) axis 4184. In one example battery current $I_{BAT}$ 4184 is monitored under varying operational conditions. As motor speed increases, current drawn 4186 from a battery 90 (FIG. 4) increases. Current drawn can increase in a non-linear manner depending on several factors; however, instrument 10 (FIGS. 1-4) can resolve the current drawn into a linear function 4188. The linear function can be based on (1) averaging overall current, (2) be based on a prediction of future current based on past and/or present current, both (1) and (2), or another function. Linear function 4188 can be extended out theoretically to linear function 4190, which is an extrapolated extension with the same slope as linear function 4188.

Once linear function 4188 reaches a marginal threshold 4192, instrument 10 (FIGS. 1-4) can take action to modify the response. Here the marginal threshold is given as 75% of an ultimate threshold 4194 wherein the ultimate threshold represents a motor stall; however, it will be appreciated that the selection of the marginal threshold or ultimate threshold can be made based on multiple factors. In other words, marginal threshold 4192 can be reached at time "a" 4196. If adjustments are not made, it is expected that motor stall would occur at time "b1" 4198. However, due to adjustments made by instrument 10, the actual motor stall will not occur until time "b2" 4200. It is possible that a stall might not occur at all, because the more graduated rise may help to prevent such an event. Function 4202, which is implemented via a control measure, can be based on slowing the motor, or another adjustment. It can manifest as a stepped, ramped or further function.

Employing the thresholds herein can give the clinician greater time to react and adapt, maintain a desired efficiency of the instrument, and prolong battery life. Thus, utilizing thresholds can provide multiple benefits in connection with ease of clinician use and protection of the instrument itself.

Figure 36:
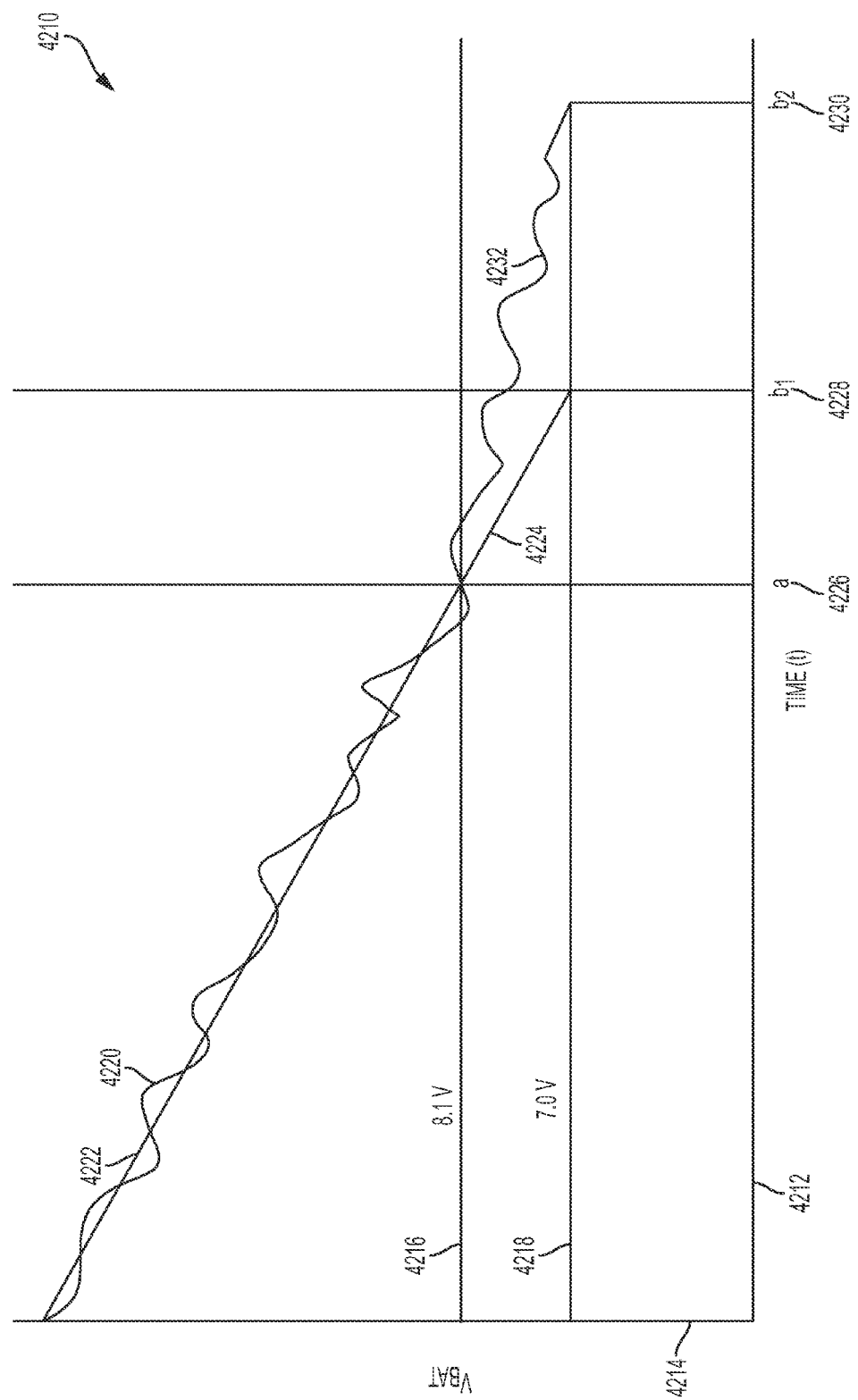
FIG. 36 illustrates an example graph showing modification in connection with operations based on battery voltage based on detection of a threshold.

Turning to another aspect, FIG. 36 is a graphical representation 4210 of battery voltage that shows Time (t) along the horizontal (x) axis 4212 and battery voltage $V_{BAT}$ along the vertical (y) axis 4214. In one example a threshold can be set in connection with battery voltage $V_{BAT}$ 4214. Here a marginal threshold 4216 can be set at 8.1V. Additionally, an ultimate threshold 4218 can be set at 7.0V. During the course of operation of instrument 10 (FIGS. 1-4), voltage can decrease over time. The curve described by measuring the voltage decrease 4220 is not necessarily linear. However, instrument 10 can resolve the voltage decrease into a linear function 4222. The linear function can be based on (1)

averaging overall voltage, (2) be based on a prediction of future voltage based on past and/or present voltage, both (1) and (2), or another function. Linear function 4222 can be extrapolated out theoretically to linear function 4224, which has the same slope as linear function 4222.

Once linear function 4222 reaches a marginal threshold 4216, instrument 10 can take action to modify the response. Marginal threshold 4216 is reached at time "a" 4226. If adjustments are not made, it is expected that a depleted battery condition would occur at time "b1" 4228. However, due to adjustments made by instrument 10 (FIGS. 1-4), the actual depleted battery condition will not occur until time "b2" 4230. Again, it is possible that it may not occur at all. Function 4232, which can be implemented via a control measure, can be based on slowing the motor, or another adjustment. It can manifest as a stepped, ramped or further function.

Figure 37:
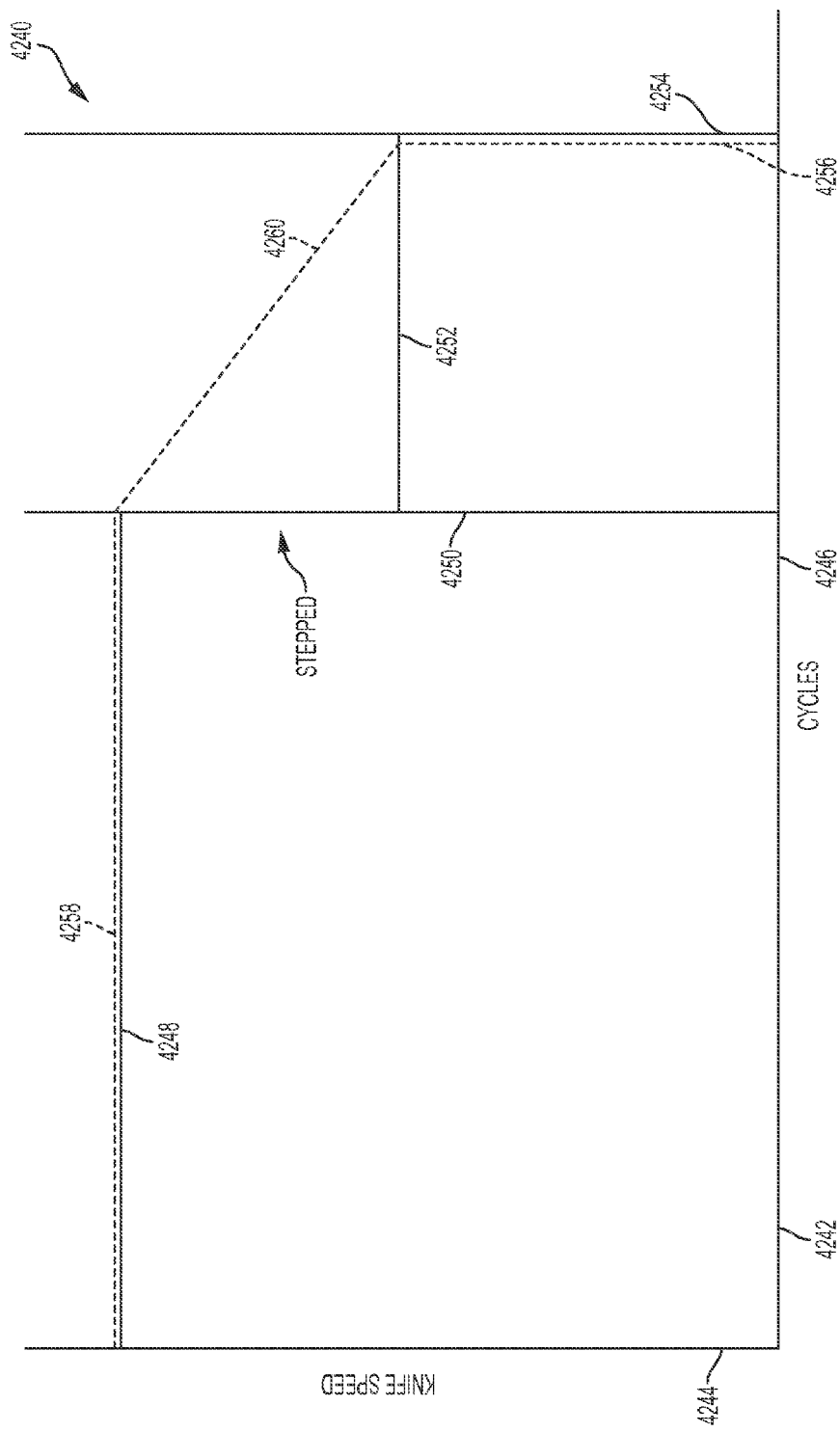
FIG. 37 illustrates an example graph showing modification of knife speed based on detection of a cycle threshold.

FIG. 37 is a graphical representation 4240 of knife speed versus number of cycles where and Cycles is shown along the horizontal (x) axis 4242 and Knife Speed is shown along the vertical (y) axis 4244. As shown in the example illustrated by FIG. 37, thresholds can be employed to adjust speed of a knife 280 (FIG. 8) based on the number of cycles. Relevant cycles can refer to an amount of firings performed by instrument 10 (FIGS. 1-4), sterilization cycles performed by instrument 10, or other measured events. An objective of managing instrument operation by this threshold mechanism is to maximize the likelihood that an incision will be effective, taking into account potential blunting of the knife 280 edge after multiple uses. In this example, firing of the knife can be initialized based on an expected speed. However, once a marginal threshold 4246 is reached based on number of cycles, speed can be reduced from speed 4248 to 4252, such as in a stepped manner 4250. Thus, once marginal threshold 4760 is exceeded, knife 280 will fire at a progressively lower speed. This will occur for a given number of cycles 4246 until ultimate threshold 4254 is reached. At this point, knife speed will be stepped down 4256 even more or of course instrument 10 can alert the clinician that it may be undesirable to incise with the knife, and can lock out firing. It will be understood that function 4248 shows employing a stepped function once a threshold 4246 is reached, and function 4258 shows employing a ramped function 4260 once a threshold 4246 is reached. Additional functions can be employed.

Further, it will be appreciated that the thresholds given in FIG. 37 have been defined on the x-axis 4711, whereas prior figures have shown thresholds on the y-axis 4712. It will also be appreciated that there can be an additional axis or axes taken into account, i.e., a z-axis or further axes, wherein the interrelationship of multiple variables can be considered. Further, thresholds from a first parameter can be considered along with thresholds from a second parameter, and one threshold can comprise an input into another threshold, and vice versa.

When a threshold is exceeded, the clinician can be notified. This can be based on a feedback system. In certain instances, the feedback system may comprise one or more visual feedback systems such as display screens, backlights, and/or LEDs, for example. In certain instances, the feedback system may comprise one or more audio feedback systems such as speakers and/or buzzers, for example. In certain instances, the feedback system may comprise one or more haptic feedback systems, for example. In certain instances, the feedback system may comprise combinations of visual, audio, and/or tactile feedback systems, for example. Such feedback can serve to alert or warn the clinician.

Figure 38:
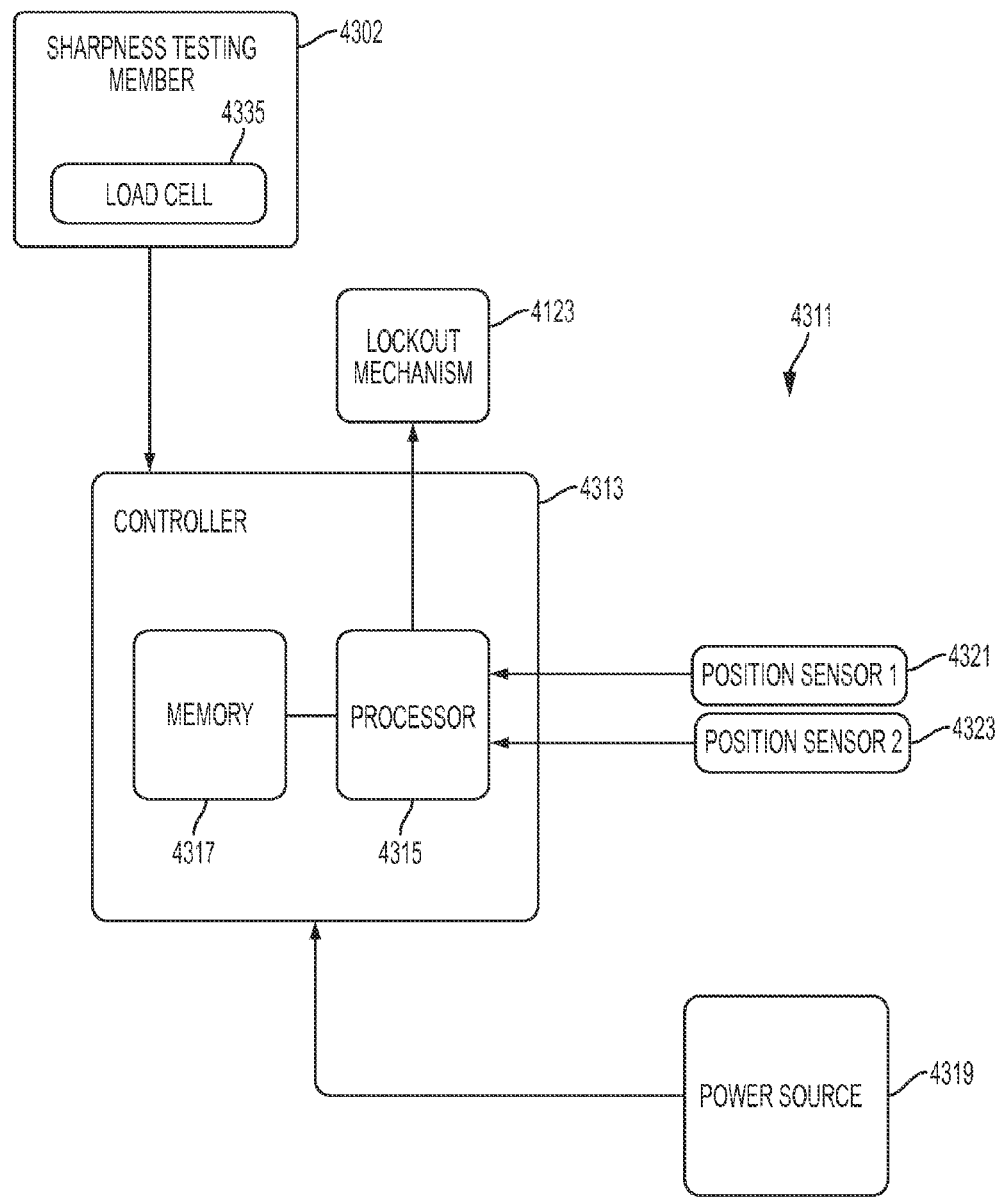
FIG. 38 illustrates a logic diagram of a system for evaluating sharpness of a cutting edge of a surgical instrument according to various aspects.

FIG. 38 illustrates a logic diagram of a system 4311 for evaluating sharpness of a cutting edge 182 (FIG. 20) of a surgical instrument 10 (FIGS. 1-4) according to various examples. FIG. 38 illustrates a sharpness testing system 4311 for evaluating sharpness of a cutting edge of a surgical instrument 10 according to various examples. In certain instances, the system 4311 can evaluate the sharpness of the cutting edge 182 by testing the ability of the cutting edge 182 to be advanced through a sharpness testing member 4302. For example, the system 4311 can be configured to observe the time period the cutting edge 182 takes to fully transect and/or completely pass through at least a predetermined portion of a sharpness testing member 4302. If the observed time period exceeds a predetermined threshold, the module 4310 may conclude that the sharpness of the cutting edge 182 has dropped below an acceptable level, for example.

In one aspect, the sharpness testing member 4302 can be employed to test the sharpness of the cutting edge 182 (FIG. 20). In certain instances, the sharpness testing member 4302 can be attached to and/or integrated with the cartridge body 194 (FIG. 20) of the staple cartridge 304 (FIGS. 1, 2, and 20), for example. In certain instances, the sharpness testing member 4302 can be disposed in the proximal portion of the staple cartridge 304, for example. In certain instances, the sharpness testing member 4302 can be disposed onto a cartridge deck or cartridge body 194 of the staple cartridge 304, for example.

In certain instances, a load cell 4335 can be configured to monitor the force (Fx) applied to the cutting edge 182 (FIG. 20) while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. The load cell 4335 of the sharpness testing member 4302 may be employed to measure the force (Fx) applied to the cutting edge 182 while the cutting edge 182 travels a predefined distance (D) through the sharpness testing member 4302 may be employed to determine the sharpness of the cutting edge 182.

In certain instances, the module 4311 may include a microcontroller 4313 ("controller") which may include a microprocessor 4315 ("processor") and one or more computer readable mediums or memory units 4317 ("memory"). In certain instances, the memory 4317 may store various program instructions, which when executed may cause the processor 4315 to perform a plurality of functions and/or calculations described herein. In certain instances, the memory 4317 may be coupled to the processor 4315, for example. A power source 4319 can be configured to supply power to the controller 4313, for example. In certain instances, the power source 4319 may comprise a battery (or "battery pack" or "power pack"), such as a Li ion battery, for example. In certain instances, the battery pack may be configured to be releasably mounted to the handle 14. A number of battery cells connected in series may be used as the power source 4319. In certain instances, the power source 4319 may be replaceable and/or rechargeable, for example.

In certain instances, the processor 4313 can be operably coupled to the feedback system and/or the lockout mechanism 4123, for example.

The module 4311 may comprise one or more position sensors. Example position sensors and positioning systems suitable for use with the present disclosure are described in U.S. patent application Ser. No. 13/803,210, entitled SENSOR ARRANGEMENTS FOR ABSOLUTE POSITIONING SYSTEM FOR SURGICAL INSTRUMENTS, and filed Mar. 14, 2013, now U.S. Patent Application Publication No. 2014/0263538, the disclosure of which is hereby incorporated by reference herein in its entirety. In certain instances, the module 4311 may include a first position sensor 4321 and a second position sensor 4323. In certain instances, the first position sensor 4321 can be employed to detect a first position of the cutting edge 182 (FIG. 20) at a proximal end of a sharpness testing member 4302, for example; and the second position sensor 4323 can be employed to detect a second position of the cutting edge 182 at a distal end of a sharpness testing member 4302, for example.

In certain instances, the position sensors 4321 and 4323 can be employed to provide first and second position signals, respectively, to the microcontroller 4313. It will be appreciated that the position signals may be analog signals or digital values based on the interface between the microcontroller 4313 and the position sensors 4321 and 4323. In one example, the interface between the microcontroller 4313 and the position sensors 4321 and 4323 can be a standard serial peripheral interface (SPI), and the position signals can be digital values representing the first and second positions of the cutting edge 182, as described above.

Further to the above, the processor 4315 may determine the time period between receiving the first position signal and receiving the second position signal. The determined time period may correspond to the time it takes the cutting edge 182 (FIG. 20) to advance through a sharpness testing member 4302 from the first position at a proximal end of the sharpness testing member 4302, for example, to a second position at a distal end of the sharpness testing member 4302, for example. In at least one example, the controller 4313 may include a time element which can be activated by the processor 4315 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4313 can compare the time period it takes the cutting edge 182 (FIG. 20) to advance from the first position to the second position to a predefined threshold value to assess whether the sharpness of the cutting edge 182 has dropped below an acceptable level, for example. In certain instances, the controller 4313 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 39:
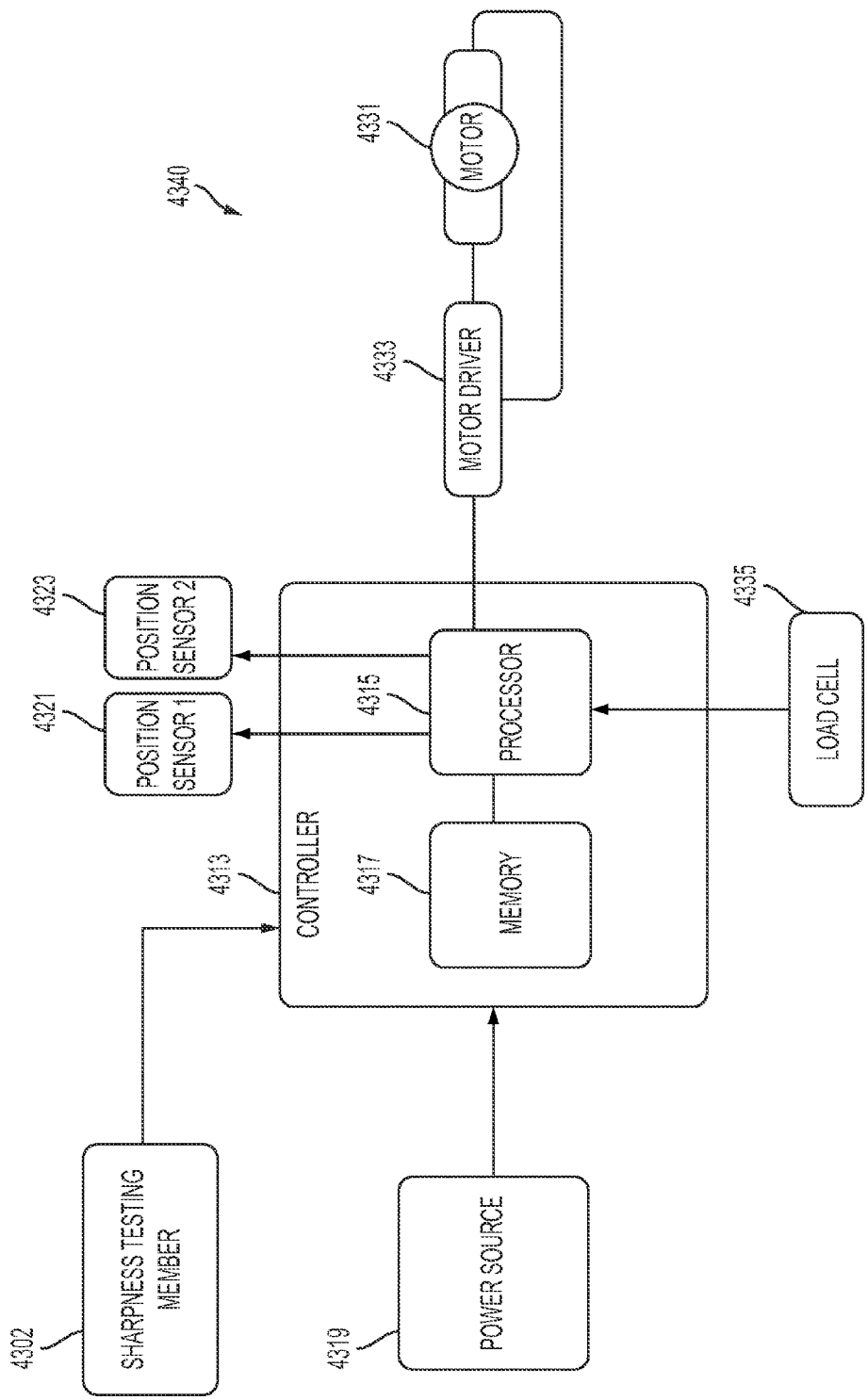
FIG. 39 illustrates a logic diagram of a system for determining the forces applied against a cutting edge of a surgical instrument by a sharpness testing member at various sharpness levels according to various aspects.

FIG. 39 illustrates a logic diagram of a system 4340 for determining the forces applied against a cutting edge of a surgical instrument 10 (FIGS. 1-4) by a sharpness testing member 4302 at various sharpness levels according to various aspects. Referring to FIG. 39, in various instances, an electric motor 4331 can drive the firing bar 172 (FIG. 20) to advance the cutting edge 182 (FIG. 20) during a firing stroke and/or to retract the cutting edge 182 during a return stroke, for example. A motor driver 4333 can control the electric motor 4331; and a microcontroller such as, for example, the microcontroller 4313 can be in signal communication with the motor driver 4333. As the electric motor 4331 advances the cutting edge 182, the microcontroller 4313 can determine the current drawn by the electric motor 4331, for example. In such instances, the force required to advance the cutting edge 182 can correspond to the current drawn by the electric motor 4331, for example. Referring still to FIG. 39, the microcontroller 4313 of the surgical instrument 10 can determine if the current drawn by the electric motor 4331 increases during advancement of the cutting edge 182 and, if so, can calculate the percentage increase of the current.

In certain instances, the current drawn by the electric motor 4331 may increase significantly while the cutting edge 182 (FIG. 20) is in contact with the sharpness testing member 4302 due to the resistance of the sharpness testing member 4302 to the cutting edge 182. For example, the current drawn by the electric motor 4331 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the motor 4331 while the cutting edge is in contact with the sharpness testing member 4302 can increase as the sharpness of the cutting edge 182 decreases from repetitive use, for example.

In certain instances, the determined value of the percentage increase of the current drawn by the motor 4331 can be the maximum detected percentage increase of the current drawn by the motor 4331. In various instances, the microcontroller 4313 can compare the determined value of the percentage increase of the current drawn by the motor 4331 to a predefined threshold value of the percentage increase of the current drawn by the motor 4331. If the determined value exceeds the predefined threshold value, the microcontroller 4313 may conclude that the sharpness of the cutting edge 182 has dropped below an acceptable level, for example.

In certain instances, as illustrated in FIG. 39, the processor 4315 can be in communication with the feedback system and/or the lockout mechanism for example. In certain instances, the processor 4315 can employ the feedback system to alert a user if the determined value of the percentage increase of the current drawn by the motor 4331 exceeds the predefined threshold value, for example. In certain instances, the processor 4315 may employ the lockout mechanism to prevent advancement of the cutting edge 182 (FIG. 20) if the determined value of the percentage increase of the current drawn by the motor 4331 exceeds the predefined threshold value, for example. In certain instances, the system 4311 may include a first position sensor 4321 and a second position sensor 4323. The surgical instrument 10 (FIGS. 1-4) may include a load cell 4335.

In various instances, the microcontroller 4313 can utilize an algorithm to determine the change in current drawn by the electric motor 4331. For example, a current sensor can detect the current drawn by the electric motor 4331 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Figure 40:
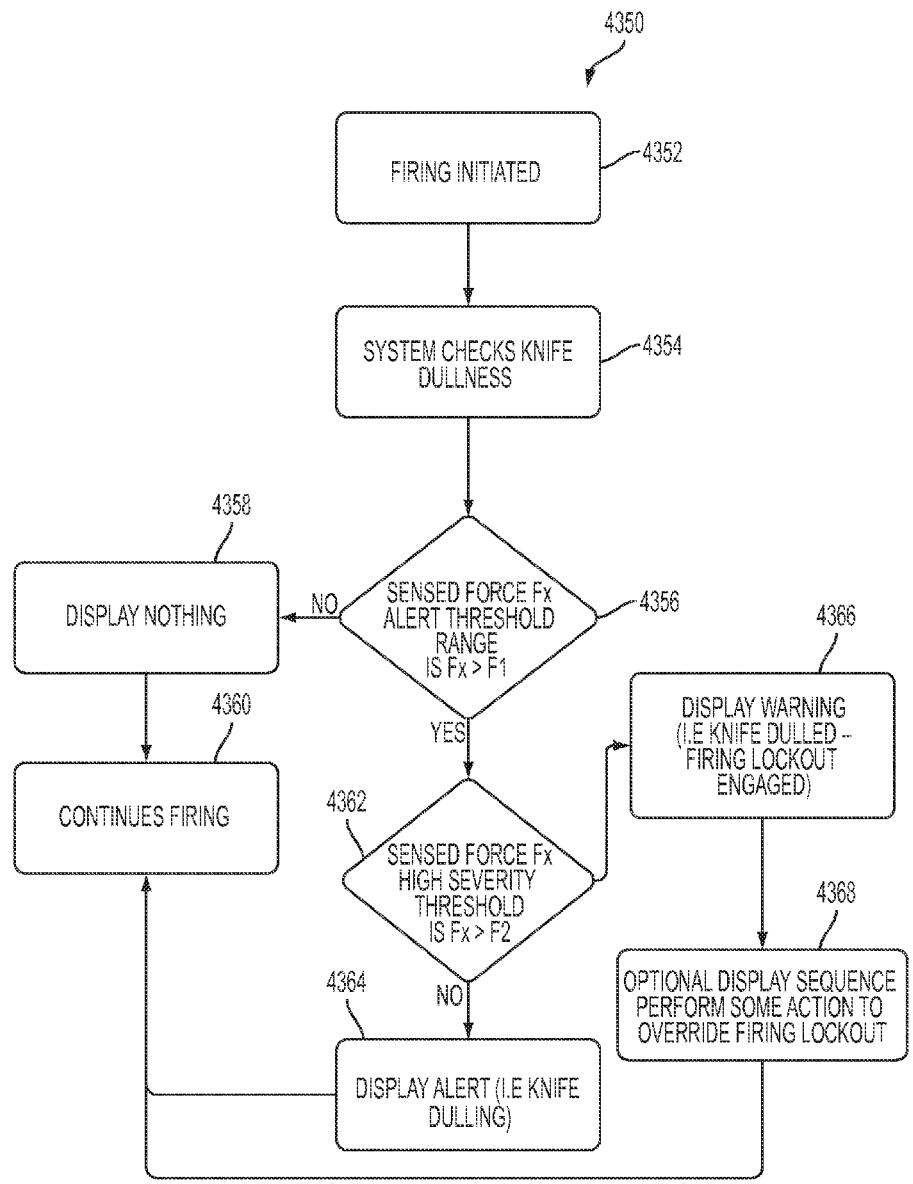
FIG. 40 illustrates a flow chart of a method for determining whether a cutting edge of a surgical instrument is sufficiently sharp to transect tissue captured by the surgical instrument according to various aspects.

FIG. 40 illustrates a logic diagram 4350 of a method for determining whether a cutting edge of a surgical instrument 10 (FIGS. 1-4) is sufficiently sharp to transect tissue captured by the surgical instrument 10 according to various aspects. Referring to FIG. 40, the logic diagram 4350 depicts a method for evaluating the sharpness of the cutting edge 182 (FIG. 20) of the surgical instrument 10; and various responses are outlined in the event the sharpness of the cutting edge 182 drops to and/or below an alert threshold and/or a high severity threshold, for example. In various instances, a microcontroller such as, for example, the microcontroller 4313 can be configured to implement the method 4350 depicted in FIG. 40. In certain instances, the surgical instrument 10 may include a load cell 4335, as illustrated in FIGS. 38 and 39, and the microcontroller 4313 may be in communication with the load cell 4335. In certain instances, the load cell 4335 may include a force sensor such as, for example, a strain gauge, which can be operably coupled to the firing bar 172, for example. In certain instances, the microcontroller 4313 may employ the load cell 4335 to monitor the force (Fx) applied to the cutting edge 182 as the cutting edge 182 is advanced during a firing stroke.

In various instances, the method 4350 begins by initiating 4352 firing of the surgical instrument 10 (FIGS. 1-4). Before, during, and/or after firing of the surgical instrument 10 is initiated 4352, a system checks 4354 the dullness of the cutting edge 182 by monitoring a force (Fx). The reader will appreciate that the force (Fx) is applied by the sharpness testing member 4302 to the cutting edge 182 while the cutting edge 182 is engaged and/or in contact with the sharpness testing member 4302, and, the force (Fx) may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302.

The system senses 4356 the force (Fx) applied by the sharpness testing member 4302 to the cutting edge 182 (FIG. 20). When the force (Fx) sensed 4356 stays within an alert threshold range a display will display 4358 nothing and firing 4360 of the surgical instrument 10 (FIGS. 1-4) will proceed. When the force (Fx) sensed 4356 is outside the alert threshold range, the system 4354 will then determine if the force (Fx) is outside a high severity threshold range. The display will display 4364 an alert to the user of the surgical instrument 10 that the cutting edge 182 is dulling. At this stage, the user is aware that the cutting edge 182 is dulling and may need replaced. When the force (Fx) is sensed 4362 to be greater than the high severity threshold range, the display displays 4366 a warning indicating that the force (Fx) applied to the cutting edge 182 is greater than the high severity threshold and that the cutting edge 182 is dull. If the cutting edge is determined to be dull, a firing lockout system may be engaged. The display may display 4368 an optional display sequence to allow the user of the surgical instrument 10 to override the firing lockout system and continue firing 4360 this surgical instrument 10.

In certain instances, the load cell 4335 (FIGS. 38, 39) can be configured to monitor the force (Fx) applied to the cutting edge 182 (FIG. 20) while the cutting edge 182 is engaged and/or in contact with the sharpness testing member 4302 (FIGS. 38, 39), for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. For example, as illustrated graphically in FIG. 41, graphs 4336, 4338, and 4342 represent, respectively, the force (Fx) applied to the cutting edge 182 while the cutting edge 182 travels a predefined distance (D) through three identical, or at least substantially identical, sharpness testing members 4302. The graph 4336 corresponds to a first sharpness of the cutting edge 182; the graph 4338 corresponds to a second sharpness of the cutting edge 182; and the graph 4342 corresponds to a third sharpness of the cutting edge 182. The first sharpness is greater than the second sharpness, and the second sharpness is greater than the third sharpness.

Figure 41:
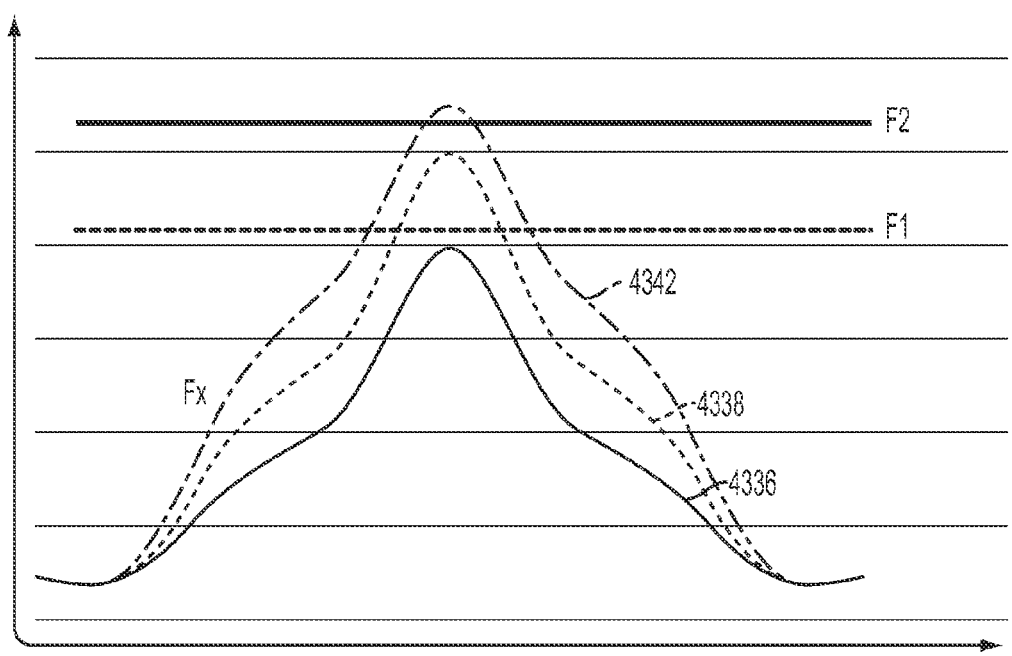
FIG. 41 illustrates a chart of the forces applied against a cutting edge of a surgical instrument by a sharpness testing member at various sharpness levels according to various embodiments.

In certain instances, the microcontroller 4313 (FIGS. 38, 39) may compare a maximum value of the monitored force (Fx) applied to the cutting edge 182 (FIG. 20) to one or more predefined threshold values. In certain instances, as illustrated in FIG. 41, the predefined threshold values may include an alert threshold (F1) and/or a high severity threshold (F2). In certain instances, as illustrated in the graph 4336 of FIG. 41, the monitored force (Fx) can be less than the alert threshold (F1), for example. In such instances, as illustrated in FIG. 41, the sharpness of the cutting edge 182 is at a good level and the microcontroller 4313 may take no action to alert a user as to the status of the cutting edge 182 or may inform the user that the sharpness of the cutting edge 182 is within an acceptable range.

In certain instances, as illustrated in the graph 4338 of FIG. 41, the monitored force (Fx) can be more than the alert threshold (F1) but less than the high severity threshold (F2), for example. In such instances, as illustrated in FIG. 40, the sharpness of the cutting edge 182 (FIG. 2) can be dulling but still within an acceptable level. The microcontroller 4313 may take no action to alert a user as to the status of the cutting edge 182. Alternatively, the microcontroller 4313 (FIGS. 38, 39) may inform the user that the sharpness of the cutting edge 182 is within an acceptable range. Alternatively or additionally, the microcontroller 4313 may determine or estimate the number of cutting cycles remaining in the lifecycle of the cutting edge 182 and may alert the user accordingly.

In certain instances, the memory 4317 (FIGS. 38, 39) may include a database or a table that correlates the number of cutting cycles remaining in the lifecycle of the cutting edge 182 (FIG. 20) to predetermined values of the monitored force (Fx). The processor 4315 (FIGS. 38, 39) may access the memory 4317 to determine the number of cutting cycles remaining in the lifecycle of the cutting edge 182 which correspond to a particular measured value of the monitored force (Fx) and may alert the user to the number of cutting cycles remaining in the lifecycle of the cutting edge 182, for example.

In certain instances, as illustrated in the graph 4342 of FIG. 41, the monitored force (Fx) can be more than the high severity threshold (F2), for example. In such instances, as illustrated in FIG. 40, the sharpness of the cutting edge 182 can be below an acceptable level. In response, the microcontroller 4313 may employ the feedback system to warn the user that the cutting edge 182 is too dull for safe use, for example. In certain instances, the microcontroller 4313 may employ the lockout mechanism to prevent advancement of the cutting edge 182 upon detection that the monitored force (Fx) exceeds the high severity threshold (F2), for example. In certain instances, the microcontroller 4313 may employ the feedback system to provide instructions to the user for overriding the lockout mechanism, for example.

Figure 42:
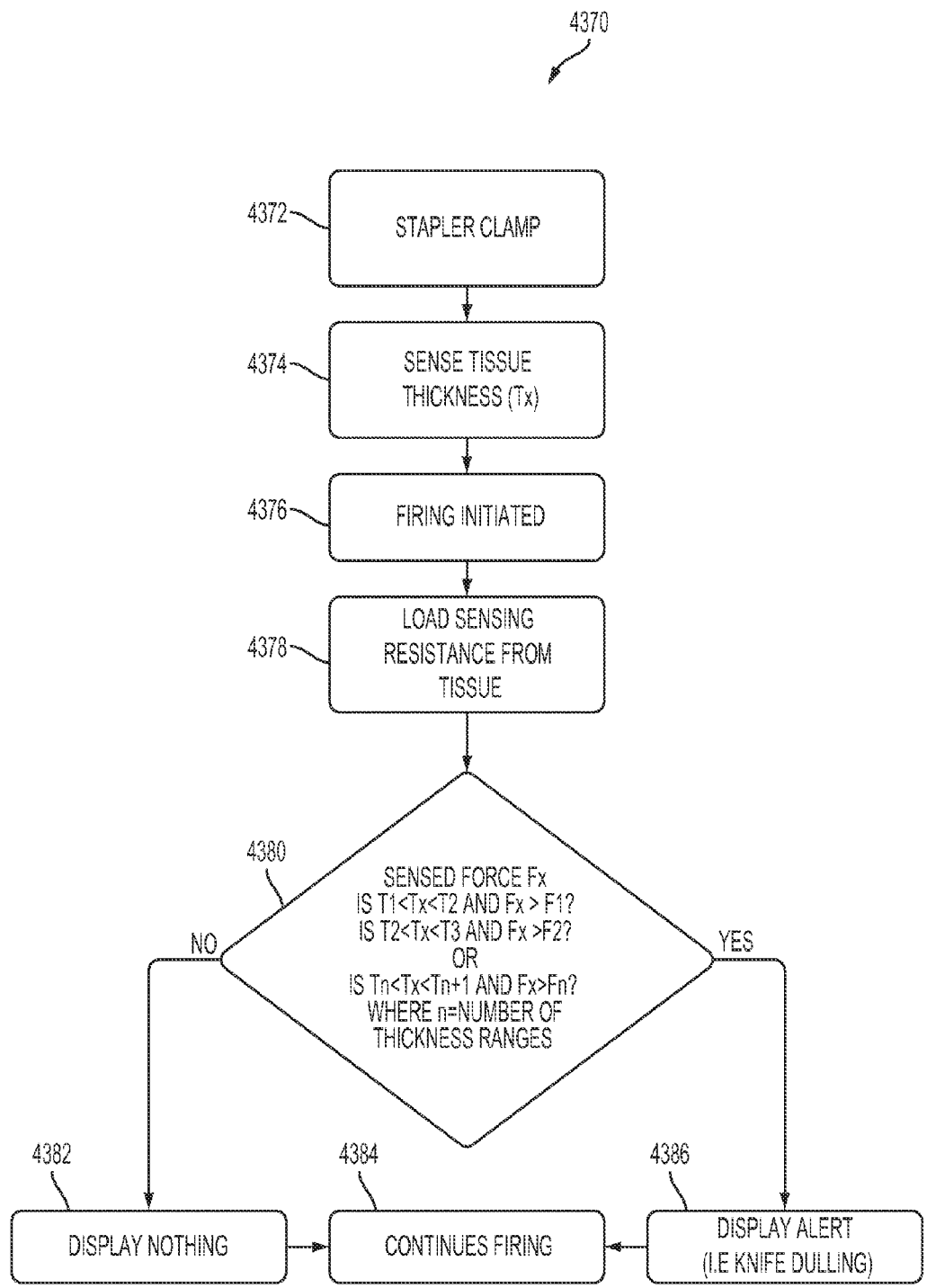
FIG. 42 illustrates a flow chart outlining a method for determining whether a cutting edge of a surgical instrument is sufficiently sharp to transect tissue captured by the surgical instrument according to various embodiments.

Referring now to FIG. 42, a method 4370 is depicted for determining whether a cutting edge such as, for example, the cutting edge 182 (FIG. 20) is sufficiently sharp to be employed in transecting a tissue of a particular tissue thickness that is captured by the end effector 300 (FIG. 1), for example. In certain instances, the microcontroller 4313 can be implemented to perform the method 4370 depicted in FIG. 42, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue also may depend on the thickness of the captured tissue. In certain instances, the greater the thickness of the captured tissue, the greater the force required for the cutting edge 182 to transect the captured tissue at the same sharpness level, for example.

In certain instances, the cutting edge 182 (FIG. 20) may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, the memory 4317 (FIGS. 38, 39) can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, when the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

The method 4370 shown in FIG. 42 begins with clamping 4372 the tissue. Once the tissue to be transected is clamped, the thickness of the tissue is sensed 4374. After the tissue thickness is sensed 4374, firing of the surgical instrument can be initiated 4376 by the user. Once the surgical instrument begins firing, the force (Fx) applied to the cutting edge 182 (FIG. 20) is sensed 4378. The force (Fx) and the tissue thickness (Tx) is then compared 4380 to predetermined tissue thickness ranges and force ranges required to adequately transect the predetermined tissue thicknesses. For example, if the force (Fx) sensed is greater than a predetermined force range required to adequately transect tissue at the tissue thickness (Tx) that was sensed for the tissue clamped, a display will display 4386 an alert to the user that the cutting edge 182 is dulling. When the force (Fx) sensed is within the predetermined force range required to adequately transect tissue at the tissue thickness (Tx) that was sensed for the tissue clamped, the display may display 4382 nothing. In both instances, the surgical instrument continues 4384 firing to transect the tissue.

The present disclosure will now be described in connection with various examples and combinations of such examples as set forth hereinbelow.

1. One example provides a surgical cutting and stapling instrument comprising at least one processor and operatively associated memory, the instrument configured to: identify a parameter; identify a value of an ultimate threshold for the parameter; and identify a value of a marginal threshold for the parameter.

2. Another example provides the instrument of example 1, wherein operations of the instrument are adjusted based on a determination that a measured value of the parameter exceeds the value of the ultimate threshold.

3. Another example provides the instrument of examples 1 or 2, wherein operations of the instrument are adjusted based on a determination that a measured value of the parameter exceeds the value of the marginal threshold.

4. Another example provides the instrument of examples 1, 2, or 3, wherein a modified rate of change of the value of the parameter is calculated based on a determination that a predicted rate of change of the value of the parameter will result in a value that will exceed the value of the ultimate threshold.

5. Another example provides the instrument of example 4, wherein operations of the instrument are adjusted based on the calculated modified rate of change of the parameter.

6. Another example provides the instrument of example 5, wherein the adjustment is based on a stepped function.

7. Another example provides the instrument of example 5, wherein the adjustment is based on a ramped function.

8. Another example provides the instrument of example 5, wherein the value of the calculated rate of change comprises a set of values located between the value of the marginal threshold and the value of the ultimate threshold.

9. Another example provides the instrument of any one of examples 1-8, wherein the value of the marginal threshold is approximately 75% of the value of the ultimate threshold.

10. Another example provides the instrument of any one of examples 1-9, wherein the parameter comprises current drawn by a battery associated with the instrument.

11. Another example provides the instrument of any one of examples 1-10, wherein the parameter comprises voltage of a battery associated with the instrument.

12. Another example provides the instrument of any of example 1-11, wherein the parameter comprises speed of a knife fired by the instrument.

13. Another example provides the instrument of any one of claims 1-12, wherein the parameter comprises a number of sterilization cycles associated with the surgical instrument.

14. Another example provide the instrument of any one of examples 1-13, wherein the parameter comprises a measured behavior of a clinician during operation of the instrument.

15. Yet another example, provides a surgical cutting and stapling instrument comprising at least one processor and operatively associated memory, the surgical instrument configured to: identify a first parameter; identify a second parameter; and identify a specified threshold, the specified threshold comprising one or more of: a value of an ultimate threshold for the first parameter; a value of a marginal threshold for the first parameter; a value of an ultimate threshold for the second parameter; and a value of a marginal threshold for the second parameter.

16. Another example provides the instrument of example 15, further configured to adjust operations upon a determination that a specified threshold has been exceeded.

17. Another example provides the instrument of example 15 or 16, further configured to store an overlaying threshold, the overlaying threshold based on a mathematical relationship between, on one hand, the value of the first ultimate threshold or the value of the first marginal threshold, and, on the other hand, the value of the second ultimate threshold or the value of the second marginal threshold.

18. Another example provide the instrument of any one of examples 15-17, wherein the first parameter comprises speed of a motor of the instrument, and the second parameter comprises a number of sterilization cycles of the instrument.

19. Another example provides the instrument of any one of examples 15-18, wherein the first parameter comprises a speed of a knife deployed by the instrument, and the second parameter is a number of sterilization cycles of the instrument.

20. Another example provides the instrument of any one of examples 15-19, wherein a third threshold is identified based on a determination that the instrument has exceeded a value of a specified threshold.

In accordance with various examples, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various aspects, the operating logic may be configured to perform the initial processing, and transmit the data to the computer hosting the application to determine and generate instructions. For these examples, the operating logic may be further configured to receive information from and provide feedback to a hosting computer. In alternate examples, the operating logic may be configured to assume a larger role in receiving information and determining the feedback. In either case, whether determined on its own or responsive to instructions from a hosting computer, the operating logic may be further configured to control and provide feedback to the user.

In various aspects, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other examples, the operating logic may be implemented in hardware such as a gate array.

In various aspects, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various examples, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various aspects, the processor may be packaged together with the operating logic. In various examples, the processor may be packaged together with the operating logic to form a SiP. In various examples, the processor may be integrated on the same die with the operating logic. In various examples, the processor may be packaged together with the operating logic to form a System on Chip (SoC).

Various aspects may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some aspects may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other examples, the functional components such as software, engines, and/or modules may be implemented by hardware elements that may include processors, microprocessors, circuits, circuit elements (e.g., transistors, resistors, capacitors, inductors, and so forth), integrated circuits, ASICs, PLDs, DSPs, FPGAs, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether one example is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application APIs, and so forth. The firmware may be stored in a memory of the controller and/or the controller which may comprise a nonvolatile memory (NVM), such as in bit-masked ROM or flash memory. In various implementations, storing the firmware in ROM may preserve flash memory. The NVM may comprise other types of memory including, for example, programmable ROM (PROM), erasable programmable ROM (EPROM), EEPROM, or battery backed RAM such as dynamic RAM (DRAM), Double-Data-Rate DRAM (DDRAM), and/or synchronous DRAM (SDRAM).

In some cases, various aspects may be implemented as an article of manufacture. The article of manufacture may include a computer readable storage medium arranged to store logic, instructions and/or data for performing various operations of one or more examples. In various examples, for example, the article of manufacture may comprise a magnetic disk, optical disk, flash memory or firmware containing computer program instructions suitable for execution by a general purpose processor or application specific processor. The examples, however, are not limited in this context.

The functions of the various functional elements, logical blocks, modules, and circuits elements described in connection with the examples disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media.

In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the aspects described herein illustrate example implementations, and that the functional elements, logical blocks, modules, and circuits elements may be implemented in various other ways which are consistent with the described examples. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual examples described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one example" or "an example" means that a particular feature, structure, or characteristic described in connection with the example is comprised in at least one example. The appearances of the phrase "in one example" or "in one aspect" in the specification are not necessarily all referring to the same example.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some aspects may be described using the expression "coupled" and "connected" along with their derivatives. These terms are not intended as synonyms for each other. For example, some aspects may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, API, exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure applies to conventional endoscopic and open surgical instrumentation as well as application in robotic-assisted surgery.

Aspects of the devices disclosed herein can be designed to be disposed of after a single use, or they can be designed to be used multiple times. Examples may, in either or both cases, be reconditioned for reuse after at least one use. Reconditioning may include any combination of the steps of disassembly of the device, followed by cleaning or replacement of particular pieces, and subsequent reassembly. In particular, examples of the device may be disassembled, and any number of the particular pieces or parts of the device may be selectively replaced or removed in any combination. Upon cleaning and/or replacement of particular parts, examples of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically matable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more"

or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A surgical cutting and stapling instrument, comprising:
at least one processor and operatively associated memory;
a first sensor, wherein the first sensor is coupled to the at least one processor;
a second sensor, wherein the second sensor is coupled to the at least one processor; and
a motor, wherein function of the motor is controlled by the at least one processor;
wherein the surgical instrument is configured to:
identify a first parameter associated with the surgical cutting and stapling instrument;
identify a second parameter associated with the surgical cutting and stapling instrument;
measure, by the first sensor, a first present value for the first parameter;
measure, by the second sensor, a second present value for the second parameter;
define a first ultimate threshold for the first parameter;
define a first marginal threshold for the first parameter;
define a second ultimate threshold for the second parameter;
define a second marginal threshold for the second parameter;
compare, by the at least one processor, the measured first present value of the first parameter with the first marginal threshold and the first ultimate threshold;
compare, by the at least one processor, the measured second present value of the second parameter with the second marginal threshold and the second ultimate threshold;
slow a first rate of operation of the surgical cutting and stapling instrument at which the first present value of the first parameter approaches the first ultimate threshold for the first parameter when the measured first present value for the first parameter exceeds the first marginal threshold for the first parameter;
slow a second rate of operation of the surgical cutting and stapling instrument when the measured second present value for the second parameter exceeds the second marginal threshold for the second parameter;
return a knife to a pre-fired position or cease operation of the surgical cutting and stapling instrument when the measured first present value of the first parameter exceeds the first ultimate threshold for the first parameter; and
return the knife to the pre-fired position or cease operation of the surgical cutting and stapling instrument when the measured second present value of the second parameter exceeds the second ultimate threshold for the second parameter,
store an overlaying threshold, the overlaying threshold based on a mathematical relationship between the value of the first ultimate threshold or the value of the first marginal threshold, and the value of the second ultimate threshold or the value of the second marginal threshold, wherein there is an interactive association between the value of the first ultimate threshold or the value of the first marginal threshold, and the value of the second ultimate threshold or the value of the second marginal threshold,
wherein the surgical cutting and stapling instrument is further configured to adjust the second marginal threshold if the measured first present value for the first parameter exceeds the first marginal threshold for the first parameter.

2. The instrument of claim 1, further configured to adjust operations upon a determination that at least one of the first marginal threshold, the first ultimate threshold, the second marginal threshold, and the second ultimate threshold has been exceeded.

3. The instrument of claim 1 wherein the first parameter comprises speed of the motor of the instrument, and the second parameter comprises a number of sterilization cycles of the instrument.

4. The instrument of claim 1 wherein the first parameter comprises a speed of the knife deployed by the instrument, and the second parameter is a number of sterilization cycles of the instrument.

5. The instrument of claim 1, wherein a third threshold is identified based on a determination that the instrument has exceeded a value of at least one of the first marginal threshold, the first ultimate threshold, the second marginal threshold, and the second ultimate threshold.

6. The instrument of claim 1, wherein at least one of the first and second parameters represents quantities, amounts, states, or events.

7. The instrument of claim 6, wherein at least one of the first and second parameters is at least one of closure clamp loads, current draw, pressure, firing load, torque, sterilization cycles, voltage, speed of the knife fired, tissue pressure, tissue thickness, tissue gap, jaw closure rate, tissue creep rate, knife thickness, battery usage, and battery charge.

8. A method of operating a surgical cutting and stapling instrument, the method comprising:
identifying a first parameter associated with the surgical cutting and stapling instrument;
identifying a second parameter associated with the surgical cutting and stapling instrument;
measuring, by a first sensor coupled to at least one processor of the surgical cutting and stapling instrument, a first present value for the first parameter;
measuring, by a second sensor coupled to at least one processor of the surgical cutting and stapling instrument, a second present value for the second parameter;
defining a first ultimate threshold for the first parameter;
defining a first marginal threshold for the first parameter;
defining a second ultimate threshold for the second parameter;
defining a second marginal threshold for the second parameter;
comparing, by the at least one processor, the measured first present value of the first parameter with the first marginal threshold and the first ultimate threshold;
comparing, by the at least one processor, the measured second present value of the second parameter with the second marginal threshold and the second ultimate threshold;
slowing a first rate of operation of the surgical cutting and stapling instrument at which the first present value of the first parameter approaches the first ultimate threshold for the first parameter when the measured first present value for the first parameter exceeds the first marginal threshold for the first parameter;
slowing a second rate of operation of the surgical cutting and stapling instrument when the measured second present value for the second parameter exceeds the second marginal threshold for the second parameter;
returning a knife to a pre-fired position or ceasing operation of the surgical cutting and stapling instrument when the measured first present value of the first parameter exceeds the first ultimate threshold for the first parameter; and
returning the knife to the pre-fired position or ceasing operation of the surgical cutting and stapling instrument when the measured second present value of the second parameter exceeds the second ultimate threshold for the second parameter;
storing an overlaying threshold, the overlaying threshold based on a mathematical relationship between the value of the first ultimate threshold or the value of the first marginal threshold, and the value of the second ultimate threshold or the value of the second marginal threshold, wherein there is an interactive association between the value of the first ultimate threshold or the value of the first marginal threshold, and the value of the second ultimate threshold or the value of the second marginal threshold; and
adjusting the second marginal threshold if the measured first present value for the first parameter exceeds the first marginal threshold for the first parameter.

9. The method of claim 8, further comprising adjusting operations upon a determination that at least one of the first marginal threshold, the first ultimate threshold, the second marginal threshold, and the second ultimate threshold has been exceeded.

10. The method of claim 8, wherein the first parameter comprises speed of a motor of the instrument, and the second parameter comprises a number of sterilization cycles of the instrument.

11. The method of claim 8, wherein the first parameter comprises a speed of the knife deployed by the instrument, and the second parameter is a number of sterilization cycles of the instrument.

12. The method of claim 8, wherein a third threshold is identified based on a determination that the instrument has exceeded a value of at least one of the first marginal threshold, the first ultimate threshold, the second marginal threshold, and the second ultimate threshold.

13. The method of claim 8, wherein at least one of the first and second parameters represents quantities, amounts, states, or events.

14. The method of claim 13, wherein at least one of the first and second parameters is at least one of closure clamp loads, current draw, pressure, firing load, torque, sterilization cycles, voltage, speed of the knife fired, tissue pressure, tissue thickness, tissue gap, jaw closure rate, tissue creep rate, knife thickness, battery usage, and battery charge.

* * * * *